(12) United States Patent
Dewey et al.

(10) Patent No.: US 7,884,263 B2
(45) Date of Patent: Feb. 8, 2011

(54) ALTERATION OF TOBACCO ALKALOID CONTENT THROUGH MODIFICATION OF SPECIFIC CYTOCHROME P450 GENES

(75) Inventors: Ralph E. Dewey, Apex, NC (US); Steven W. Bowen, Raleigh, NC (US); Balazs Siminszky, Lexington, KY (US); Lily Gavilano, Lexington, KY (US)

(73) Assignees: North Carolina State University, Raleigh, NC (US); University of Kentucky Research Foundation, Lexington, KY (US)

( * ) Notice: Subject to any disclaimer, the term of this patent is extended or adjusted under 35 U.S.C. 154(b) by 869 days.

(21) Appl. No.: 11/580,765

(22) Filed: Oct. 13, 2006

(65) Prior Publication Data
US 2008/0202541 A1 Aug. 28, 2008

Related U.S. Application Data

(63) Continuation-in-part of application No. PCT/US2005/005665, filed on Feb. 23, 2005.

(51) Int. Cl.
*C12N 15/82* (2006.01)
(52) U.S. Cl. ...................................... 800/285; 800/287
(58) Field of Classification Search ........................ None
See application file for complete search history.

(56) References Cited

U.S. PATENT DOCUMENTS

| 5,668,295 | A  | 9/1997 | Wahab et al. |
| 5,684,241 | A  | 11/1997 | Nakatani et al. |
| 2004/0103449 | A1 | 5/2004 | Xu |
| 2004/0111759 | A1 | 6/2004 | Xu |
| 2004/0117869 | A1 | 6/2004 | Xu |
| 2004/0162420 | A1 | 8/2004 | Xu |
| 2005/0132444 | A1 | 6/2005 | Xu |
| 2006/0037096 | A1 | 2/2006 | Xu |

FOREIGN PATENT DOCUMENTS

| WO | WO 00/67558 A1 | 11/2000 |
| WO | WO 03/078577 A2 | 9/2003 |
| WO | WO 2004/035745 A2 | 4/2004 |
| WO | WO 2005/038018 A2 | 4/2005 |
| WO | WO 2005/038033 A2 | 4/2005 |
| WO | WO 2005/111217 A2 | 11/2005 |
| WO | WO 2005/116199 A2 | 12/2005 |
| WO | WO 2006/091194 A1 | 8/2006 |

OTHER PUBLICATIONS

Klahre et al., PNAS, 2002, vol. 99, pp. 11981-11986.*
Gavilano et al., "Genetic Engineering of *Nicotiana tabacum* for Reduced Nornicotine Content," *J. Agric. Food. Chem.*, 2006, pp. 9071-9078, vol. 54, No. 11.
Siminszky et al., "Conversion of Nicotine to Nornicotine in *Nicotiana tabacum* Is Mediated by CYP82E4, a Cytochrome P450 Monooxygenase," *Proceedings of the National Academy of Sciences of USA*, 2005, pp. 14919-14924, vol. 102, No. 41.
Tang et al., "Using RNAi to Improve Plant Nutritional Value: From Mechanism to Application," *Trends in Biotechnology*, 2004, pp. 463-469, vol. 22, No. 9.
Chintapakorn, Y., et al., "Antisense-Mediated Down-Regulation of Putrescine N-Methyltransferase Activity in Transgenic *Nicotiana tabacum* L. can Lead to Elevated Levels of Anatabine at the Expense of Nicotine," *Plant Molecular Biology*, 2003, pp. 87-105, vol. 53.

\* cited by examiner

*Primary Examiner*—Ashwin Mehta
(74) *Attorney, Agent, or Firm*—Alston & Bird LLP

(57) ABSTRACT

Compositions and methods for reducing the level of nornicotine and N'-nitrosonornicotine (NNN) in *Nicotiana* plants and plant parts thereof are provided. The compositions comprise isolated polynucleotides and polypeptides for cytochrome P450s that are involved in the metabolic conversion of nicotine to nornicotine in these plants. Expression cassettes, vectors, plants, and plant parts thereof comprising inhibitory sequences that target expression or function of the disclosed cytochrome P450 polypeptides are also provided. Methods for the use of these novel sequences to inhibit expression or function of cytochrome P450 polypeptides involved in this metabolic conversion are also provided. The methods find use in the production of tobacco products that have reduced levels of nornicotine and its carcinogenic metabolite, NNN, and thus reduced carcinogenic potential for individuals consuming these tobacco products or exposed to secondary smoke derived from these products.

25 Claims, 14 Drawing Sheets

```
3D_C12      GTGGGATTTTCAAGGCCATATTAAGGCAATGAAAAGGACATTTAAGGATATAGAGATTCTGTT    777
3D_C12-10   GTGGGATTTTCAAGGCCATGTTAAGGCAATGAAAAGGACATTTTAAAGATATAGAGATTCTGTT   777
3D_C12-7    GTGGGATTTTCAAGGCCATGTTAAGGCTATGAAAAGGACTATTTAAAGATATAGAGATTCTGTT   777
7D_A06      GTGGGATTTTCAAGGCCATGTTAAGGCTATGAAAAGGACTTTTAAAGATATAGAGATTCTGTT    777
            *************** *** ***** ********* ** ************************

3D_C12      TTTCAGAATGGTTAGAGGAACATATTAATAAAGAGAAAAAAT---GGAGGTTGGTGCA        834
3D_C12-10   TTTCAGAATGGTTAGAGGAACATATTAATAATAAAAGAGAAAAAT---GGAGGTTGGTATGCA  834
3D_C12-7    TTTCAGAATGGTTAGAGGAACATATTAATAATAAAAGAGAAAAAT---GGAGGTTGGTATGCA  834
7D_A06      TTTCAGAATGGTTAGAGGAACATATTAATAAATAAAAGAGAAAAAATAAAGGAGGTTGGTCA   837
            ************************ ****** ** *********    *********  **

3D_C12      GAAGGGAATGAACAAGATTTCATTGATGTGGTGCTTTCAAAAATGAGTAAGAATATCTTT    894
3D_C12-10   GAAGGGAATGAACAAGATTTCATTGATGTGGTGCTTTCAAAAATGAGTAATGAATATCTTT   894
3D_C12-7    GAAGGGAATGAACAAGATTTCATTGATGTGGTGCTTTCAAAAATGAGTAATGAATATCTTT   894
7D_A06      GAAGGGAATGAACAAGATTTAATGATGTGGTGCTTTCAAAAATGAGTAATGAATATCTTT    897
            ******************** * ********************** *  **********

3D_C12      GGTGAAGGTTACTCTCGTGATACTGTCATTAAAGCAACAGTTTTTAGTTTGGTCTTGGAT     954
3D_C12-10   GGTGAAGGTTACTCTCGTGATACTGTCATTAAAGCAACCGTCTTTAGTTGGTCTTGGAT     954
3D_C12-7    GGTGAAGGTTACTCTCGTGATACTGTCATTAAAGCAACCGTCTTTAGTTGGTCTTGGAT      954
7D_A06      GGTGAAGGTTACTCTCGCGATACTGTCATTAAAGCAACAGTCTTTAGTTTGGTCTTGGAT    957
            ***************** ******************* ** *****  ***********

3D_C12      GCAGCAGAGACACAGTTGCTCTTCACATAAATAAGAACATTATTGATAAACAATCAA      1014
3D_C12-10   GCAGCAGAGACACAGTTGCTCTTCACATAAATAAATTGGGAATGGCATTAATTGATAACAATCAA  1014
3D_C12-7    GCAGCAGAGACACAGTTGCTCTTCACATAAATAAATTGGGAATGGCATTAATTGATAACAATCAA  1014
7D_A06      GCAGCAGAGACACAGTTGCTCTTCACATAAATAAATTGGGAATGGCATTAATTGATAAACAATCAA 1017
            *********************************    *   *** ********* *********
```

Figure 3E

```
3D_C12      AATGCCTTGACGAAGCACAAGAGAGATAGACACAAAAGTTGGTAAGGATAGATGGGTA      1074
3D_C12-10   AAGGCCTTGACGAAAGCACAAGAGAGAGATAGACACAAAAGTTGGTAAGGAGAGATGGGTA   1074
3D_C12-7    AAGGCCTTGACGAAAGCACAAGAGAGAGATAGACACAAAAGTTGGTAAGGAGAGATGGGTA   1074
7D_A06      AATGCCTTGAGGAAGAACACAAGAGAGAGATAGACACAAAAGTTGGTAAGGATAGATGGGTA  1077
            ** * ****** ** **  ************************** ***** ********

3D_C12      GAAGAGAGTGATATTAAGGATTTAGTATACCTTCCAAGCTATTGTTAAAAAGTGTTACGA    1134
3D_C12-10   GAAGAGAGTGATATTAAGGATTTGGTATACCTCCAAGCTATTGTTAAAGAAGTGTTACGA   1134
3D_C12-7    GAAGAGAGTGATATTAAGGATTTGGTATACCTCCAAGCTATTGTTAAAGAAGTGTTACGA   1134
7D_A06      GAAGAGAGTGATATTAAGGATTTAAGTATACCTCCAAGCTATTGTTAAAGAAGTGTTACGA  1137
            *********************** ******** ***********  ** ***********

3D_C12      TTATATCCACCAGGACCTTTGTTAGTACCACAGAAAAATGTAAAGATTGTGTTGTTAGT    1194
3D_C12-10   TTATATCCACCAGGACCTTTGTTAGTACCACAGAAATGTAGAAGATTGTGTTGTTAGT     1194
3D_C12-7    TTATATCCACCAGGACCTTTGTTAGTACCACAGAAATGTAGAAGATTGTGTTGTTAGT     1194
7D_A06      TTATATCCACCCGGACCTTTGTTAGTACCACACAGAAATGTAGAAGATTGTGTTGTTAGT   1197
            ***********.********************    * ** * ****************

3D_C12      GGATATCACATTCCTAAAGAGACTAGATTATTCGCAAAGGTCATGAAACTGCAGCGGAT    1254
3D_C12-10   GGATATCACATTCCTAAAGGACAGAGATTATTCGCAAACGTCATGAAACTGCAACGTGAT   1254
3D_C12-7    GGATATCACATTCCTAAAGGAGAAGAGATTATTCGCAAACGTCATGAAACTGCAACGTGAT  1254
7D_A06      GGATATCACATTCCTAAAGAGTATTCGATTATTCGCAAAGTATGAAACTCAAGGTGAT     1257
            ******************* *   * *************    ******* **  ****

3D_C12      CCTAAACTCTCTTGTCAAATCCTGATAAGTTCGATCCAGAGAGTTCATCGCTGTGATATT   1314
3D_C12-10   CCTAAACTCTGGTCTGATCCTGATCCTGATAAGTTCGATCCAGAGAGATTCATGCTAGTGATATT 1314
3D_C12-7    CCTAAACTCTGGTCTGATCCTGATCCTGATAAGTTCGATCCAGAGAGATTCATGCATGATGATATT 1314
7D_A06      CCTAAACTCTGGTCAAATCCTGATAAGTTCATGCAGAGAGAGATTCATCGCTGTGATATT   1317
            **********  ** ******************       * ****** **  *******
```

Figure 3F

```
3D_C12       GACTTTCGTGGTCAGGACTATGAGTTTATCCCATTTGGTTCTGGAAGACGATCTTGTCCG   1374
3D_C12-10    GACTTTCGTGGTCAGTACTACTATAAGTAGTATATCCCGTTTGGTTCTGGAAGACGATCTTGTCCA   1374
3D_C12-7     GACTTTCGTGGTCAGTACTACTATAAGTATATATCCCGTTTGGTTCTGGAAGACGATCTTGTCCA   1374
3D_A06       GACTTTTCATGGTCAGGACTACTGAGTATATCCCGTTTGGTTCTGGAAGACGGTCTTGTCCG   1377
             *****  * ********  ****** **** *** ********************   ******* -

3D_C12       GGGATGACTTATGCAAGTGCAATGCATTGCAAGTGCAACACCTAACAATGGCACATTTAATCGAGGGTTTC   1434
3D_C12-10    GGGATGACTTATGCAAGTGCATTGCAAGTGCAACACCTAACAATGGCACATTTGATCCAAGGTTTC   1434
3D_C12-7     GGGATGACTTATGCAAGTGCATTGCAAGTGCAACACCTAACAATGGCACATTTGATCCAAGGTTTC   1434
3D_A06       GGGATGACTTATGCAAGTGCATTGCAAGTGCAACACCTAACAATGGCACATTTGATCCAGGGGTTTC   1437
             ******************  ****************  ****************** **** **** -

3D_C12       AATTACAGAACAACTCCAAATGACGAGCCCTTGGATATGAAGGAAGGTGCAGGCATAACAATA   1494
3D_C12-10    AATTACAGAACTCCTGTGACGAGCCCTTGGATATGAAGGAAGGTGCAGGCATAACAATA   1494
3D_C12-7     AATTACAGAACTCCAAATGACGAGCCCTTGGATATGAAGGAAGGTGCAGGCATAACTATA   1494
3D_A06       AATTACAGAACTCCAAGTGATGAGCCCTTGGATATGAAGGAAGGTGCAGGCATAACTATA   1497
             ************     ***** ***********************  ****

3D_C12       CGTAAGGTAAATCCAGTGAATGATAATAACGCCTCGGCCTGGCACCTGAGCTTTATAA   1554
3D_C12-10    CGTAAGGTAAATCCTGTGAACTGGGAACTGATAATAATAGGCCTGGCACCTGAGCTTTATAA   1554
3D_C12-7     CGTAAGGTAAATCCTGTGAACTGGGAACTGATAATAACGCCTCGCCTGGCACCTGAGCTTTATAA   1554
3D_A06       CGTAAGGTAAATCCTGTGAATGATAATACGCCTGGCACCTGAGCTTTATTAA   1557
             ************** *****         * *****  ** * * **************** -

3D_C12       AACCTAAGATCTTTCATCTTGGTTGATCATTGTTTAATACTCCTAGATGGGTATTCATTT   1614
3D_C12-10    AACCTAAGATCTTTCATCTTCATCTTGGTTGATCATTGTATAATACTCCTAGATGGATATTCATTT   1614
3D_C12-7     AACCTAAGATCTTTCATCTTCATCTTGGTTGATCATTGTATAATACTCCTAAATGGATATTCATTT   1614
3D_A06       AACCTAAGATCTTTCATCTTGGTTGATCATTGTTTAATACTCCTAGATGGGTATTCATGT   1617
             *************  *     ********** **   ** ******   * ****** -
```

Figure 3G

```
3D_C12        ACCTTTTTTCAATTAATTGCATGTACGAGGTTTTTAATTTGTAAGAATAA   1674
3D_C12-10     ACCTTTTTATCAATTAATTGTCAGTACGAGTTTTTCTAATTTGTACATTAA  1674
3D_C12-7      ACCTTTTTATCAATTAATTGTCAGTACGAGTTTTTCTAATTTGTAATAATAA 1674
7D_A06        ACCTTTTTTCAATTAGTGTCTGTACGNATTTTTTTAATTGGTTTGTAATAATAA 1677
              * *******  *****   *  ***** *****  ***** ****  ****

3D_C12        GTAAAGAATGATTGTGCTAATATATATAAGATTTGCAGAAGATAATGACTGATTGTCCC   1733
3D_C12-10     GTAAAGAATAATTGTGCTAATATATATAAAGGTTTGNAGAAGATAATGACTGATTGTCCQ  1733
3D_C12-7      GTAAAGAATAATTGTGCTAATATATATAAAGGTTTGNAGAAGATAATGACTGATTGTCCC  1733
7D_A06        GTAAAGAAGGATTGTGCTAAATATATATAAAGGT--GCANAAATAATTGAAAG        1727
              ******** **** *** ************  *    *  * **** ****
```

Figure 4

```
3D_C12     MVFPIEAIVGLVTFTFLFFFLWTKKSQKPSKPLPPKIPGGWPVIGHLFHENNDGDDRPLA  60
3D_C12-7   MVFPIEAIVGLVTFTFLFFFLWTKKSQKPSKPLPPKIPGGWPVIGHLFHFNDDGDDRPLA  60
3D_C12-10  MFSPIEAIVGLVTFTFLFFFLWTKKSQKPSKPLPPKIPGGWPVIGHLFHFNDDGDDRPLA  60
7D_A06     MVFPFEAIVGLVTFTFLFFFLWTKKSQKPSKPLPPKIPGGWPVIGHLFFFDDGDDRPLA   60
           *:  *:**.*********.**:*******  ****************** . *******

3D_C12     RKLGDLADKYGPVFTFRLGLPLVLVVSSYEAFKDCFSTNDAIFSNRPAFLYGEYLGYNNT  120
3D_C12-7   RKLGDLADKYGPVFTFRLGLPLVLVVSSYEAVKDCFSTNDAIFSNRPAFLYGDYLGYNNA  120
3D_C12-10  RKLGDLADKYGPVFTFRLGLPLVLVVSSYEAVKDCFSTNDAIFSNRPAFLYGDYLGYNNA  120
7D_A06     RKLGDLADKYGPVFTFRLGLPLVLVVSSYEAFKDCFSTNDAIFSNRPAFLYGEYLGYNNA  120
           ******************************.:*******************:*****:

3D_C12     MLFLANYGPYWRKNRKLVIQEVLSASRLEKFKQVRFIRIQSIKNLYTRINGNSSTINLT  180
3D_C12-7   MLFLANYGPYWRKNRKLVIQEVLSASRLEKFKHVRFARIQASIKNLYTRIDGNSSTINLT  180
3D_C12-10  MLFLANYGPYWRKNRKLVIQEVLSASRLEKFKHVRFARIQASIKNLYTRIDGNSSTINLT  180
7D_A06     MLFLANYGSYWRKNRKLIIQEVLSASRLEKFKHVRFARIQSIKNLYTRIDGNSSTINLT  180
           ********.*******::*************:***:***:*********:*********

3D_C12     DWLEELNFGLIVKMIAGKNYESGKGDEQVERFKNAFKDFMVLSMEFVLWDAFPIPLFKWV  240
3D_C12-7   DWLEELNFGLIVKMIAGKNYESGKGDEQVERFKKAFKDFMILSMEFVLWDAFPIPLFKWV  240
3D_C12-10  DWLEELNFGLIVKMIAGKNYESGKGDEQVERFKKAFKDFMILSMEFVLWDAFPIPLFKWV  240
7D_A06     DWLEELNFGLIVKMIAGKNYESGKGDEQVERFKKAFKDFMILSMEFVLWDAFPIPLFKWV  240
           *********************************:******:******************

3D_C12     DFQGHFKAMKRTFKDIDSVFQNWLEEHINKREK-MEVGAEGNEQDFIDVVLSKLSFEYLG  299
3D_C12-7   DFQGHVKAMKRTFKDIDSVFQNWLEEHINKREK-MEVNAEGNEQDFIDVVLSKMSNEYLG  299
3D_C12-10  DFQGHVKAMKRTFKDIDSVFQNWLEEHINKREK-MEVNAEGNEQDFIDVVLSKMSNEYLG  299
7D_A06     DFQGHVKAMKRTFKDIDSVFQNWLEEHIKKREKFMEVSTEGNEQDFIDVVLSKMSNEYLG  300
           *****:**********************:**** ***..:***********::*:***

3D_C12     EGYSRDTVIKATVFSLVLDAADTVALHINWGMFLLINNQNALSKAQEEIDTKVGKDRWVE  359
3D_C12-7   EGYSRDTVIKATVFSLVLDAADTVALHINWGMALLINNQKALTKAQEEIDTKVGKDRWVE  359
3D_C12-10  EGYSRDTVIKATVFSLVLDAADTVALHINWGMALLINNQKALTKAQEEIDTKVGKDRWVE  359
7D_A06     EGYSRDTVIKATVFSLVLDAADTVALHINGGMALLINNQFALSKAQEEIDTKVGKDRWVE  360
           ****************************** ** ****.**:****************

3D_C12     ESDIKDLVYLQAIVKFVLRLYPPGPLLVPHENVFDCVVSGYHIPKFTRLFANVMKLQRDP  419
3D_C12-7   ESDIKDLVYLQAIVKEVLRLYPPGPLLVPHENVEDCVVSGYHIPKGTRLFANVMKLQRDP  419
3D_C12-10  ESDIKDLVYLQAIVKEVLRLYPPGPLLVPHENVEDCVVSGYHIPKGTRLFANVMKLQRDP  419
7D_A06     ESDIKDLVYLQAIVKEVLRLYPPGPLLVPHENVEDCVVSGYHIPKGTRLFANVMKLQRDP  420
           ***************:****************.***********.*************

3D_C12     KLFSNPDFFDPERFIAFDIDFRGFYYFIPFGSGRRSCPGMTYALQVEHLTMAHLIQGFN  479
3D_C12-7   KLWSDPDTFDPERFIATDIDFRGQYYKYIPFGSGRRSCPGMTYALQVEHLTMAHLIQGFN  479
3D_C12-10  KLWSDPDTFDPERFIATDIDFRGQYYKYIPFGSGRRSCPGMTYALQVEHLTMAHLIQGFN  479
7D_A06     KLFSNPDFFDPERFIAFDIDFFGFYYFIPFGSGRRSCPGMTYALQVEHLTMAHLIQGFN  480
           **:*:**.*:*******.***** :*:*.******************************

3D_C12     YRTPNDEFLDMKEGAGITIRKVNPVELIIFPRLAPELY  517
3D_C12-7   YRTPNDEPLDMKEGAGITIRKVNPVELIIAPRLAPELY  517
3D_C12-10  YRTPNDEPLDMKEGAGITIRKVNPVELIIAPRLAPELY  517
7D_A06     YRTPFDEPLDMKEGAGITIRKVNPVFIIFPRLAPELY  518
           ****.**.*****************:.**:*******
```

Figure 7

CTGTCATTAAAGCAACGGTGTTT*GTAAGTTCATCTGTCATTTTTCATTTATTCACTT*
*TTATTTTGAGGAGCAGACATGTTAATAATAATTTGGAGCAACTGTAAAGTTATCTAT*
*GTGTACAGGTTCGAGCCTCAGGTGCAACCACTAATGCTTGTATTAGATTATGTTGT*
*CTGCATCATACCCCTAATTGGAGTGTGGCTCTTCCCGAACCCTGCAATGCTGGATG*
*CTGGATGCTTTATGTATCAGACTGACCTTTTTGTTAAACTATCTAAATACTAAGGAT*
*GATTTAATAAAAATATAGAATGGTAAACAGAAAAAGATGAGATTATTTTTGGGGCT*
*ATATGGATTCGCCCGGGCTTTGGGAGGTAAAACGGTATCTACCAGTTGAGACTTTA*
*CTCCAGAACTTTATCTCGAGAGCTCTGAATAAAAATGAAATAGTATTTACCACTCCA*
*AAATCTTTGATGGTAAAAAGATGAGATATAACCTCTTATAATTGATTGAACCACGTT*
*GATAGAATAAAACTTCTTTACTCCCATTCAGCATAAGAAAAATGAAACCAAACGGA*
*ATTCTTCTCTTTTTAGGGGGAAATTCCTTAATTGCTTGTTGAATATAGATTCATGT*
*CGTTATTCTATTTTTAATAATGATGAAAATCAATATAGTCAAAGTTAATACTTATGT*
*CATTTGGTTTGCGGACAAGTTATATTGGAACTATATAATACGTCTATTATAGAATAG*
*TGATTATTTAGAGGATATACATTTTTTTTGGATAAATATTTGATTTATTGGATTAAAA*
*ATAGAATATACAGGTAAGGTCTAAAACGTGTGTTTGCTTTTACACTAAATAAACTTG*
*ACCTCGTACAATTCTAAGAAAATATTTGAAATAAATGAATTATTTTATTGTTAATCA*
*ATTAAAAAAATCATAGTATAGATGAGATGTGTGCATACTTGGCAATAACTATACTAA*
*CTAAAACAAGGTATGTGAATAATTGATATTCCTTTTTTAATTATTCTTTTTTCCAGA*
GTTTGGTCTTGGATGCAGCAGACACAGTTGCTCTTCACATAAATTGGGGAATGGC
ATTATTGATAAACAATCAAAAGGCCTTGACGAAAGCACAAG

ALTERATION OF TOBACCO ALKALOID CONTENT THROUGH MODIFICATION OF SPECIFIC CYTOCHROME P450 GENES

CROSS-REFERENCE TO RELATED APPLICATION

This application is a continuation-in-part of International Application No. PCT/US2005/005665, filed Feb. 23, 2005, the content of which is herein incorporated by reference in its entirety.

FIELD OF THE INVENTION

The invention relates to compositions and methods for reducing the level of nornicotine and its metabolite, N'-nitrosonornicotine, in a plant that is a member of the genus *Nicotiana*, particularly compositions and methods for inhibiting expression or function of a cytochrome P450 polypeptide involved in the metabolic conversion of nicotine to nornicotine.

BACKGROUND OF THE INVENTION

The predominant alkaloid found in commercial tobacco varieties is nicotine, typically accounting for 90-95% of the total alkaloid pool. The remaining alkaloid fraction is comprised primarily of three additional pyridine alkaloids: nornicotine, anabasine, and anatabine. Nornicotine is generated directly from nicotine through the activity of the enzyme nicotine N-demethylase (FIG. 1). Nornicotine usually represents less than 5% of the total pyridine alkaloid pool, but through a process termed "conversion," tobacco plants that initially produce very low amounts of nornicotine give rise to progeny that metabolically "convert" a large percentage of leaf nicotine to nornicotine. In tobacco plants that have genetically converted (termed "converters"), the great majority of nornicotine production occurs during the senescence and curing of the mature leaf (Wernsman and Matzinger (1968) *Tob. Sci.* 12:226-228). Burley tobaccos are particularly prone to genetic conversion, with rates as high as 20% per generation observed in some cultivars.

During the curing and processing of the tobacco leaf, a portion of the nornicotine is metabolized to the compound N'-nitrosonornicotine (NNN; FIG. 1), a tobacco-specific nitrosamine (TSNA) that has been shown to be carcinogenic in laboratory animals (Hecht and Hoffmann (1990) *Cancer Surveys* 8:273-294; Hoffmann et al. (1994) *J. Toxicol. Environ. Health* 41:1-52; Hecht (1998) *Chem. Res. Toxicol.* 11:559-603). In flue-cured tobaccos, TSNAs were found to be predominantly formed through the reaction of alkaloids with the minute amounts of nitrogen oxides present in combustion gases formed by the direct-fired heating systems found in traditional curing barns (Peele and Gentry (1999) "Formation of Tobacco-specific Nitrosamines in Flue-cured Tobacco," CORESTA Meeting, Agro-Phyto Groups, Suzhou, China). Retrofitting these curing barns with heat-exchangers virtually eliminated the mixing of combustion gases with the curing air and dramatically reduced the formation of TSNAs in tobaccos cured in this manner (Boyette and Hamm (2001) *Rec. Adv. Tob. Sci.* 27:17-22). In contrast, in the air-cured Burley tobaccos, TSNA formation proceeds primarily through reaction of tobacco alkaloids with nitrite, a process catalyzed by leaf-borne microbes (Bush et al. (2001) *Rec. Adv. Tob. Sci.* 27:23-46). Thus far, attempts to reduce TSNAs through modification of curing conditions while maintaining acceptable quality standards have not proven to be successful for the air-cured tobaccos.

In Burley tobaccos, a positive correlation has been found between the nornicotine content of the leaf and the amount of NNN that accumulates in the cured product (Bush et al. (2001) *Rec. Adv. Tob. Sci.* 27:23-46; Shi et al. (2000)*Tob. Chem. Res. Conf.* 54:Abstract 27). However, keeping nornicotine levels at a minimum has been difficult because of the conversion phenomenon that results in a continual introduction of high nornicotine-producing plants within commercially grown Burley populations. Minimizing the number of Burley plants that accumulate high levels of nornicotine has traditionally been the responsibility of plant breeders and seed producers. Though the percentage of converter plants that are ultimately grown in farmers' fields can be reduced through the roguing of converter plants during the propagation of seed stocks, this process is costly, time-consuming, and imperfect.

Previous studies have shown that once a plant has converted, the high nornicotine trait is inherited as a single dominant gene (Griffith et al. (1955) *Science* 121:343-344; Burk and Jeffrey (1958) *Tob. Sci.* 2:139-141; Mann et al. (1964) *Crop Sci.* 4:349-353). The nature of this gene, however, is currently unknown. In the most simple of scenarios, the conversion locus may represent a nonfunctional nicotine N-demethylase gene that regains its function in converter plants, possibly through the mobilization of a mutation-inducing transposable element. Alternatively, the converter locus may encode a protein that initiates a cascade of events that ultimately enables the plant to metabolize nicotine to nornicotine, which would mean that multiple genes may be involved.

Regardless of whether there are one or many genes associated with the conversion process, it is clear that the gene(s) encoding polypeptides having nicotine demethylase activity play a pivotal role in this process. Although the inability to purify active nicotine N-demethylase from crude extracts has impeded the isolation and identification of this enzyme, there is some evidence that a member of the cytochrome P450 superfamily of monooxygenases may be involved (Hao and Yeoman (1996) *Phytochem.* 41:477-482; Hao and Yeoman (1996) *Phytochem.* 42:325-329; Chelvarajan et al. (1993) *J. Agric. Food Chem.* 41:858-862; Hao and Yeoman (1998) *J Plant Physiol.* 152:420-426). However, these studies are not conclusive, as the classic P450 inhibitors carbon monoxide and tetcylasis have failed to lower enzyme activity at rates comparable to other reported P450-mediated reactions (Chelvarajan et al. (1993) *J. Agric. Food Chem.* 41:858-862).

Furthermore, the cytochrome P450s are ubiquitous, transmembrane proteins that participate in the metabolism of a wide range of compounds (reviewed by Schuler (1996) *Crit. Rev. Plant Sci.* 15:235-284; Schuler and Werck-Reichhart (2003) *Annu. Rev. Plant Biol.* 54:629-667). Examples of biochemical reactions mediated by cytochrome P450s include hydroxylations, demethylations, and epoxidations. In plants, the cytochrome P450 gene families are very large. For example, total genome sequence examination has revealed 272 predicted cytochrome P450 genes in *Arabidopsis* and at least 455 unique cytochrome P450 genes in rice (see, for example, Nelson et al. (2004) *Plant Physiol.* 135(2):756-772). Even though cytochrome P450 has been implicated as having a role in the metabolic conversion of nicotine to nornicotine, identification of key participating members of this protein family remains a challenge.

Aside from serving as a precursor for NNN, recent studies suggest that the nornicotine found in tobacco products may have additional undesirable health consequences. Dickerson and Janda demonstrated that nornicotine causes aberrant protein glycation within the cell (Dickerson and Janda (2002) *Proc. Natl. Acad. Sci. USA* 99:15084-15088). Concentrations of nornicotine-modified proteins were found to be much higher in the plasma of smokers compared to nonsmokers. Furthermore, this same study showed that nornicotine can covalently modify commonly prescribed steroid drugs such as prednisone. Such modifications have the potential of altering both the efficacy and toxicity of these drugs.

In view of the difficulties associated with conversion and the undesirable health effects of nornicotine accumulation, improved methods for reducing the nornicotine content in tobacco varieties, particularly Burley tobacco, are therefore desirable. Such methods would not only help ameliorate the potential negative health consequences of the nornicotine per se as described above, but should also concomitantly reduce NNN levels.

SUMMARY OF THE INVENTION

Compositions and methods for reducing the nornicotine content in plants that are members of the genus *Nicotiana* are provided. Compositions include isolated cytochrome P450 polynucleotides and polypeptides that are involved in the metabolic conversion of nicotine to nornicotine in plants, particularly *Nicotiana* species. The isolated polynucleotides comprise the nucleotide sequence set forth in SEQ ID NO:1, 3, 5, 7, 9, or 11, a nucleotide sequence encoding a polypeptide as set forth in SEQ ID NO:2, 4, 6, 8, 10, or 12, and fragments and variants thereof. Isolated polypeptides of the invention comprise an amino acid sequence set forth in SEQ ID NO:2, 4, 6, 8, 10, or 12, an amino acid sequence encoded by the nucleotide sequence set forth in SEQ ID NO:1, 3, 5, 7, 9, or 11, and fragments and variants thereof.

The polynucleotides of the invention find use in suppressing expression of a cytochrome P450 that is involved in the metabolic conversion of nicotine to nornicotine in a plant, including the cytochrome P450s of the present invention. In this manner, compositions further include expression cassettes comprising an inhibitory sequence that is capable of inhibiting expression or function of a cytochrome P450 polypeptide of the invention, where the inhibitory sequence is operably linked to a promoter that is functional in a plant cell. In some embodiments, the inhibitory sequence comprises the sequence set forth in SEQ ID NO:1, 3, 5, 7, 9, 11, 13, 14, 15, or 16, or a complement or fragment thereof. Compositions also include transformed plants and plant parts that comprise an expression cassette of the present invention, optionally stably incorporated into the genome of the plant. Further provided are tobacco products, including chewing tobacco, snuff, cigarettes, pipe tobacco, and cigars, having a reduced level of nornicotine, and its related nitrosamine, N'-nitrosonornicotine.

The methods of the invention comprise inhibiting the expression or function of a cytochrome P450 polypeptide of the present invention. In some embodiments, an expression cassette comprising an inhibitory sequence that targets expression or function of a cytochrome P450 polypeptide of the present invention is introduced into the plant or plant part of interest, wherein expression of the inhibitory sequence produces a polynucleotide or polypeptide that inhibits expression or function of a cytochrome P450 polypeptide of the invention. In one such embodiment, the inhibitory sequence comprises a sequence set forth in SEQ ID NO:1, 3, 5, 7, 9, 11, 13, 14, 15, or 16, or a complement or fragment thereof.

The methods of the invention find use in the production of *Nicotiana* plants that have decreased levels of nornicotine and its metabolite, the nitrosamine N'-nitrosonornicotine, within the leaf and stem tissues. When harvested, the leaf and stem tissues of these plants can be utilized to produce tobacco products having reduced levels of nornicotine and this tobacco-specific nitrosamine, and thus reduced carcinogenic potential for individuals consuming these products or exposed to secondary smoke derived from these products.

Also provided are transgenic *Nicotiana* plants having a nicotine to nornicotine conversion rate of less than about 2%, where the plants comprise a heterologous nucleic acid construct comprising a promoter capable of functioning in a plant cell operably linked to a nucleic acid sequence having a first nucleotide sequence comprising a fragment of between about 100 nucleotides and about 400 nucleotides of a *Nicotiana* nicotine demethylase polynucleotide and a second nucleotide sequence capable of forming a double-stranded RNA with the first nucleotide sequence, where the transgenic *Nicotiana* plants are transgenic converter lines of *Nicotiana*. In some embodiments, the *Nicotiana* nicotine demethylase polynucleotide is a tobacco nicotine demethylase polynucleotide.

The present invention also provides a recombinant nucleic acid construct comprising a promoter capable of functioning in a plant cell operably linked to a nucleic acid sequence having a first nucleotide sequence comprising a fragment of between about 100 nucleotides and about 400 nucleotides of a tobacco nicotine demethylase polynucleotide and a second nucleotide sequence capable of forming a double-stranded RNA with the first nucleotide sequence.

Also provided are methods of reducing the conversion of nicotine to nornicotine in a *Nicotiana* plant comprising transforming a *Nicotiana* plant with a recombinant nucleic acid construct comprising a promoter capable of functioning in a plant cell operably linked to a nucleic acid sequence having a first nucleotide sequence comprising a fragment of between about 100 nucleotides and about 400 nucleotides of a *Nicotiana* nicotine demethylase polynucleotide and a second nucleotide sequence capable of forming a double-stranded RNA with the first nucleotide sequence; and regenerating a transgenic *Nicotiana* plant. In some embodiments, the *Nicotiana* nicotine demethylase polynucleotide is a tobacco nicotine demethylase polynucleotide.

The present invention also provides seed obtained from the transgenic *Nicotiana* plant having a nicotine to nornicotine conversion rate of less than about 2%, where the seed comprises a heterologous nucleic acid construct comprising a promoter capable of functioning in a plant cell operably linked to a nucleic acid sequence having a first nucleotide sequence comprising a fragment of between about 100 nucleotides and about 400 nucleotides of a *Nicotiana* nicotine demethylase polynucleotide and a second nucleotide sequence capable of forming a double-stranded RNA with the first nucleotide sequence, where the transgenic *Nicotiana* plants are transgenic converter lines of *Nicotiana*. In some embodiments, the *Nicotiana* nicotine demethylase polynucleotide is a tobacco nicotine demethylase polynucleotide.

The present invention also provides transgenic plant cells comprising a nucleic acid molecule having a promoter functional in a plant cell and a nucleic acid sequence encoding a nicotine demethylase having an isoleucine residue at position 274 and a tryptophan residue at position 330.

The present invention also provides methods of screening for a nicotine demethylase sequence comprising: obtaining a nucleic acid sequence that has greater than about 90% sequence identity with SEQ ID NO:5 and identifying a codon sequence encoding for a tryptophan residue at position 330 of the encoded polypeptide.

Further provided are methods for screening for a nicotine demethylase having an isoleucine at position 274 or a tryptophan at position 330 comprising obtaining a nucleic acid sequence that has greater than about 90% sequence identity with SEQ ID NO:5 and identifying a first codon sequence encoding for an isoleucine residue at position 274 or a second codon sequence encoding a tryptophan residue at position 330 of the encoded polypeptide.

BRIEF DESCRIPTION OF THE DRAWINGS

Figure 3A:
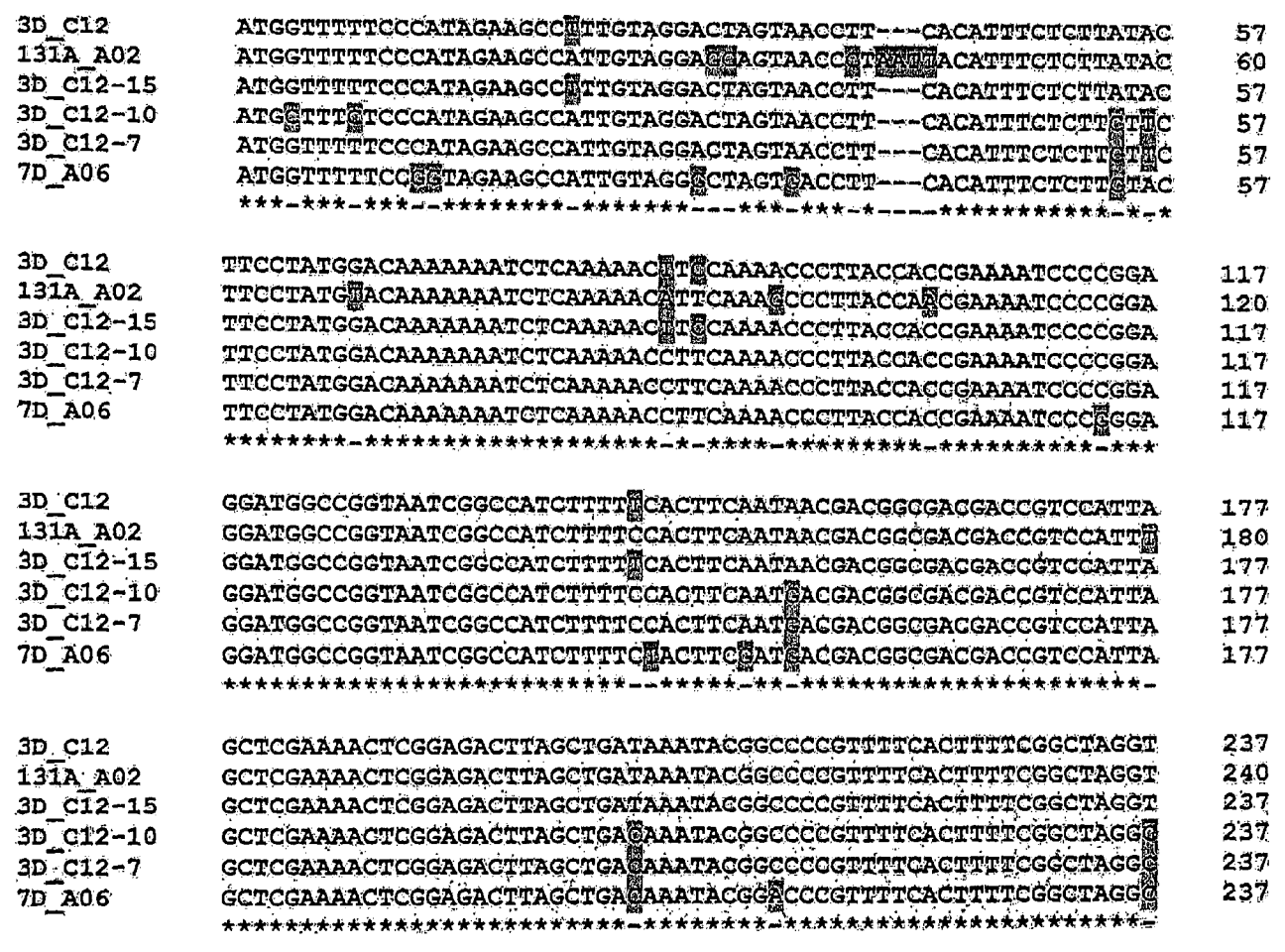
Figure 3B:
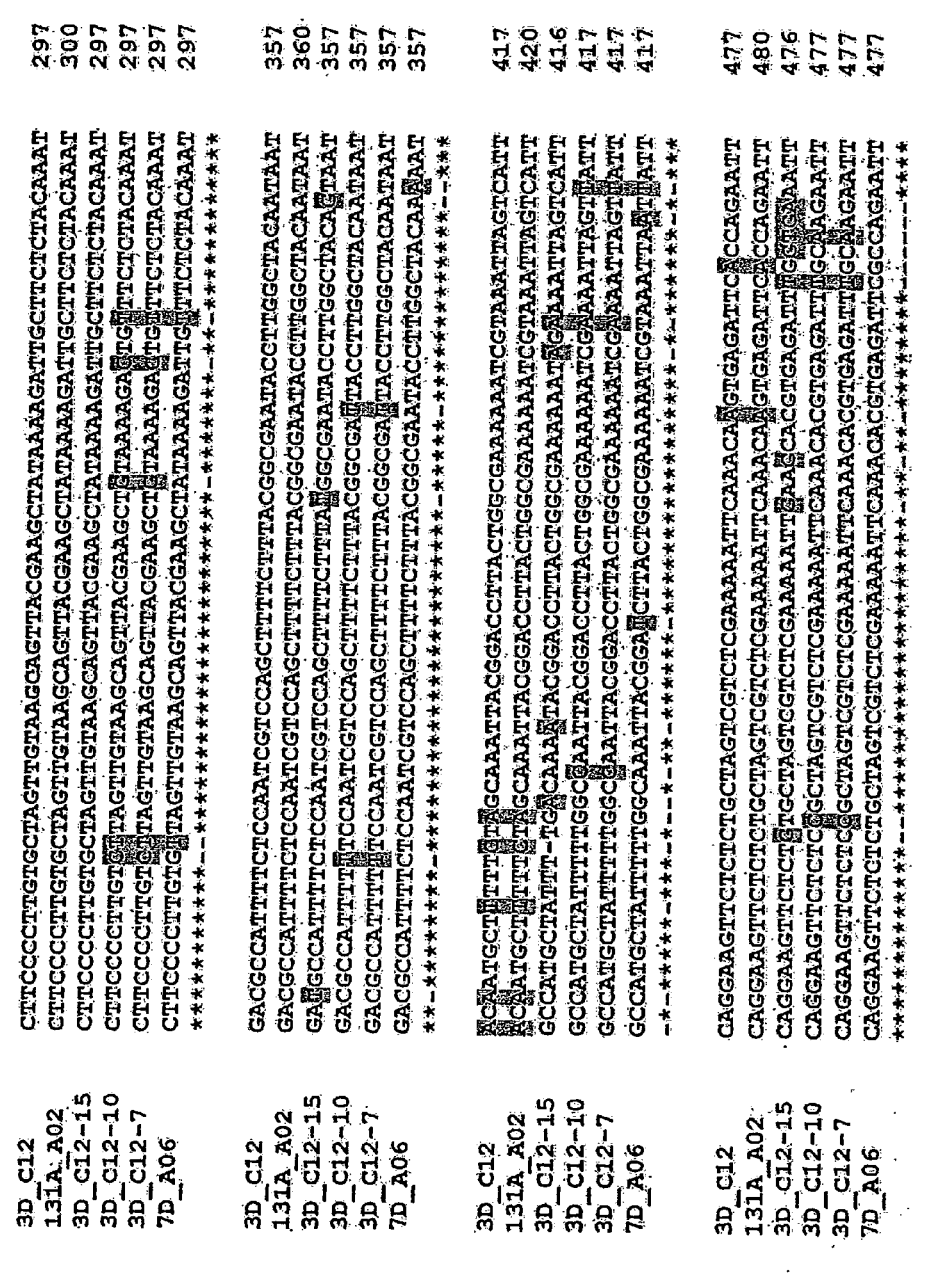
Figure 3C:
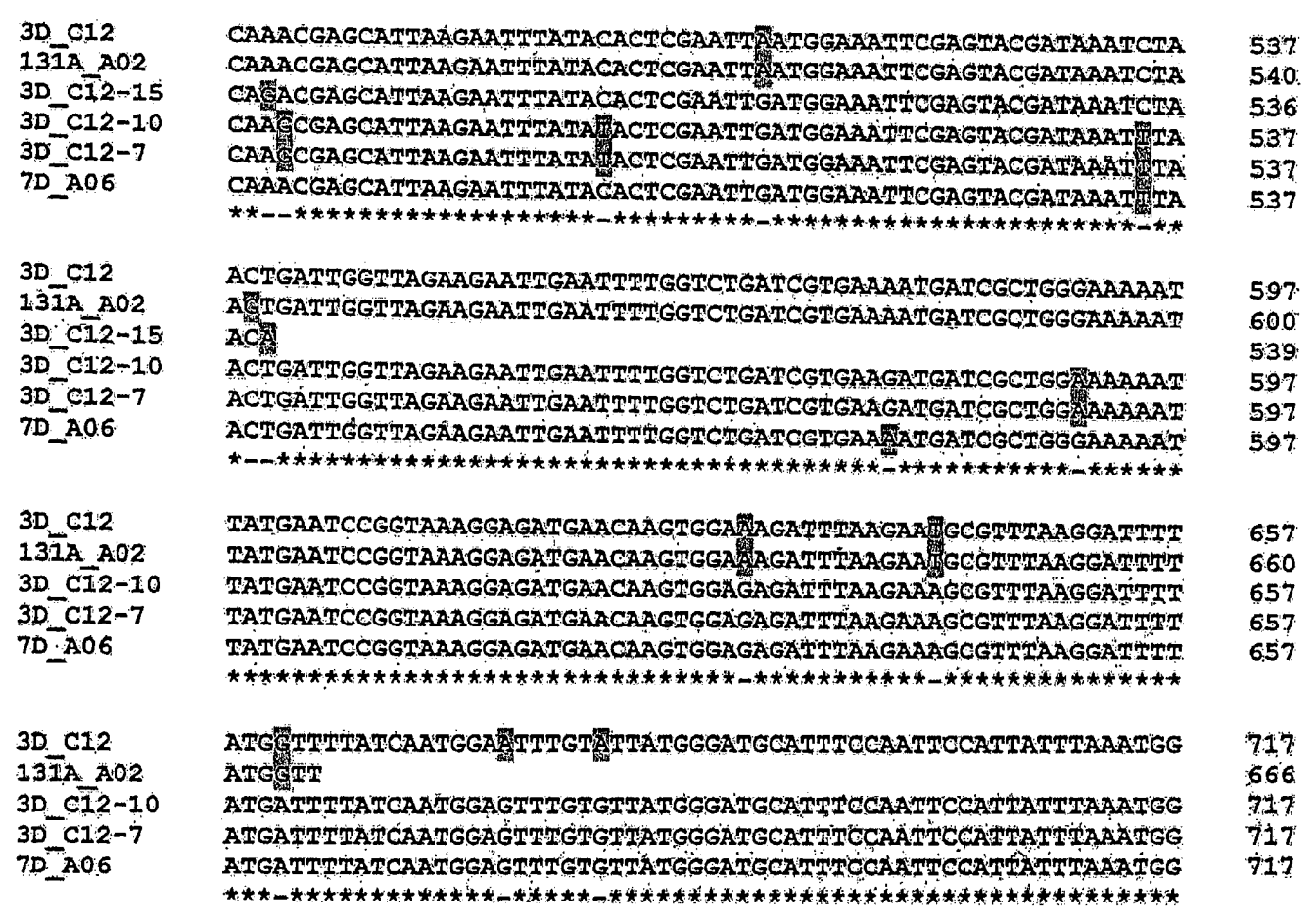

FIG. 3A-3G shows a nucleotide sequence alignment of members of the 3D_C12 gene family. Asterisks denote positions where sequence identity is conserved among all sequences compared. Positions where differences are found are indicated with dashes and the corresponding residues are shaded grey. The nucleotide sequences present in the alignment include 3D_C12 (SEQ ID NO:1), 3D_C12-10 (SEQ ID NO:3); 3D_C12-7 (SEQ ID NO:5); 7D_A06 (SEQ ID NO:7); 3D_C12-15 (SEQ ID NO:9); and 131A_A02 (SEQ ID NO:11). The 3D_C12-15 and 131A_A02 entries are partial-length cDNA sequences. The 99 bp region of 3D_C12 that was used to make the RNAi-based construct is underlined.

FIG. 4 shows an alignment of predicted amino acid sequences for full-length members of the 3D_C12 family of P450 genes. The amino acid sequences present in the alignment include 3D_C12 (SEQ ID NO:2), 3D_C12-10 (SEQ ID NO:4); 3D_C12-7 (SEQ ID NO:6); and 7D_A06 (SEQ ID NO: 8). Asterisks denote positions conserved among all four sequences. Residues that differ among the members are shaded in grey.

FIG. 7 shows a genomic sequence of a fragment of the 3D_C12-10 gene (see SEQ ID NO: 23) possessing an intron. Intron sequences are indicated in bold, italicized type. Exon sequences are shown in plain type. The sequences corresponding to the PCR primers used to amplify the fragment from the tobacco genomic DNA are underlined.

DETAILED DESCRIPTION OF THE INVENTION

Background and Definitions

Figure 1:
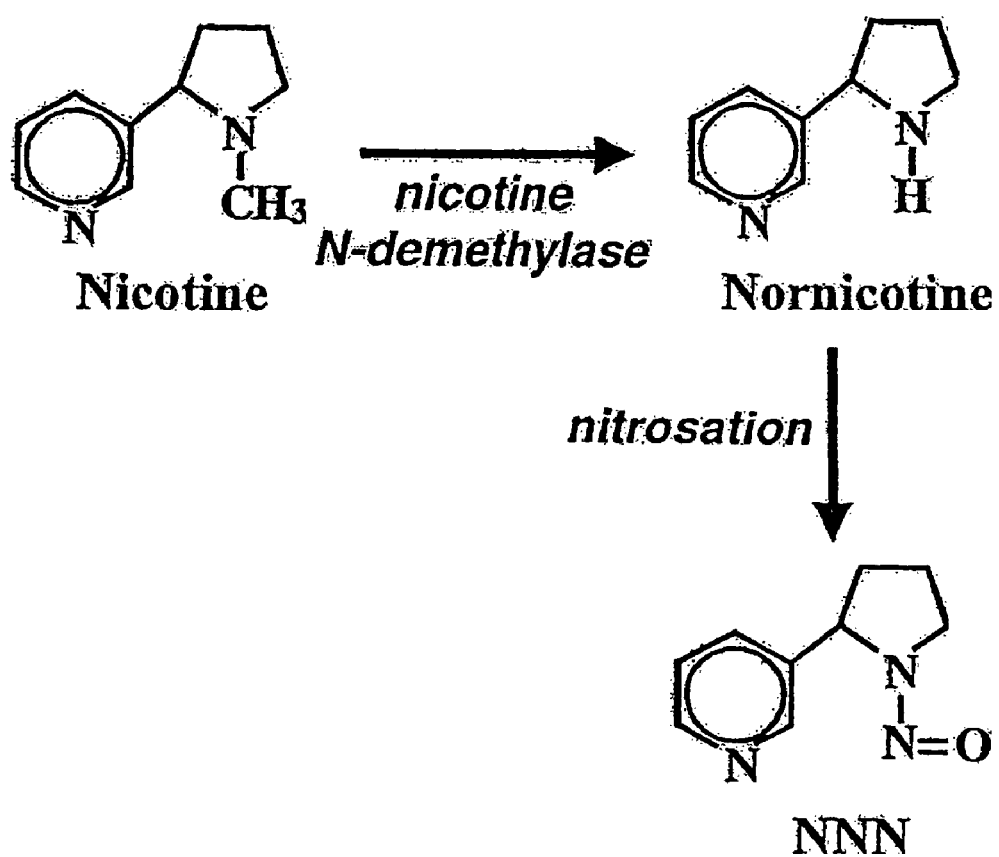
FIG. 1 shows the structures of nicotine, nornicotine, and N'-nitrosonornicotine (NNN).

Before describing the present invention in detail, it is to be understood that many modifications and other embodiments of the inventions set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Rather, these embodiments are provided so that this disclosure will satisfy applicable legal requirements.

Although specific terms are employed herein, they are used in a generic and descriptive sense only and not for purposes of limitation. Like numbers refer to like elements throughout. Further, the article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

The present invention is drawn to compositions and methods for inhibiting the expression or function of cytochrome P450 polypeptides that are involved in the metabolic conversion of nicotine to nornicotine in a plant, particularly plants of the *Nicotiana* genus, including tobacco plants of the various commercial varieties. As used herein, the terms "inhibit," "inhibition," and "inhibiting" are defined as any method known in the art or described herein that decreases the expression or function of a gene product of interest (i.e., the target gene product). "Inhibition" can be in the context of a comparison between two plants, for example, a genetically altered plant versus a wild-type plant. Alternatively, inhibition of expression or function of a target gene product can be in the context of a comparison between plant cells, organelles, organs, tissues, or plant parts within the same plant or between different plants, and includes comparisons between developmental or temporal stages within the same plant or plant part or between plants or plant parts. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product.

The term "inhibitory sequence" encompasses any polynucleotide or polypeptide sequence capable of inhibiting the expression or function of a cytochrome P450 polypeptide involved in the metabolic conversion of nicotine to nornicotine in a plant, such as full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

Inhibitory sequences are designated herein by the name of the target gene product. Thus, a "cytochrome P450 inhibitory sequence" refers to an inhibitory sequence that is capable of inhibiting the expression of a cytochrome P450 polypeptide that is involved in the metabolic conversion of nicotine to nornicotine in a plant, for example, at the level of transcription and/or translation, or which is capable of inhibiting the function of such a cytochrome P450 polypeptide. When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (i.e., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (i.e., inhibits expression or function of the target gene product).

By "host cell" is meant a cell that comprises a heterologous nucleic acid sequence of the invention. Though the nucleic acid sequences of the invention, and fragments and variants thereof, can be introduced into any cell of interest, of particular interest are plant cells, more particularly cells of a *Nicotiana* plant species, for example, the tobacco plant species and varieties described herein below.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The term "variant" as used herein is intended to mean a substantially similar sequence, and the term "native" polynucleotide or polypeptide is intended to mean a naturally occurring nucleotide sequence or amino acid sequence, respectively. By "fragment" is intended a portion of a polynucleotide or a portion of an amino acid sequence and hence protein encoded thereby.

As used herein, the term "plant part" includes plant cells, plant protoplasts, plant cell tissue cultures from which a whole plant can be regenerated, plant calli, plant clumps, and plant cells that are intact in plants or parts of plants such as embryos, pollen, anthers, ovules, seeds, leaves, flowers, stems, branches, fruit, roots, root tips, and the like. Progeny, variants, and mutants of regenerated plants are also included within the scope of the invention, provided that these comprise the introduced nucleic acid sequences of the invention.

By "phenotypic change" is intended a measurable change in one or more cell functions. For example, plants having a genetic modification at the genomic locus encoding a cytochrome P450 polypeptide of the invention can show reduced or eliminated expression or activity of that cytochrome P450 polypeptide.

The term "introducing" is intended to mean presenting to the plant the polynucleotide or polypeptide in such a manner that the sequence gains access to the interior of a cell of the plant.

The term "operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame.

The term "heterologous" according to the present invention when used in reference to a sequence is intended to mean a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest.

For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Furthermore, as used herein a chimeric gene comprises a coding sequence operably linked to a transcription initiation region that is heterologous to the coding sequence.

The term "expression" as used herein refers to the biosynthesis of a gene product, including the transcription and/or translation of said gene product. For example, for the purposes of the present invention, an expression cassette, as described elsewhere herein, capable of expressing a polynucleotide that inhibits the expression of at least one cytochrome P450 polypeptide of the invention is an expression cassette capable of producing an RNA molecule that inhibits the transcription and/or translation of at least one cytochrome P450 polypeptide. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Cytochrome 450 Polynucleotides and Polypeptides, and Variants and Fragments Thereof Compositions of the present invention include isolated cytochrome P450 polynucleotides and polypeptides that are involved in the metabolic conversion of nicotine to nornicotine in plants, including commercial varieties of tobacco plants. In particular, compositions of the invention include isolated polypeptides comprising the amino acid sequences as shown in SEQ ID NOS:2, 4, 6, 8, 10, and 12, and isolated polynucleotides comprising the nucleotide sequences as shown in SEQ ID NOS:1, 3, 5, 7, 9, and 11. The polynucleotides of the invention find use in inhibiting expression of these cytochrome P450 polypeptides or variants thereof that are involved in the metabolic conversion of nicotine to nornicotine in plants, particularly tobacco plants.

In this manner, the invention further provides expression cassettes comprising all or a portion of the polynucleotide sequence set forth in SEQ ID NO:1, 3, 5, 7, 9, or 11, a complement or fragment thereof, or a sequence having substantial sequence identity to SEQ ID NO:1, 3, 5, 7, 9, or 11, or a complement or fragment thereof, operably linked to a promoter that is functional in a plant cell for use in expressing an inhibitory RNA transcript that interferes with expression (i.e., transcription and/or translation) of cytochrome P450 polypeptides described herein. In some embodiments, the expression cassettes comprise the nucleotide sequence as shown in SEQ ID NO:13, 14, 15, or 16, a complement or fragment thereof, or a sequence having substantial sequence identity to SEQ ID NO:13, 14, 15, or 16, or a complement or fragment thereof. Introduction of these expression cassettes into a *Nicotiana* plant of interest, particularly a tobacco plant of varieties commonly known as flue or bright varieties, Burley varieties, dark varieties, and oriental/Turkish varieties, results in the production of tobacco plants having reduced amounts of nornicotine and the nitrosamine, N'-nitrosonornicotine (NNN). Leaf and stem material from these transgenic plants can be used to produce a variety of tobacco products having reduced levels of nornicotine, and a concomitant reduction in this carcinogenic nitrosamine metabolite.

The cytochrome P450 polynucleotides and encoded polypeptides of the present invention represent a novel cytochrome P450 gene family, designated the 3D_C12 cytochrome 450 gene family, that is newly identified as having a role in the metabolic conversion of nicotine to nornicotine in tobacco plants. Suppression of the expression of their encoded gene products in transgenic tobacco plants results in a significant reduction in the accumulation of nornicotine in the leaves of these transgenic plants. While not being bound by theory, the metabolic role of these polypeptides may be a direct one, i.e., directly catalyzing the N-demethylation reaction, or an indirect one, i.e., in the form of production of a product that leads to the up-regulation of the nicotine demethylase activity of the leaf. Regardless of the mechanism, any means by which expression and/or function of the polypeptides encoded by members of this cytochrome P450 gene family are targeted for inhibition within a *Nicotiana* plant will be effective in reducing nornicotine levels, and levels of its carcinogenic metabolite, NNN, within leaves and stems of these plants.

The cytochrome P450 genes of the invention were isolated from tobacco lines of a Burley variety. The first of these cytochrome P450 genes, designated 3D_C12, encodes an mRNA transcript corresponding to nucleotides (nt) 1-1551 of the cDNA sequence set forth in SEQ ID NO:1, which codes for the full-length 517-residue polypeptide set forth in SEQ ID NO:2. The second member of this novel cytochrome P450 family, designated 3D_C12-10, encodes an mRNA transcript corresponding to nt 1-1551 of the cDNA sequence set forth in SEQ ID NO:3, which codes for the full-length 517-residue polypeptide set forth in SEQ ID NO:4. The third of these cytochrome P450 genes, designated 3D_C12-7, encodes an mRNA transcript corresponding to nt 1-1551 of the cDNA sequence set forth in SEQ ID NO:5, which codes for the full-length 517 residue polypeptide set forth in SEQ ID NO:6. The fourth member of the novel cytochrome P450 family, designated 7D_A06, encodes an mRNA transcript corresponding to nt 1-1554 of the cDNA sequence set forth in SEQ ID NO:7, which codes for the full-length 518-residue polypeptide set forth in SEQ ID NO:8.

Two partial-length P450 gene sequences sharing high sequence identity to the full-length members of the 3D_C12 cytochrome P450 gene family were also isolated from these Burley tobacco lines. The first of these, designated 3D_C12-15, encodes an mRNA transcript corresponding to the cDNA sequence set forth in SEQ ID NO:9, which encodes the partial-length polypeptide set forth in SEQ ID NO:10. The second partial-length P450 gene sequence, designated 131A_A02, encodes an mRNA transcript corresponding to the cDNA sequence set forth in SEQ ID NO:11, which encodes the partial-length polypeptide set forth in SEQ ID NO:12.

In one aspect, the cytochrome P450 genes of the present invention are involved in the conversion of nicotine to nornicotine in a plant. In one aspect, the cytochrome P450 genes of the present invention have nicotine demethylase activity.

An alignment of the members of the 3D_C12 cytochrome P450 gene family is shown in FIG. 3A-3G. The predicted amino acid sequences for the four full-length clones are aligned in FIG. 4. These sequences share high sequence identity with each other (at least 90% at both the nucleotide and amino acid level (see Tables 2 and 3, Example 4 herein below).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments of the disclosed cytochrome P450 polynucleotides and polypeptides encoded thereby are also encompassed by the present invention. Fragments of a polynucleotide may encode protein fragments that retain the biological activity of the native protein and hence are involved in the metabolic conversion of nicotine to nornicotine in a plant. Alternatively, fragments of a polynucleotide that are useful as hybridization probes or PCR primers using methods described below generally do not encode fragment proteins retaining biological activity. Furthermore, fragments of the disclosed nucleotide sequences include those that can be assembled within recombinant constructs for use in gene silencing with any method known in the art, including, but not limited to, sense suppression/cosuppression, antisense suppression, double-stranded RNA (dsRNA) interference, hairpin RNA interference and intron-containing hairpin RNA interference, amplicon-mediated interference, ribozymes, and small interfering RNA or micro RNA, as described herein below. Thus, fragments of a cytochrome P450 polynucleotide sequence may range from at least about 20 nucleotides, about 50 nucleotides, about 70 nucleotides, about 100 nucleotides, about 150 nucleotides, about 200 nucleotides, about 250 nucleotides, about 300 nucleotides, about 350 nucleotides, about 400 nucleotides, and up to the full-length polynucleotide encoding the proteins of the invention, depending upon the desired outcome. In one aspect, the fragments of a cytochrome P450 polynucleotide sequence can be a fragment of between about 50 and about 400 nucleotides, between about 70 and about 350 nucleotides, between about 90 and about 325 nucleotides, between about 90 and about 300 nucleotides, between about 90 and about 275 nucleotides, between about 100 and about 400 nucleotides, between about 100 and about 350 nucleotides, between about 100 and about 325 nucleotides, between about 100 and about 300 nucleotides, between about 125 and about 300 nucleotides, or between about 125 and about 275 nucleotides in length. In some embodiments, a fragment of a cytochrome P450 polynucleotide is about 50, about 60, about 70, about 80, about 90, about 100, about 125, about 150, about 175, about 200, about 225, about 250, about 275, about 300, about 325, about 350, about 400 nucleotides in length, and other such values between about 70 and about 400 nucleotides. In one such embodiment, a fragment of a cytochrome P450 polynucleotide of the invention is about 90 bp to about 110 bp in length, including 90, 91, 92, 93, 94, 95, 96, 97, 98, 99, 100, 101, 102, 103, 104, 105, 106, 107, 108, 109, and 110 bp in length. In another such embodiment, a fragment of a cytochrome P450 polynucleotide of the invention is about 290 to about 310 bp in length, including 290, 291, 292, 293, 294, 295, 296, 297, 298, 299, 300, 301, 302, 303, 304, 305, 306, 307, 308, 309, and 310 bp in length.

A fragment of a cytochrome P450 polynucleotide of the present invention that encodes a biologically active portion of a cytochrome P450 polypeptide of the present invention will encode at least 15, 25, 30, 50, 75, 100, 125, 150, 175, 200, 250, 300, 350, 400, 450, or 500 contiguous amino acids, or up to the total number of amino acids present in a full-length cytochrome P450 polypeptide of the invention (e.g., 517 for SEQ ID NOS: 2, 4, and 6; and 518 for SEQ ID NO:8), or will encode at least 15, 25, 30, 50, 75, 100, 125, 150, or up to the total number of amino acids present in a partial-length cytochrome P450 polypeptide of the invention (e.g., 173 for SEQ ID NO:10; and 222 for SEQ ID NO:12). In one aspect, a fragment of a cytochrome P450 polynucleotide of the invention encodes a polypeptide that comprises position 330 of the encoded polypeptide sequence. In another aspect, the polynucleotide fragment encodes a fragment of a cytochrome P450 polypeptide, where the polypeptide fragment comprises the amino acids from position 225 through the amino acid at about position 600 of SEQ ID NO:6. In one such embodiment, the polynucleotide fragment encodes a fragment of a cytochrome P450 polypeptide, where the polypeptide fragment comprises the amino acids from about position 239 through the amino acid at about position 402 of SEQ ID NO:6. A biologically active portion of a cytochrome P450 polypeptide can be prepared by isolating a portion of one of the cytochrome P450 polynucleotides of the present invention, expressing the encoded portion of the cytochrome P450 polypeptide (e.g., by recombinant expression in vitro), and assessing the activity of the encoded portion of the cytochrome P450 polypeptide, i.e., the ability to promote conversion of nicotine to nornicotine, using assays known in the art and those provided herein below.

Polynucleotides that are fragments of a cytochrome P450 nucleotide sequence of the present invention comprise at least 16, 20, 50, 75, 100, 150, 200, 250, 300, 350, 400, 450, 500, 550, 600, 650, 700, 800, 900, 950, 1000, 1050, 1100, 1150, 1200, 1250, 1300, 1350, 1400, 1450, 1500, 1550, 1600, 1650, or 1700 contiguous nucleotides, or up to the number of nucleotides present in a full-length cytochrome P450 polynucleotide as disclosed herein (e.g., 539 for SEQ ID NO:9; 666 for SEQ ID NO:1; 1733 for SEQ ID NOS:1, 3, and 5; and 1727 for SEQ ID NO:7). Polynucleotides that are fragments of a cytochrome P450 nucleotide sequence of the present invention comprise fragments from about 20 to about 1700 contiguous nucleotides, from about 50 to about 1600 contiguous nucleotides, from about 75 to about 1500 contiguous nucleotides, from about 100 to about 1400 nucleotides, from about 150 to about 1300 contiguous nucleotides, from about 150 to about 1200 contiguous nucleotides, from about 175 to about 1100 contiguous nucleotides, or from about 200 to about 1000 contiguous nucleotides from a cytochrome P450 polynucleotide as disclosed herein.

In one aspect, fragments of a cytochrome P450 polynucleotide comprise a polynucleotide sequence containing the nucleotides from about position 700 to about position 1250 of a cytochrome P450 coding sequence. In another aspect, fragments of a cytochrome P450 polynucleotide comprise a polynucleotide sequence containing the nucleotides from about position 715 to about position 1210, or from about position 717 to about position 1207 of a cytochrome P450 coding sequence disclosed herein.

In other embodiments of the invention, fragments of a cytochrome P450 polynucleotide comprise a polynucleotide sequence containing the nucleotides from about position 265 to about position 625 of a cytochrome P450 coding sequence disclosed herein, or a complement thereof. In some of these embodiments, the fragments of a cytochrome P450 coding sequence disclosed herein comprise the nucleotides corresponding to about position 297 to about position 594 of the P450 coding sequence set forth in SEQ ID NO:3 or SEQ ID NO:5, or a complement thereof.

In yet other embodiments of the invention, fragments of a cytochrome P450 polynucleotide comprise a polynucleotide sequence containing the nucleotides from about position 1420 to about position 1580 of a cytochrome P450 coding sequence disclosed herein, or a complement thereof. In some of these embodiments, the fragments of a cytochrome P450 coding sequence disclosed herein comprise the nucleotides corresponding to about position 1453 to about position 1551 of the P450 coding sequence set forth in SEQ ID NO:1, or a complement thereof.

Variants of the disclosed polynucleotides and polypeptides encoded thereby are also encompassed by the present invention. Such naturally occurring variants include those variants that share substantial sequence identity to the disclosed cytochrome P450 polynucleotides and polypeptides disclosed herein as defined herein below. The compositions and methods of the invention can be used to target expression or function of any naturally occurring cytochrome P450 that shares substantial sequence identity to the disclosed cytochrome P450 polypeptides and which possesses the relevant cytochrome P450 activity, i.e., involvement in the metabolic conversion of nicotine to nornicotine in plants. Such variants may result from, for example, genetic polymorphism or from human manipulation as occurs with breeding and selection. Biologically active variants of a cytochrome P450 protein of the invention, for example, variants of the polypeptide set forth in SEQ ID NO:2, 4, 6, 8, 10, or 12, will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein, and are characterized by their functional involvement in the metabolic conversion of nicotine to nornicotine in plants. A biologically active variant of a protein of the invention may differ from that protein by as few as 1-15 amino acid residues, as few as 10, as few as 9, as few as 8, as few as 7, as few as 6, as few as 5, as few as 4, as few as 3, as few as 2, or as few as 1 amino acid residue.

Variants of a particular polynucleotide of the present invention include those naturally occurring polynucleotides that encode a cytochrome P450 polypeptide that is involved in the metabolic conversion of nicotine to nornicotine in plants. Such polynucleotide variants can comprise a deletion and/or addition of one or more nucleotides at one or more sites within the native polynucleotide disclosed herein and/or a substitution of one or more nucleotides at one or more sites in the native polynucleotide. Because of the degeneracy of the genetic code, conservative variants for polynucleotides include those sequences that encode the amino acid sequence of one of the cytochrome P450 polypeptides of the invention. Naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still share substantial sequence identity to the naturally occurring sequences disclosed herein, and thus can be used in the methods of the invention to inhibit the expression or function of a cytochrome P450 that is involved in the metabolic conversion of nicotine to nornicotine, including the cytochrome P450 polypeptides set forth in SEQ ID NOS:2, 4, 6, and 8, and polypeptides comprising the sequence set forth in SEQ ID NO:10 or 12. Generally, variants of a particular polynucleotide of the invention, for example, the sequence set forth in SEQ ID NO:1, 3, 5, 7, 9, or 11, will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the present invention (also referred to as the reference polynucleotide) can also be evaluated by comparison of the percent sequence identity between the polypeptide encoded by the reference polynucleotide and the polypeptide encoded by a variant polynucleotide. For example, isolated polynucleotides encoding a polypeptide with a particular percent sequence identity to the full-length polypeptide of SEQ ID NO:2, 4, 6, or 8, or the partial-length polypeptide encoded by SEQ ID NO:9 or 11 are disclosed. Such polynucleotides can be used in the methods of the present invention to target expression of cytochrome P450 polypeptides involved in the metabolic conversion of nicotine to nornicotine in plants, particularly tobacco plants, thereby inhibiting accumulation of nornicotine and its metabolite N'-nitrosonornicotine in the stems and leaves of the genetically modified plant. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity. In one aspect, a variant polypeptide of the present invention includes a polypeptide having a tryptophan at position 330 or an isoleucine at position 274 of the cytochrome P450 polypeptide, or both a tryptophan at position 330 and an isoleucine at position 274.

Furthermore, the polynucleotides of the invention can be used to isolate corresponding cytochrome P450 sequences from other organisms, particularly other plants, more particularly other members of the *Nicotiana* genus. PCR, hybridization, and other like methods can be used to identify such sequences based on their sequence homology to the sequences set forth herein. Sequences isolated based on their sequence identity to the nucleotide sequences set forth herein or to variants and fragments thereof are encompassed by the present invention. Such sequences include sequences that are orthologs of the disclosed sequences.

According to the present invention, "orthologs" are genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for a cytochrome P450 polypeptide that is involved in the nicotine-to-nornicotine metabolic conversion and which hybridize under stringent conditions to the cytochrome P450 sequences disclosed herein, or to variants or fragments thereof, are encompassed by the present invention. Such sequences can be used in the methods of the present invention to inhibit expression of cytochrome P450 polypeptides that are involved in the metabolic conversion of nicotine to nornicotine in plants.

Using PCR, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially mismatched primers, and the like.

Hybridization techniques involve the use of all or part of a known polynucleotide as a probe that selectively hybridizes to other corresponding polynucleotides present in a population of cloned genomic DNA fragments or cDNA fragments (i.e., genomic or cDNA libraries) from a chosen organism. Hybridization may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In a specific embodiment, stringency conditions include hybridization in a solution containing 5×SSC, 0.5% SDS, 5×Denhardt's, 0.45 µg/µl Poly A RNA, 0.45 µg/µl calf thymus DNA and 50% formamide at 42° C., and at least one post-hybridization wash in a solution comprising from about 0.01× SSC to about 1×SSC. The duration of hybridization is from about 14 to about 16 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 11° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 110° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Hybridization probes may be genomic DNA fragments, cDNA fragments, RNA fragments, or other oligonucleotides, and may be labeled with a detectable group such as $^{32}$P, or any other detectable marker. For example, probes for hybridization can be made by labeling synthetic oligonucleotides based on the cytochrome P450 polynucleotides sequences of the present invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the cytochrome P450 polynucleotide sequences disclosed herein, or one or more portions thereof, may be used as probes capable of specifically hybridizing to corresponding cytochrome P450 polynucleotides and messenger RNAs. To achieve specific hybridization under a variety of conditions, such probes include sequences that are unique among cytochrome P450 polynucleotide sequences, including upstream regions 5' to the coding sequence and downstream regions 3' to the coding sequence, and are optimally at least about 10 nucleotides in length, and most optimally at least about 20 nucleotides in length. Such probes may be used to amplify corresponding cytochrome P450 polynucleotides. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

As used herein, with respect to the sequence relationships between two or more polynucleotides or polypeptides, the term "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, the term "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local-alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used (See www.ncbi.nlm.nih.gov). Alignment may also be performed manually by inspection.

The sequence identity/similarity values provided herein were calculated using the BLASTX (Altschul et al. (1997) supra), Clustal W (Higgins et al. (1994) *Nucleic Acids Res.* 22: 4673-4680), and GAP (University of Wisconsin Genetic Computing Group software package) algorithms using default parameters. The present invention also encompasses the use of any equivalent program thereof for the analysis and comparison of nucleic acid and protein sequences. By "equivalent program" is intended any sequence comparison program that, for any two sequences in question, generates an alignment having identical nucleotide or amino acid residue matches and an identical percent sequence identity when compared to the corresponding alignment generated by BLASTX, Clustal W, or GAP.

For purposes of the foregoing discussion of variant nucleotide and polypeptide sequences encompassed by the present invention, the term "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

The term "percentage of sequence identity" as used herein means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

When any two polypeptide sequences are optimally aligned for comparison, it is recognized that residues appearing opposite of one another within the alignment occupy positions within their respective polypeptides that correspond to one another. Such positions are referred to herein as "corresponding positions" and the residues residing at corresponding positions are referred to as "corresponding residues" or residues that "correspond" to one another. Thus, for example, where a polypeptide of interest is optimally aligned to a reference polypeptide sequence having, for example, 10 residues, the residue within the polypeptide of interest appearing opposite residue 5 of the reference sequence is referred to as the "residue at the position corresponding to residue 5" of the reference sequence.

In like manner, when any two polynucleotide sequences are optimally aligned for comparison, it is recognized that the nucleotides appearing opposite of one another within the alignment occupy positions within their respective polynucleotide positions that correspond to one another. Such positions are referred to herein as "corresponding positions" and the nucleotides residing at corresponding positions are referred to as "corresponding nucleotides" or nucleotides that "correspond" to one another. Thus, for example, where a polynucleotide of interest is optimally aligned to a reference polynucleotide sequence having, for example, 300 nucleotides, the nucleotide within the polynucleotide of interest appearing opposite nucleotide 275 of the reference sequence is referred to as the "nucleotide at the position corresponding to nucleotide 275" of the reference sequence.

Where a region of nucleotides is being compared between a polynucleotide of interest and a reference polynucleotide, the nucleotides within these regions are said to "correspond" to one another. Thus, for example, where a region of a reference polynucleotide sequence, for example, the polynucleotide sequence set forth in SEQ ID NO:5, resides from nucleotide position 265 to nucleotide position 625 of the reference polynucleotide, and this region of nucleotides is being compared to the corresponding region of nucleotides within an optimally aligned polynucleotide sequence of interest, the nucleotides within the corresponding region of the polynucleotide of interest are referred to herein as "a region" of the polynucleotide of interest that "corresponds to nucleotide position 265 to nucleotide position 625" of the reference sequence, in this case, SEQ ID NO:5.

Cytochrome P450 polynucleotide and polypeptide sequences can be identified using the sequences provided herein. Such methods include obtaining a polynucleotide or polypeptide sequence at least 80%, 85%, 90%, 95%, 98%, 99% sequence identity with the polynucleotide sequence of SEQ ID NO 1, 3, 5, 7, 9, or 11 or a complement or fragment thereof, or a polypeptide sequence of SEQ ID NO:2, 4, 6, 7, 10, or 12. In one embodiment, the identified sequence contains or encodes for a tryptophan residue at position 330 and an isoleucine residue at position 274.

In this manner, one aspect of the present invention is directed to a method of screening for a nicotine demethylase sequence. This method comprises obtaining a nucleic acid sequence that has greater than about 90% sequence identity with SEQ ID NO:3 or SEQ ID NO:5; and identifying within this nucleic acid sequence a codon sequence encoding for a tryptophan residue at position 330 of the polypeptide encoded by the nucleic acid sequence. In some embodiments, this nucleic acid sequence also encodes an isoleucine at position 274 of the encoded polypeptide. Any suitable method known in the art can be used to identify the codon sequence encoding the tryptophan or isoleucine residue. In one embodiment, the codon sequence is identified by a method selected from the group consisting of identifying a single nucleotide polymorphism and RT-PCR. In some embodiments of this aspect of the invention, the screening method identifies a nicotine demethylase that converts nicotine to nornicotine at a rate that is at least about 5-fold greater than the conversion rate of the nicotine demethylase encoded by SEQ ID NO:3 (polypeptide set forth in SEQ ID NO:4) or SEQ ID NO:5 (polypeptide set forth in SEQ ID NO:6). In particular embodiments, the nicotine demethylase identified with this screening method has a conversion rate that is at least about 8-fold greater than the conversion rate of the nicotine demethylase encoded by SEQ ID NO:3 or SEQ ID NO:5.

In another aspect, the present invention provides a method for screening for a nicotine demethylase having an isoleucine at position 274 or a tryptophan at position 329 of the polypeptide. This method comprises obtaining a nucleic acid sequence that has greater than about 90% sequence identity with SEQ ID NO:3 or SEQ ID NO:5; and identifying a first codon sequence encoding for an isoleucine residue at position 274 of the encoded polypeptide or a second codon sequence encoding a tryptophan residue at position 330 of the encoded polypeptide. As noted above, any suitable method known to those of skill in the art can be used to identify these codons. In one embodiment, either or both of the first and second codons are identified by a method selected from the group consisting of identifying a single nucleotide polymorphism and RT-PCR. In some embodiments of this aspect of the invention, the screening method identifies a nicotine demethylase that converts nicotine to nornicotine at a rate that is at least about 5-fold greater than the conversion rate of the nicotine demethylase encoded by SEQ ID NO:3 (polypeptide set forth in SEQ ID NO:4) or SEQ ID NO:5 (polypeptide set forth in SEQ ID NO:6). In particular embodiments, the nicotine demethylase identified with this screening method has a conversion rate that is at least about 8-fold greater than the conversion rate of the nicotine demethylase encoded by SEQ ID NO:3 or SEQ ID NO:5.

The present invention also provides transgenic plant cells, plants, and seed comprising a nucleic acid molecule having a promoter functional in a plant cell and a nucleic acid sequence encoding a nicotine demethylase having an isoleucine residue at position 274 and a tryptophan residue at position 330. In some embodiments, the nucleic acid sequence encoding this nicotine demethylase is derived from a sequence selected from the group consisting of SEQ ID NO:3, SEQ ID NO:5, and SEQ ID NO:7. These transgenic plant cells, plants, and seed include, but are not limited to, *Nicotiana* plant cells, *Nicotiana* plants, and seed of *Nicotiana* plants. In some embodiments, the *Nicotiana* plant cells, *Nicotiana* plants, and seed of *Nicotiana* plants are from converter *Nicotiana* plants.

Expression Cassettes for Use in the Methods of the Invention

Compositions of the present invention further include expression cassettes comprising inhibitory sequences capable of inhibiting expression or function of a cytochrome P450 polypeptide involved in the conversion of nicotine to nornicotine in a *Nicotiana* plant or plant part thereof, where the inhibitory sequences are operably linked to a promoter that is functional in a plant cell. In this manner, expression cassettes comprising all or part of the sequence set forth in SEQ ID NO:1, 3, 5, 7, 9, or 11, a complement or fragment thereof, or sequences sharing substantial sequence identity to SEQ ID NO:1, 3, 5, 7, 9, 11, or a complement or fragment thereof, operably linked to a promoter that is functional in a plant cell are constructed for use in the gene-silencing methods of the present invention described herein below. Such sequences are referred to herein as "inhibitory sequences" or "inhibitory polynucleotide sequences" as they are capable of being expressed as an RNA molecule that inhibits expression (i.e, transcription and/or translation) of the target cytochrome P450 polypeptide, for example, the polypeptide set forth in SEQ ID NO:2, 4, 6, or 8 and variants thereof, or a polypeptide comprising the sequence set forth in SEQ ID NO:10 or 12 and variants thereof, where the variant polypeptides have substantial sequence identity to these disclosed cytochrome P450 polypeptides and are involved in the metabolic conversion of nicotine to nornicotine in a plant.

As noted above, such inhibitory sequences include fragment sequences of the target cytochrome P450 polynucleotides. For example, a fragment sequence can include any portion of the cytochrome P450 sequence, including coding and non-coding sequence (e.g., 5' UTR, intron, and 3' UTR sequences), and can include fragments of between about 20 and about 400 nucleotides, between about 50 and about 400 nucleotides, between about 100 and about 400 nucleotides, between about 125 and about 325 nucleotides, between about 125 and about 300 nucleotides, or between about 125 and about 275 nucleotides.

In this manner, such inhibitory sequences include, but are not limited, sequences that comprise a fragment of a cytochrome P450 polynucleotide sequence ranging from at least about 20 nucleotides, about 50 nucleotides, about 70 nucleotides, about 100 nucleotides, about 150 nucleotides, about 200 nucleotides, about 250 nucleotides, about 300 nucleotides, about 350 nucleotides, and up to the full-length polynucleotide encoding the proteins of the invention, depending upon the desired outcome. In one aspect, the inhibitory sequences comprise a fragment of a cytochrome P450 polynucleotide sequence that is between about 50 and about 400 nucleotides, between about 50 and about 350 nucleotides, between about 70 and about 350 nucleotides, between about 90 and about 325 nucleotides, between about 90 and about 300 nucleotides, between about 90 and about 275 nucleotides, between about 100 and about 400 nucleotides, between about 100 and about 350 nucleotides, between about 100 and about 325 nucleotides, between about 100 and about 300 nucleotides, between about 125 and about 300 nucleotides, or between about 125 and about 275 nucleotides in length. In some embodiments, the inhibitory sequences comprise a fragment of a cytochrome P450 polynucleotide sequence that is about 50, about 60, about 70, about 80, about 90, about 100, about 125, about 150, about 175, about 200, about 225, about 250, about 275, about 300, about 325, about 350, about 400 nucleotides in length, and other such values between about 50 and about 400 nucleotides. It is recognized that the inhibitory sequence can also comprise a sequence that is complementary to all or a part of the fragment of the cytochrome P450 polynucleotide sequence.

In one such embodiment, the inhibitory sequences comprise a fragment of a cytochrome P450 polynucleotide of the invention that is about 90 bp to about 110 bp in length, including 90, 91, 92, 93, 94, 95, 96, 97, 98, 99, 100, 101, 102, 103, 104, 105, 106, 107, 108, 109, and 110 bp in length, and can also comprise a sequence that is complementary to all or a part of the fragment sequence. In another such embodiment, a fragment of a cytochrome P450 polynucleotide of the invention is about 290 to about 310 bp in length, including 290, 291, 292, 293, 294, 295, 296, 297, 298, 299, 300, 301, 302, 303, 304, 305, 306, 307, 308, 309, and 310 bp in length, and can also comprise a sequence that is complementary to all or a part of the fragment sequence.

In other embodiments of the invention, the inhibitory sequence within an expression cassette of the invention comprises a polynucleotide sequence containing the nucleotides from about position 265 to about position 625 of a cytochrome P450 coding sequence disclosed herein and sequence that is fully or partially complementary thereto. In some of these embodiments, the inhibitory sequence comprises the nucleotides corresponding to about position 297 to about position 594 of the P450 coding sequence set forth in SEQ ID NO:3 or SEQ ID NO:5 and a sequence that is fully or partially complementary thereto. In preferred embodiments, such inhibitory sequences are expressed as a hairpin RNA as described herein below.

In yet other embodiments of the invention, the inhibitory sequence within an expression cassette of the invention comprises a polynucleotide sequence containing the nucleotides from about position 1420 to about position 1580 of a cytochrome P450 coding sequence disclosed herein and a sequence that is fully or partially complementary thereto. In some of these embodiments, the inhibitory sequence comprises the nucleotides corresponding to about position 1453 to about position 1551 of the P450 coding sequence set forth in SEQ ID NO:1 and a sequence that is fully or partially complementary thereto. In preferred embodiments, such inhibitory sequences are expressed as a hairpin RNA as described herein below.

It is recognized that expression cassettes of the present invention encompass constructs in which a desired nucleic acid sequence is operably linked to a promoter that is functional in a plant cell, particularly in the cell of a *Nicotiana* plant. By "promoter" is intended a regulatory region of DNA usually comprising a TATA box capable of directing RNA polymerase II to initiate RNA synthesis at the appropriate transcription initiation site for a particular polynucleotide sequence. A promoter may additionally comprise other recognition sequences generally positioned upstream or 5' to the TATA box, referred to as upstream promoter elements, which influence the transcription initiation rate. It is also recognized that expression cassettes of the present invention encompass additional domains that modulate the level of expression, the developmental timing of expression, or tissue type that expression occurs in (e.g., Australian Patent No. AU-A-77751/94 and U.S. Pat. Nos. 5,466,785 and 5,635,618). By "functional" is intended the promoter, when operably linked to an inhibitory sequence encoding an inhibitory nucleotide molecule (for example, a hairpin RNA, double-stranded RNA, miRNA polynucleotide, and the like), the promoter is capable of initiating transcription of the operably linked inhibitory sequence such that the inhibitory nucleotide molecule is expressed. The promoters can be selected based on the desired outcome. The nucleic acids can be combined with constitutive, tissue-preferred, or other promoters for expression in plants.

An expression cassette of the present invention may also contain at least one additional gene to be cotransformed into the plant. Alternatively, the additional gene(s) can be provided on multiple expression cassettes. Such an expression cassette is provided with a plurality of restriction sites and/or recombination sites for insertion of the cytochrome P450 inhibitory polynucleotide sequence to be under the transcriptional regulation of the regulatory regions. The expression cassette may additionally contain selectable marker genes.

In this manner, an expression cassette of the present invention includes a transcriptional and translational initiation region (i.e., a promoter) in the 5'-3' direction of transcription, an inhibitory sequence as described elsewhere herein, and a transcriptional and translational termination region (i.e., termination region) functional in a plant cell. The regulatory regions (i.e., promoters, transcriptional regulatory regions, and translational termination regions) and/or the inhibitory sequence of the invention may be native/analogous to the host cell or to each other. Alternatively, the regulatory regions and/or the inhibitory sequence of the invention may be heterologous to the host cell or to each other. While heterologous promoters can be used to express the inhibitory sequences of the invention, native promoter sequences may also be used.

The termination region may be native with the transcriptional initiation region, may be native with the operably linked inhibitory sequence of the invention, may be native with the plant host, or may be derived from another source (i.e., foreign or heterologous to the promoter, the inhibitory sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Expression cassettes of the present invention may additionally contain 5' leader sequences that can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized.

In preparing the expression cassette, DNA fragments of the invention may be manipulated so as to provide for the DNA sequences in the proper orientation and, as appropriate, in the proper reading frame. Adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassettes of the present invention can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Rouwendal et al. (1997) *Plant Mo. Biol.* 33:989-999; Su et al. (2004) *Biotechnol Bioeng* 85:610-9 and Fetter et al. (2004) *Plant Cell* 16:215-28), cyan florescent protein (CYP) (Bolte et al. (2004) *J Cell Science* 117:943-54 and Kato et al. (2002) *Plant Physiol* 129:913-42), and yellow fluorescent protein (PhiYFP™ from Evrogen, see, Bolte et al. (2004) *J Cell Science* 117:943-954). For additional selectable markers, see generally, Yarranton (1992) *Curr. Opin. Biotech.* 3:506-511; Christopherson et al. (1992) *Proc. Natl. Acad Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad Sci. USA* 86:2549-2553; Deuschle et al. (1990) *Science* 248:480-483; Gossen (1993) Ph.D. Thesis, University of Heidelberg; Reines et al. (1993) *Proc. Natl. Acad Sci. USA* 90:1917-1921; Labowi et al. (1990) *Mol. Cell. Biol.* 10:3343-3356; Zambretti et al. (1992) *Proc. Natl. Acad Sci. USA* 89:3952-3956; Baim et al. (1991) *Proc. Natl. Acad Sci. USA* 88:5072-5076; Wyborski et al. (1991) *Nucleic Acids Res.* 19:4647-4653; Hillenand-Wissman (1989) *Topics Mol. Struc. Biol.* 10: 143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology, Vol.* 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

A number of promoters can be used in the practice of the invention. Of particular interest are constitutive promoters, inducible promoters, particularly chemical-inducible promoters, and tissue-preferred promoters, particularly leaf-preferred promoters.

Chemical-inducible promoters can be used to inhibit the expression of a cytochrome P450 that is involved in the metabolic conversion of nicotine to nornicotine in a plant through the application of an exogenous chemical regulator. Chemical-inducible promoters are known in the art and include, but are not limited to, the tobacco PR-1a promoter, which is activated by salicylic acid. Other chemical-inducible promoters of interest include steroid-responsive promoters (see, for example, Schena et al. (1991) *Proc. Natl. Acad. Sci. USA* 88:10421-10425 and McNellis et al. (1998) *Plant J.* 14(2):247-257) and tetracycline-inducible promoters (see, for example, Gatz et al. (1991) *Mol. Gen. Genet.* 227:229-237, and U.S. Pat. Nos. 5,814,618 and 5,789,156), herein incorporated by reference.

Constitutive promoters include, for example, the core promoter of the Rsyn7 promoter and other constitutive promoters disclosed in U.S. Pat. No. 6,072,050; the core CaMV 35S promoter (Odell et al. (1985) *Nature* 313:810-812); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target expression of an inhibitory polynucleotide sequence of the present invention within a particular plant tissue. Tissue-preferred promoters include Yamamoto et al. (1997) *Plant J* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505.

Of particular interest are leaf-preferred promoters that provide for expression predominately in leaf tissues. See, for example, Yamamoto et al. (1997) *Plant J* 12(2):255-265; Kwon et al. (1994) *Plant Physiol.* 105:357-67; Yamamoto et al. (1994) *Plant Cell Physiol.* 35(5):773-778; Gotor et al. (1993) *Plant J* 3:509-18; Orozco et al. (1993) *Plant Mol. Biol.* 23(6):1129-1138; Baszczynski et al. (1988) *Nucl. Acid Res.* 16:4732; Mitra et al. (1994) *Plant Molecular Biology* 26:35-93; Kayaya et al. (1995) *Molecular and General Genetics* 248:668-674; and Matsuoka et al. (1993) *Proc. Natl. Acad. Sci. USA* 90(20):9586-9590. Senecence-regulated promoters are also of use, such as SAM22 (Crowell et al. (1992) *Plant Mol. Biol.* 18:459-466); SAG12 (Lohman et al. (1994) *Physiol. Plant.* 92:322-328; Wingler et al. (1998) *Plant Physiol.* 116:329-335); SAG 13 (Gan and Amasino (1997) *Plant Physiol.* 113:313-319; SAG 15 (Gan (1995) "Molecular Characterization and Genetic Manipulation of Plant Senescence," Ph.D. Thesis, University of Wisconsin, Madison); SEN1 (Oh et al. (1996) *Plant Mol. Biol.* 30:739-754; promoter of a senescence-specific gene for expression of IPT (Gan and Amasino 91995) *Science* 270:1986-1988); and the like (see, for example, Or: et al. (1999) *Plant Cell* 11:1073-1080 and McCabe et al. (2001) *Plant Physiol.* 127:505-516).

Methods for Inhibiting Expression or Function of a Cytochrome P450 Involved in the Conversion of Nicotine to Nornicotine Methods of reducing the concentration, content, and/or activity of a cytochrome P450 polypeptide of the present invention in a *Nicotiana* plant or plant part, particularly the leaf tissue, are provided. Many methods may be used, alone or in combination, to reduce or eliminate the activity of a cytochrome P450 polypeptide of the present invention. In addition, combinations of methods may be employed to reduce or eliminate the activity of two or more different cytochrome P450 polypeptides.

In accordance with the present invention, the expression of a cytochrome P450 polypeptide of the present invention is inhibited if the protein level of the cytochrome P450 polypeptide is statistically lower than the protein level of the same cytochrome P450 polypeptide in a plant that has not been genetically modified or mutagenized to inhibit the expression of that cytochrome P450 polypeptide, and where these plants have been cultured and harvested using the same protocols. In particular embodiments of the invention, the protein level of the cytochrome P450 polypeptide in a modified plant according to the invention is less than 95%, less than 90%, less than 80%, less than 70%, less than 60%, less than 50%, less than 40%, less than 30%, less than 20%, less than 10%, less than 5%, less than 4%, less than 3%, less than 2%, or less than 1% of the protein level of the same cytochrome P450 polypeptide in a plant that is not a mutant or that has not been genetically modified to inhibit the expression of that cytochrome P450 polypeptide and which has been cultured and harvested using the same protocols. The expression level of the cytochrome P450 polypeptide may be measured directly, for example, by assaying for the level of the cytochrome P450 transcript or cytochrome P450 polypeptide expressed in the *Nicotiana* plant or plant part, or indirectly, for example, by measuring the conversion of nicotine to nornicotine in the *Nicotiana* plant or plant part. Methods for monitoring the expression level of a protein are known in the art, and include, but are not limited to, Northern blot analysis as discussed in the examples herein below. Methods for determining the activity of the targeted cytochrome P450 polypeptide in converting nicotine to nornicotine are described elsewhere herein below, and include, but are not limited to, alkaloid analysis using gas chromatography, for example the procedures described in the examples herein below.

In other embodiments of the invention, the activity of one or more cytochrome P450 polypeptides is reduced or eliminated by transforming a plant or plant part with an expression cassette comprising a polynucleotide encoding a polypeptide that inhibits the activity of one or more cytochrome P450 polypeptides of the present invention. The activity of a cytochrome P450 polypeptide in converting nicotine to nornicotine in a *Nicotiana* plant or plant part is inhibited according to the present invention if this conversion activity is statistically lower than conversion activity of the same cytochrome P450 polypeptide in a *Nicotiana* plant or plant part that has not been genetically modified to inhibit the conversion activity of that cytochrome P450 polypeptide and which has been cultured and harvested using the same protocols. In particular embodiments, activity of a cytochrome P450 polypeptide in converting nicotine to nornicotine in a modified *Nicotiana* plant or plant part according to the invention is inhibited if the activity is less than 95%, less than 90%, less than 80%, less than 70%, less than 60%, less than 50%, less than 40%, less than 30%, less than 20%, less than 10%, less than 5%, less than 4%, less than 3%, less than 2%, or less than 1% of the conversion activity of the same cytochrome P450 polypeptide in a *Nicotiana* plant that that has not been genetically modified to inhibit the expression of that cytochrome P450 polypeptide and which has been cultured and harvested using the same protocols. The activity of a cytochrome P450 polypeptide in converting nicotine to nornicotine in a *Nicotiana* plant or plant part is eliminated according to the invention when it is not detectable by the assay methods described elsewhere herein. Methods of determining the activity of a cytochrome P450 polypeptide in converting nicotine to nornicotine in a *Nicotiana* plant or plant part are described elsewhere herein, and include the alkaloid analyses using gas chromatography disclosed in the examples herein below.

In specific embodiments, a cytochrome P450 inhibitory polynucleotide sequence described herein is introduced into a *Nicotiana* plant or plant part. Subsequently, a *Nicotiana* plant or plant part having the introduced inhibitory polynucleotide sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

In some embodiments, a transformed tobacco plant containing a cytochrome P450 inhibitory polynucleotide sequence described herein has a reduced level of conversion of nicotine to nornicotine. In particular embodiments, conversion of nicotine to nornicotine in a transformed tobacco plant or plant part according to the invention is less than 95%, less than 90%, less than 80% less than 70%, less than 60%, less than 50%, less than 40%, less than 30%, less than 20% less than 10%, less than 5%, less than 4%, less than 3%, less than 2%, or less than 1% of the conversion in a tobacco plant that that has not been genetically modified to inhibit the expression of that cytochrome P450 polypeptide and which has been cultured and harvested using the same protocols. In some embodiments, the transformed tobacco plant is a converter tobacco plant. In some embodiments, the transformed tobacco plant has a conversion rate lower than the rate observed in commercial nonconverter tobacco plants.

It is also recognized that the level and/or activity of the polypeptide may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

It is therefore recognized that methods of the present invention do not depend on the incorporation of the entire cytochrome P450 inhibitory polynucleotide into the genome, only that the *Nicotiana* plant or plant part thereof is altered as a result of the introduction of this inhibitory polynucleotide into a cell. In one embodiment of the invention, the genome may be altered following the introduction of the cytochrome P450 inhibitory polynucleotide into a cell. For example, the inhibitory polynucleotide, or any part thereof, may incorporate into the genome of the plant. Alterations to the genome include, but are not limited to, additions, deletions, and substitutions of nucleotides into the genome. While the methods of the present invention do not depend on additions, deletions, and substitutions of any particular number of nucleotides, it is recognized that such additions, deletions, or substitutions comprise at least one nucleotide.

It is further recognized that reducing the level and/or activity of a cytochrome P450 sequence of the present invention can be performed to elicit the effects of the sequence only during certain developmental stages and to switch the effect off in other stages where expression is no longer desirable.

Control of cytochrome P450 expression can be obtained via the use of inducible or tissue-preferred promoters. Alternatively, the gene could be inverted or deleted using site-specific recombinases, transposes or recombination systems, which would also turn on or off expression of the cytochrome P450 sequence.

According to the present invention, changes in levels, ratios, activity, or distribution of cytochrome P450 polypeptides of the present invention, or changes in *Nicotiana* plant or plant part phenotype, particularly reduced accumulation of nornicotine and its carcinogenic metabolite, NNN, could be measured by comparing a subject plant or plant part to a control plant or plant part, where the subject plant or plant part and the control plant or plant part have been cultured and/or harvested using the same protocols. As used herein, a subject plant or plant part is one in which genetic alteration, such as transformation, has been affected as to the cytochrome P450 polypeptide of interest, or is a *Nicotiana* plant or plant part that is descended from a *Nicotiana* plant or plant part so altered and which comprises the alteration. A control plant or plant part provides a reference point for measuring changes in phenotype of the subject plant or plant part.

The measurement of changes in phenotype can be measured at any time in a plant or plant part, including during plant development, senescence, or after curing. In other embodiments, the measurement of changes in phenotype can be measured in plants grown under any conditions, including from plants grown in a growth chamber, greenhouse, or in a field. In one embodiment, changes in phenotype can be measured by determining the nicotine to nornicotine conversion rate. In a preferred embodiment, conversion can be measured by dividing the percentage of nornicotine (as a percentage of the total tissue weight) by the sum of the percentage nicotine and nornicotine (as percentages of the total tissue weight) and multiplying by 100.

According to the present invention, a control plant or plant part may comprise a wild-type *Nicotiana* plant or plant part, i.e., of the same genotype as the starting material for the genetic alteration that resulted in the subject plant or plant part. A control plant or plant part may also comprise a *Nicotiana* plant or plant part of the same genotype as the starting material but that has been transformed with a null construct (i.e., with a construct that has no known effect on the trait of interest, such as a construct comprising a selectable marker gene). Alternatively, a control plant or plant part may comprise a *Nicotiana* plant or plant part that is a non-transformed segregant among progeny of a subject plant or plant part, or a *Nicotiana* plant or plant part genetically identical to the subject plant or plant part but that is not exposed to conditions or stimuli that would induce suppression of the cytochrome P450 gene of interest. Finally, a control plant or plant part may comprise the subject plant or plant part itself under conditions in which the cytochrome P450 inhibitory sequence is not expressed. In all such cases, the subject plant or plant part and the control plant or plant part are cultured and harvested using the same protocols.

As described elsewhere herein, methods are provided to reduce or eliminate the activity and/or concentration of a cytochrome P450 polypeptide of the present invention by introducing into a *Nicotiana* plant or plant part a cytochrome P450 inhibitory polynucleotide sequence that is capable of inhibiting expression or function of a cytochrome P450 polypeptide that is involved in the metabolic conversion of nicotine to nornicotine. In some embodiments, the inhibitory sequence is introduced by transformation of the plant or plant part, such as a plant cell, with an expression cassette that expresses a polynucleotide that inhibits the expression of the cytochrome P450 polypeptide. The polynucleotide may inhibit the expression of a cytochrome P450 polypeptide directly, by preventing translation of the cytochrome P450 polypeptide messenger RNA, or indirectly, by encoding a polypeptide that inhibits the transcription or translation of an cytochrome P450 polypeptide gene encoding a cytochrome P450 polypeptide. Methods for inhibiting or eliminating the expression of a gene product in a plant are well known in the art, and any such method may be used in the present invention to inhibit the expression of cytochrome P450 polypeptides.

In other embodiments, the activity of a cytochrome P450 polypeptide of the present invention may be reduced or eliminated by disrupting the gene encoding the cytochrome P450 polypeptide. The invention encompasses mutagenized plants that carry mutations in cytochrome P450 genes, where the mutations reduce expression of the cytochrome P450 gene or inhibit the activity of an encoded cytochrome P450 polypeptide of the present invention.

In some embodiments of the present invention, a *Nicotiana* plant or plant part is transformed with an expression cassette that is capable of expressing a polynucleotide that inhibits the expression of a cytochrome P450 sequence. Such methods may include the use of sense suppression/cosuppression, antisense suppression, double-stranded RNA (dsRNA) interference, hairpin RNA interference and intron-containing hairpin RNA interference, amplicon-mediated interference, ribozymes, and small interfering RNA or micro RNA.

For cosuppression, an expression cassette is designed to express an RNA molecule corresponding to all or part of a messenger RNA encoding a cytochrome P450 polypeptide of interest (for example, a cytochrome P450 polypeptide comprising the sequence set forth in SEQ ID NO:2, 4, 6, 8, 10, or 12 or a sequence having substantial sequence identity to SEQ ID NO:2, 4, 6, 8, 10, or 12) in the "sense" orientation. Over expression of the RNA molecule can result in reduced expression of the native gene. Multiple plant lines transformed with the cosuppression expression cassette are then screened to identify those that show the greatest inhibition of cytochrome P450 polypeptide expression.

The polynucleotide used for cosuppression may correspond to all or part of the sequence encoding a cytochrome P450 polypeptide or the present invention, all or part of the 5' and/or 3' untranslated region of a cytochrome P450 polypeptide transcript, or all or part of both the coding sequence and the untranslated regions of a transcript encoding a cytochrome P450 polypeptide. In some embodiments where the polynucleotide comprises all or part of the coding region for a cytochrome P450 polypeptide of the present invention, the expression cassette is designed to eliminate the start codon of the polynucleotide so that no protein product will be transcribed.

Cosuppression may be used to inhibit the expression of plant genes to produce plants having undetectable protein levels for the proteins encoded by these genes or may also be used to inhibit the expression of multiple proteins in the same plant (e.g., Broin et al. (2002) *Plant Cell* 14:1417-1432; U.S. Pat. No. 5,942,657). Methods for using cosuppression to inhibit the expression of endogenous genes in plants are described in Flavell et al. (1994) *Proc. Natl. Acad. Sci. USA* 91:3490-3496; Jorgensen et al. (1996) *Plant Mol. Biol.* 31:957-973; Johansen and Carrington (2001) *Plant Physiol.* 126:930-938; Broin et al. (2002) *Plant Cell* 14:1417-1432; Stoutjesdijk et al (2002) *Plant Physiol.* 129:1723-1731; Yu et al. (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity (e.g., U.S. Pat. Nos. 5,283,184 and 5,034,323; herein incorporated by reference).

In some embodiments of the invention, inhibition of the expression of the cytochrome P450 polypeptide of the present invention may be obtained by antisense suppression. For antisense suppression, the expression cassette is designed to express an RNA molecule complementary to all or part of a messenger RNA encoding the cytochrome P450 polypeptide. Over expression of the antisense RNA molecule can result in reduced expression of the native gene. Accordingly, multiple plant lines transformed with the antisense suppression expression cassette are screened to identify those that show the greatest inhibition of cytochrome P450 polypeptide expression.

The polynucleotide for use in antisense suppression may correspond to all or part of the complement of the sequence encoding the cytochrome P450 polypeptide, all or part of the complement of the 5' and/or 3' untranslated region of the cytochrome P450 polypeptide transcript, or all or part of the complement of both the coding sequence and the untranslated regions of a transcript encoding the cytochrome P450 polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant (e.g., U.S. Pat. No. 5,942,657). Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence for the target cytochrome P450 sequence. Alternatively, separate expression cassettes may be used for the sense and antisense sequences. Multiple plant lines transformed with the dsRNA interference expression cassette or expression cassettes are then screened to identify plant lines that show the greatest inhibition of expression of the targeted cytochrome P450 polypeptide. Methods for using dsRNA interference to inhibit the expression of endogenous plant genes are described in Waterhouse et al. (1998) *Proc. Natl. Acad. Sci. USA* 95:13959-13964, Liu et al. (2002) *Plant Physiol.* 129:1732-1743, and WO 99/49029, WO 99/53050, WO 99/61631, and WO 00/49035; each of which is herein incorporated by reference.

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for a cytochrome P450 polypeptide that is involved in the metabolic conversion of nicotine to nornicotine). Methods of using amplicons to inhibit the expression of endogenous plant genes are described, for example, in Angell and Baulcombe (1997) *EMBO J.* 16:3675-3684, Angell and Baulcombe (1999) *Plant J* 20:357-362, and U.S. Pat. No. 6,646,805, each of which is herein incorporated by reference.

In additional embodiments of the present invention, the polynucleotide expressed by the expression cassette of the invention is catalytic RNA or has ribozyme activity specific for the messenger RNA of a cytochrome P450 polypeptide described herein. Thus, the polynucleotide causes the degradation of the endogenous messenger RNA, resulting in reduced expression of the cytochrome P450 polypeptide. This method is described, for example, in U.S. Pat. No. 4,987,071, herein incorporated by reference.

In further embodiments of the invention, inhibition of the expression of one or more cytochrome P450 polypeptides may be obtained by RNA interference (RNAi) by expression of a gene encoding a micro RNA (miRNA). miRNAs are regulatory agents consisting of about 22 ribonucleotides. miRNA are highly efficient at inhibiting the expression of endogenous genes. See, for example Javier et al. (2003) *Nature* 425: 257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of cytochrome P450 polypeptide expression, the 22-nucleotide sequence is selected from a cytochrome P450 polypeptide transcript sequence and contains 22 nucleotides encoding this cytochrome P450 polypeptide sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

In still other embodiments of the invention, inhibition of the expression of one or more cytochrome P450 polypeptides by RNAi may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene product whose expression is to be inhibited, in this case, a cytochrome P450 polypeptide described herein, and an antisense sequence that is fully or partially complementary to the sense sequence. Alternatively, the base-paired stem region may correspond to a portion of a promoter sequence controlling expression of the gene encoding the cytochrome P450 polypeptide to be inhibited. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:4985-4990; Stoutjesdijk et al. (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 407: 319-320. In fact, Smith et al. show 100% suppression of endogenous gene expression using ihpRNA-mediated interference. Methods for using ihpRNA interference to inhibit the expression of endogenous plant genes are described, for example, in Smith et al. (2000) *Nature* 407:319-320; Wesley et al. (2001) *Plant J* 27:581-590; Wang and Waterhouse (2001) Curr. Opin. Plant Biol. 5:146-150; Waterhouse and Helliwell (2003) *Nat. Rev. Genet.* 4:29-38; Helliwell and Waterhouse (2003) *Methods* 30:289-295, and U.S. Patent Publication No. 20030180945, each of which is herein incorporated by reference.

In one such embodiment, RNAi is accomplished by expressing an inhibitory sequence that comprises a first sequence of a cytochrome P450 polynucleotide of the invention that is about 90 bp to about 110 bp in length, including 90, 91, 92, 93, 94, 95, 96, 97, 98, 99, 100, 101, 102, 103, 104, 105, 106, 107, 108, 109, and 110 bp in length, and a second sequence that is complementary to all or a part of the first sequence. In another such embodiment, the inhibitory sequence comprises a first sequence of a cytochrome P450 polynucleotide of the invention that is about 290 to about 310 bp in length, including 290, 291, 292, 293, 294, 295, 296, 297, 298, 299, 300, 301, 302, 303, 304, 305, 306, 307, 308, 309, and 310 bp in length, and a second sequence that is complementary to all or a part of the fragment sequence.

In other embodiments of the invention, RNAi is accomplished by expressing an inhibitory sequence that comprises a first polynucleotide sequence containing the nucleotides from about position 265 to about position 625 of a cytochrome P450 coding sequence disclosed herein and a second sequence that is fully or partially complementary thereto. In some of these embodiments, the inhibitory sequence comprises as the first polynucleotide sequence the nucleotides corresponding to about position 297 to about position 594 of the P450 coding sequence set forth in SEQ ID NO:3 or SEQ ID NO:5 and the second sequence is the complement (i.e., antisense sequence) of this first sequence. The inhibitory sequence can optionally comprise an intron sequence linked between the first and second sequences. Any intron known to those of skill in the art can be used in this manner. In some embodiments, the intron is from the soybean omega-6 fatty acid desaturase (FAD) (see GenBank Accession No. DQ672337, and Example 7 herein below). In one such embodiment, the intron comprises about 151 nucleotides that comprise nucleotides 100-247 of the soybean omega-6 fatty acid desaturase polynucleotide shown in GenBank Accession No. DQ672337. Examples of other introns include, but are not limited to, the intron nucleotide sequences of alcohol dehydrogenase (adh1) genes. Expression of this inhibitory sequence produces an intron-containing hairpin RNA that strongly interferes with expression of the cytochrome P450 polypeptides disclosed herein. In this manner, *Nicotiana* plants that are normally converters of nicotine to nornicotine that are transformed with an expression cassette comprising such an inhibitory sequence advantageously have a nicotine to nornicotine conversion rate that, surprisingly, is even lower than that observed for *Nicotiana* plants that are nonconverters of nicotine to nornicotine.

In yet other embodiments of the invention, RNAi is accomplished by expressing an inhibitory sequence that comprises a first polynucleotide sequence containing the nucleotides from about position 1420 to about position 1580 of a cytochrome P450 coding sequence disclosed herein and a sequence that is fully or partially complementary thereto. In some of these embodiments, the inhibitory sequence comprises as the first polynucleotide sequence the nucleotides corresponding to about position 1453 to about position 1551 of the P450 coding sequence set forth in SEQ ID NO:1 and the second sequence is the complement (i.e., antisense sequence) of this first sequence. The inhibitory sequence can optionally comprise an intron sequence linked between the first and second sequences. Any intron known to those of skill in the art can be used in this manner, as noted herein above. Expression of this inhibitory sequence produces a hairpin RNA (or intron-containing hairpin RNA when the intron is present) that also interferes with expression of the cytochrome P450 polypeptides disclosed herein.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs that can interact with the homologous promoter region may trigger degradation or methylation to result in silencing (Aufsatz et al. (2002) *Proc. Natl. Acad Sci.* 99 (Suppl. 4):16499-16506; Mette et al. (2000) *EMBO J* 19(19):5194-5201).

In further embodiments, a polynucleotide may be utilized that encodes a zinc finger protein that binds to a gene encoding a cytochrome P450 polypeptide, resulting in reduced expression of the gene. In particular embodiments, the zinc finger protein binds to a regulatory region of a cytochrome P450 polypeptide gene. In other embodiments, the zinc finger protein binds to a messenger RNA encoding a cytochrome P450 polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 20030037355; each of which is herein incorporated by reference.

In other embodiments of the invention, the polynucleotide encodes an antibody that binds to at least one cytochrome P450 polypeptide, and reduces the activity of a cytochrome P450 polypeptide of the present invention. In another embodiment, the binding of the antibody results in increased turnover of the antibody-cytochrome P450 polypeptide complex by cellular quality control mechanisms. The expression of antibodies in plant parts and the inhibition of molecular pathways by expression and binding of antibodies to proteins in plant parts are well known in the art. See, for example, Conrad and Sonnewald (2003) *Nature Biotech.* 21:35-36, incorporated herein by reference.

In other embodiments, the activity of a cytochrome P450 polypeptide of the present invention is reduced or eliminated by disrupting the gene encoding the cytochrome P450 polypeptide. The gene encoding the cytochrome P450 polypeptide may be disrupted by any method known in the art, for example, by transposon tagging or by mutagenizing plants using random or targeted mutagenesis and selecting for plants that have reduced cytochrome P450 activity.

Transposon tagging may be used to reduce or eliminate the activity of one or more cytochrome P450 polypeptides of the present invention. Transposon tagging comprises inserting a transposon within an endogenous cytochrome P450 gene to reduce or eliminate expression of the cytochrome P450 polypeptide.

In this embodiment, the expression of one or more cytochrome P450 polypeptides is reduced or eliminated by inserting a transposon within a regulatory region or coding region of the gene encoding the cytochrome P450 polypeptide. A transposon that is within an exon, intron, 5' or 3' untranslated sequence, a promoter, or any other regulatory sequence of a cytochrome P450 polypeptide gene may be used to reduce or eliminate the expression and/or activity of the encoded cytochrome P450 polypeptide.

Methods for the transposon tagging of specific genes in plants are well known in the art. See, for example, Maes et al. (1999) *Trends Plant Sci.* 4:90-96; Dharmapuri and Sonti (1999) *FEMS Microbiol. Lett.* 179:53-59; Meissner et al. (2000) *Plant J.* 22:265-274; Phogat et al. (2000) *J. Biosci.* 25:57-63; Walbot (2000) *Curr. Opin. Plant Biol.* 2:103-107; Gai et al. (2000) *Nucleic Acids Res.* 28:94-96; Fitzmaurice et al. (1999) *Genetics* 153:1919-1928).

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see Ohshima et al. (1998) *Virology* 243:472-481; Okubara et al. (1994) *Genetics* 137:867-874; and Quesada et al. (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See McCallum et al. (2000) *Nat. Biotechnol.* 18:455-457, herein incorporated by reference.

Mutations that impact gene expression or that interfere with the function of the encoded cytochrome P450 protein can be determined using methods that are well known in the art. Insertional mutations in gene exons usually result in null-mutants. Mutations in conserved residues can be particularly effective in inhibiting the metabolic function of the encoded protein. Conserved residues of plant cytochrome P450 polypeptides suitable for mutagenesis with the goal to eliminate activity of a cytochrome P450 polypeptide in converting nicotine to nornicotine in a *Nicotiana* plant or plant part have been described (See, for example, FIGS. 3 and 4). Such mutants can be isolated according to well-known procedures.

In another embodiment of this invention, dominant mutants can be used to trigger RNA silencing due to gene inversion and recombination of a duplicated gene locus. See, for example, Kusaba et al. (2003) *Plant Cell* 15:1455-1467.

While a number of sequences are recognized in the practice of the invention, in particular SEQ ID NO:3 and SEQ ID NO:5 find particular use. While not bound by any particular mechanisms of action, it is believed that these sequences encode a nicotine demethylase that catalyzes the oxidative N-demethylation of nicotine to nornicotine. Thus, methods to specifically inhibit these coding sequences and not other P450 sequences may be beneficial to the recombinant plant. That is, strategies that would lead to inhibition of gene function of this individual locus may prove to be superior to those that inhibit the entire gene family. The P450 enzymes are involved in many mechanisms in the plant, the inhibition of which may prove deleterious or detrimental to the growth and development of the plant or may negatively impact factors such as the disease defense capabilities of the plant. Likewise, because the *Nicotiana* plant P450 enzymes have been implicated in plant metabolites such as phenylpropanoid, alkaloids, terpenoids, lipids, cyanogenic glycosides, glucosinolates, and a host of other chemical entities, disruption of p450 activity may alter components involved in tobacco flavor, texture, or other properties that would impact the commercial usefulness of the plant. Therefore, the use of the methods discussed above to inhibit expression in a manner that specifically targets the coding sequence of SEQ ID NO:3 or SEQ ID NO:5 may be preferred, including targeted mutational strategies, such as chimeraplasty. See, for example, Stewart et al. (2000) *Biotechniques* 29(4): 838-843; Graham et al. (2002) *Biochim Biophys Acta* 1587(1): 1-6, herein incorporated by reference.

The protein encoded by the cDNA designated 3D_C12-10 (SEQ ID NO:4) differs from 3D_C12-7 (SEQ ID NO:6) at only two amino acid residues immediately following the start methionine. The codons corresponding to these amino acids were contained within the PCR primer used to generate the 3D_C12-7 cDNA. Thus, the original mRNA template from which 3D_C12-7 was amplified may be the same as that corresponding to the 3D_C12-10 gene, with the PCR primer sequences mediating the changes observed in the second and third amino acid sequence. Regardless, the encoded protein products would function identically. The location of the two amino acids that differ between the predicted proteins is in the N-terminal signal sequence that merely serves to anchor the protein to the endoplasmic reticulum membrane and therefore would not be expected to influence the catalytic properties of the enzyme.

In another embodiment of the invention, the compositions of the invention find use in screening methods to identify nonconverter plants for use in breeding programs. In this manner, the nucleotide sequences of the invention can be used to screen native germplasms for nonconverter plants having a stable mutation in one or more p450 genes identified herein.

These nonconverter plants identified by the methods of the invention can be used to develop breeding lines.

In addition to the nucleotide sequences encoding P450 coding sequences, compositions of the invention include an intron sequence in the 3D_C12-10 sequence that can be used in screening methods. While not bound by any mechanism of action, the 3D_C12-7/3D_C12-10 gene(s) may represent the only member(s) of the 3D_C12 family involved in the metabolic conversion of nicotine to nornicotine (and as stated previously there is a good likelihood that the 3D_C12-7 and 3D_C12-10 cDNAs originated from a single unique genetic locus). For certain applications it would be useful to have a means of diagnostically differentiating this specific member of the 3D_C12 gene family from the rest of the closely related sequences within this family. For example, it is possible that within the naturally existing tobacco germplasm (or in mutagenized populations), accessions may exist in which this gene is naturally dysfunctional and may therefore may be valuable as a permanently nonconverter resource. A method to specifically assay for such genotypes (e.g. deletion mutants, rearrangements, and the like) could serve as a powerful tool. To obtain such a tool, the sequence alignment shown in FIG. 3A-3G was used to design PCR primers in regions possessing polymorphisms among the members. One primer combination (5' primer shown in SEQ ID NO:25 and 3' primer shown in SEQ ID NO:26) using sequences specific to 3D_C12-10 yields two particularly useful results: (1) all PCR products amplified from tobacco genomic DNA gave that same unique product (as determined by DNA sequence analysis); and (2) the presence of a 992 bp intron was revealed that is located between the primer sequences (FIG. 7; intron shown in SEQ ID NO:24).

When any cDNA corresponding to a member of the 3D_C12 family is used as a hybridization probe in a Southern blotting assay of tobacco genomic DNA, a complex pattern is observed. This is expected, given that there are multiple, closely related members of this gene family. Because the intron regions of genes are typically less conserved than exons, it is predicted that the use of an intron-specific probe would reduce this complexity and better enable one to distinguish the gene(s) corresponding to the 3D_C12-7/3D_C12-10 gene from the other members of the family. Indeed, the probe corresponding to the sequence shown in FIG. 7 resulted in a Southern blotting pattern with greatly reduced complexity. The use of a 3D_C12-10 intron-specific probe, and/or the PCR primers used to generate the fragment shown in FIG. 7, therefore provide powerful tools in assays to determine whether any naturally occurring, or mutagenized, tobacco plants possess deletions or rearrangements that may render the gene inactive. Such a plant can then be used in breeding programs to create tobacco lines that are incapable of converting.

Transformed Plants, Plant Parts, and Products Having Reduced Nornicotine and NNN Content The cytochrome P450 polynucleotides of the invention, and variants and fragments thereof, can be used in the methods of the present invention to inhibit expression or function of cytochrome P450s that are involved in the metabolic conversion of nicotine to nornicotine in a plant. In this manner, inhibitory sequences that target expression or function of a cytochrome P450 polypeptide disclosed herein are introduced into a plant or plant cell of interest. In some embodiments the expression cassettes described herein are introduced into a plant of interest, for example, a *Nicotiana* plant as noted herein below, using any suitable transformation methods known in the art including those described herein.

The methods of the invention do not depend on a particular method for introducing a sequence into a plant or plant part, only that the desired sequence gains access to the interior of at least one cell of the plant or plant part. Methods for introducing polynucleotide sequences into plants are known in the art and include, but are not limited to, stable transformation methods, transient transformation methods, and virus-mediated methods.

Transformation protocols as well as protocols for introducing heterologous polynucleotide sequences into plants vary depending on the type of plant or plant cell targeted for transformation. Suitable methods of introducing polynucleotides into plant cells of the present invention include microinjection (Crossway et al. (1986) *Biotechniques* 4:320-334), electroporation (Shillito et al. (1987) *Meth. Enzymol.* 153: 313-336; Riggs et al. (1986) *Proc. Natl. Acad. Sci. USA* 83:5602-5606), *Agrobacterium*-mediated transformation (U.S. Pat. Nos. 5,104,310, 5,149,645, 5,177,010, 5,231,019, 5,463,174, 5,464,763, 5,469,976, 4,762,785, 5,004,863, 5,159,135, 5,563,055, and 5,981,840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in *Plant Cell, Tissue, and Organ Culture Fundamental Methods*, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); all of which are herein incorporated by reference.

Any plant tissue that can be subsequently propagated using clonal methods, whether by organogenesis or embryogenesis, may be transformed with a recombinant construct comprising a cytochrome P450 inhibitory sequence, for example, an expression cassette of the present invention. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described herein include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

As used herein, the term "stable transformation" is intended to mean that the nucleotide construct of interest introduced into a plant integrates into the genome of the plant and is capable of being inherited by the progeny thereof. "Transient transformation" is intended to mean that a sequence is introduced into the plant and is only temporally expressed or is only transiently present in the plant.

In specific embodiments, the inhibitory sequences of the invention can be provided to a plant using a variety of transient transformation methods. The inhibitory sequences of the invention can be transiently transformed into the plant using techniques known in the art. Such techniques include viral vector systems and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethyenlimine (PEI; Sigma #P3143).

In other embodiments, the inhibitory sequence of the invention may be introduced into plants by contacting plants with a virus or viral nucleic acids. Generally, such methods involve incorporating an expression cassette of the invention within a viral DNA or RNA molecule. It is recognized that promoters for use in the expression cassettes of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Transformed cells may be grown into *Nicotiana* plants in accordance with conventional methods. See, for example, methods disclosed in Vasil and Hildebrandt (1965) *Science* 150:889; Negaard and Hoffman (1989) *Biotechniques* 7(8): 808-812. These plants may then be grown, and either pollinated with the same transformed line or different lines, and the resulting progeny having expression of the desired phenotypic characteristic identified, i.e., reduced expression of one or more cytochrome P450s that are involved in the metabolic conversion of nicotine to nornicotine, and thus reduced content of nornicotine, and a concomitant reduced content of its nitrosamine metabolite, NNN, in the plant, particularly in the leaf tissues. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

The compositions and methods of the invention can be used to reduce the nornicotine content, particularly in the leaves and stems, of any plant of the genus *Nicotiana* including, but not limited to, the following species: *acuminata, affinis, alata, attenuate, bigelovii, clevelandii, excelsior, forgetiana, glauca, glutinosa, langsdorffii, longiflora, obtusifolia, palmeri, paniculata, plumbaginifolia, qudrivalvis, repanda, rustica, suaveolens, sylvestris, tabacum, tomentosa, trigonophylla,* and *x. sanderae.* The present invention also encompasses the transformation of any varieties of a plant of the genus *Nicotiana*, including but not limited to *Nicotiana acuminata multiflora, Nicotiana alata grandiflora, Nicotiana bigelovii quadrivalvis, Nicotiana bigelovii wallacei, Nicotiana obtusifolia obtusifolia, Nicotiana obtusifolia plameri, Nicotiana quadrivalvis bigelovii, Nicotiana quadrivalvis quadrivalvis, Nicotiana quadrivalvis wallacei,* and *Nicotiana trigonophylla palmeri,* as well as varieties commonly known as flue or bright varieties, Burley varieties, dark varieties, and oriental/Turkish varieties.

The transgenic plants of the genus *Nicotiana* as described herein are suitable for conventional growing and harvesting techniques, such as cultivation in manure rich soil or without manure, bagging the flowers or no bagging, or topping or no topping. The harvested leaves and stems may be used in any traditional tobacco product including, but not limited to, pipe, cigar and cigarette tobacco, and chewing tobacco in any form including leaf tobacco, shredded tobacco, or cut tobacco.

Thus the present invention provides a *Nicotiana* plant, particularly leaf tissues of these plants, comprising an expression cassette of the invention and a reduced amount of nornicotine and N'-nitrosonornicotine. As used herein, the term "a reduced amount" or "a reduced level" is intended to refer to an amount of nornicotine and/or N'-nitrosonornicotine in a treated or transgenic plant of the genus *Nicotiana* or a plant part or tobacco product thereof that is less than what would be found in a plant of the genus *Nicotiana* or a plant part or tobacco product from the same variety of tobacco, processed (i.e., cultured and harvested) in the same manner, that has not been treated or was not made transgenic for reduced nornicotine and/or N'-nitrosonornicotine. The amount of nornicotine may be reduced by about 10% to greater than about 90%, including greater than about 20%, about 30%, about 40%, about 50%, about 60%, about 70%, and about 80%.

The term "tobacco products" as used herein include, but are not limited to, smoking materials (e.g., cigarettes, cigars, pipe tobacco), snuff, chewing tobacco, gum, and lozenges. The present invention also encompasses a range of tobacco product blends that can be made by combining conventional tobacco with differing amounts of the low nornicotine and/or N'-nitrosonornicotine tobacco described herein. In further embodiments, the plant or plant part of the genus *Nicotiana* as described above is cured tobacco.

In some embodiments of the present invention, the tobacco product reduces the carcinogenic potential of tobacco smoke that is inhaled directly with consumption of a tobacco product such as cigars, cigarettes, or pipe tobacco, or inhaled as secondary smoke (i.e., by an individual that inhales the tobacco smoke generated by an individual consuming a tobacco product such as cigars, cigarettes, or pipe tobacco). The cured tobacco described herein can be used to prepare a tobacco product, particularly one that undergoes chemical changes due to heat, comprising a reduced amount of nornicotine and/or N'-nitrosonornicotine in the smoke stream that is inhaled directly or inhaled as secondary smoke. In the same manner, the tobacco products of the invention may be useful in the preparation of smokeless tobacco products such as chewing tobacco, snuff, and the like.

The tobacco products obtained from the transgenic tobacco plants of the present invention thus find use in methods for reducing the carcinogenic potential of these tobacco products, and reducing the exposure of humans to the carcinogenic nitrosamine NNN, particularly for individuals that are users of these tobacco products.

The following examples are offered by way of illustration and not by way of limitation.

EXPERIMENTAL

The following materials and protocols were utilized in the experiments described herein below.

Plant Materials

All plant materials utilized in these experiments were provided by Dr. Earl Wernsman, Department of Crop Science, North Carolina State University. DH 91-1307-46(NC) and DH91-1307-46(Con) are near-isogenic doubled haploid Burley lines (nonconverter and converter, respectively) recovered from the same maternal haploid plant. Burley lines DH 98-326-3 (nonconverter) and DH 98-326-1 (converter), and DH 98-325-5 (nonconverter) and DH 98-325-6 (converter) represent two additional pairs of near-isogenic lines. SC58 is a flue-cured tobacco variety, nonconverter individuals of which are designated SC58($C_TC_T$). SC58($C_TC_T$) is a near-isogenic stable converter line that originated though the introgression of the single dominant converter locus ($C_T$) found in the tobacco progenitor species *N. tomentosiformis* into SC58 (Mann et al. (1964) *Crop Sci.* 4:349-353. After eight additional backcrosses to SC58, the near-isogenic SC58($C_TC_T$) line was created and subsequently maintained via self-fertilization.

All plants were maintained in growth chambers or greenhouses using standard potting soil and fertilizer. For the microarray studies, the metabolism of nicotine to nornicotine was accelerated by excising individual leaves and inserting their petioles into a solution of 0.1% ethephon or 1% sodium bicarbonate. The leaves were then placed in a growth chamber (27° C.) for 5 to 7 hours to facilitate the entry of the ethephon or sodium bicarbonate solutions throughout the transpirational stream. The treated leaves were placed in small plastic storage bags after being lightly sprayed with water (to maintain high humidity) and cured for three days at 30° C. in the dark. To enhance the nicotine to nornicotine conversion in the transgenic plants generated in this study, detached leaves were dipped into a solution of 0.2% ethephon, dried, and cured in plastic storage bags for seven days at room temperature in the dark.

cDNA Libraries and Expressed Sequence Tags

Total cellular RNA was isolated from senescing leaf tissue of Burley lines DH 91-1307-46(NC) and DH 91-1307-46 (Con) using the TRIzol® reagent according to the manufacturer's protocol (Invitrogen). PolyA+RNA was isolated from total RNA using the MessageMaker system (Invitrogen), and cDNA was subsequently synthesized and cloned into the lambda ZAP II phage vector using the ZAP-cDNA Synthesis and Gigapack III Gold Cloning Kit (Stratagene). Aliquots of the phage libraries were converted to pBluescript-based plasmid libraries following the mass excision protocol outlined by Stratagene.

Thousands of colonies from both the converter and non-converter libraries were grown on selective solid media and picked into 384-well plates containing Luria broth (with ampicillin) in 10% glycerol to facilitate long term storage of the clones at −80° C. Over 11,000 clones from each library were transferred from the 384-well plates to 96-well growth blocks and grown in selective media. Plasmids were isolated in 96-well format using the R.E.A.L. Preparation Kit (Qiagen) with the aid of a BioRobot 3000 Workstation (Qiagen). To generate the ESTs, the plasmid clones were sequenced using the T3 primer (Qiagen) and BigDye® Terminator system (Applied Biosystems) according to the BigDye® cycle sequencing protocol. Performa® DTR 96-well plates (Edge Biosystems) were used to remove the unincorporated dye from the sequencing reactions prior to loading the samples onto a Perkin Elmer Prism 3700 96-Capillary Automated DNA Sequencer.

Preparation of DNA Chips

To obtain DNAs suitable for spotting onto glass slides, the M13 forward and reverse sequencing primers (Qiagen) were used as PCR primers to amplify cDNA inserts from the plasmids containing cDNAs represented in the EST databases. Plasmid clones were subjected to PCR in 96-well format using an Applied Biosystems Gene Amp 9700 model thermocycler. The resulting PCR products were processed through Millipore Multiscreen™ PCR or Montage™ PCRμ96 purification systems. The resulting products were transferred into 384-well plates containing equal volumes of DSMO. The final DNA concentrations were estimated to be equal to or greater than 0.1 mg/ml. The DNAs were subsequently spotted onto amino silane-coated slides (Corning® GAPS II) using an Affymetrix GMS 417 array printer. DNAs were immobilized to the slide surface by UV crosslinking (~120 mJ/m$^2$), followed by baking at 75° C. for two hours.

Microarray Hybridization and Analysis

The amino allyl dUTP-based indirect method of dye incorporation described by "The Institute of Genome Research" (http://pga.tigr.org/protocols.html) was used to label nonconverter and converter RNAs with Cy3 and Cy3 fluorescent dyes (Amersham Biosciences). Briefly, 20 μg of total RNA was reverse transcribed in a 30 μl volume containing 400 units of SuperScript II RT (Invitrogen), 6 ng random hexamer primers, 0.5 mM each of dATP, dCTP, and dGTP, 0.3 mM dTTP, and 0.2 mM amino allyl dUTP (Sigma) in first strand synthesis buffer (Invitrogen). Reactions were incubated for 6 to 14 hours at 42° C., followed by hydrolysis of the RNA with NaOH. The resulting first strand cDNA molecules were column purified (Qiagen) and washed with phosphate buffer. Coupling reactions of the NHS-ester Cy3 or Cy5 fluorescent dyes to the cDNA occurred during incubation in 0.05 M sodium carbonate buffer (pH 9.0) and 25% DMSO at room temperature for 1.5 hours.

Microarray slides were prehybridized in a solution of 5×SSC, 0.1% SDS, and 1% BSA at 42° C. for 45 minutes, rinsed gently with dH$_2$O and isopropanol, and dried by low speed centrifugation. The Cy3- and Cy5-labeled cDNAs were column purified (Qiagen), combined, and hybridized to the DNA slides in a solution containing 5×SSC, 0.5% SDS, 5×Denhardt's, 0.45 μg/μl Poly A RNA, 0.45 μg/μl calf thymus DNA, and 50% formamide. The slides were incubated with the hybridization solution for 14 to 16 hours at 42° C. Post-hybridization washes consisted of sequential 4-minute incubations with the following solutions: 1×SSC, 0.2% SDS; 0.1×SSC, 0.2% SDS; 0.1×SSC, and a final 10 second rinse with 0.01×SSC.

The microarrays were subsequently scanned using ScanArray 2.1 (GSI Lumonics) or ScanArray Express (PerkinElmer). Sequential scanning for Cy5 and Cy3 fluorescence was performed at a maximal resolution of 10 gm/pixel, and laser power and PMT gain adjusted to provide reliable and equivalent signal strengths. The acquired array images were quantified for signal intensity with QuantArray™ analysis software (PerkinElmer), using the histogram-based method. Total intensities were used as quantification output fields, and the acquired data sets were saved as Unicode, tab-delimited text files. Importation of the text files into Microsoft Excel enabled the subsequent calculation of Cy5/Cy3 and Cy3/Cy5 ratios, the statistic we employed for the identification of candidate genes.

Cloning Full-Length and Additional Members of the 3D_C12 Gene Family

To clone the entire coding region of 3D_C12 and 7D_A06 a modified 5'-RACE strategy was employed using a pBluescript II vector-specific forward primer (BlueSK; 5'-CGCTCTAGAACTAGTGATC-3'; SEQ ID NO:17) and a set of gene-specific reverse primers. Two 3D_C12-specific reverse primers were designed, one of which is complementary to the downstream portion of the 3' untranslated region (5'-TTTTTGGGACAATCAGTCAA-3'; SEQ ID NO:18) and the other complementary to a sequence within the coding region (5'-GTTAGATTTATCGTACTCGAATT-3'; SEQ ID NO: 19). For the former primer, the first five Ts are complementary to the polyA tail of the transcript. A 7D_A06-specific reverse primer (5'-TTCATTTCAAATTATTTTATGCACCA-3'; SEQ ID NO:20) was also designed, and is complementary to a segment in the 3' untranslated region of this gene. PCR reactions contained 10 ng of converter tobacco leaf cDNA library (within the pBluescript vector) as template, 2 µM concentration of each primer, 350 µM of each dNTP, and 1.5 mM $MgCl_2$ in a final reaction volume of 50 µL. Amplification was initiated by the addition of 2.5 units of UniPol enzyme mix using conditions described by the manufacturer (Roche). After an initial denaturation step at 94° C. for 4 minutes, the samples were subjected to 30 cycles of denaturation at 94° C. for 15 seconds, annealing at 57° C. for 30 seconds, and extension at 72° C. for 90 seconds. A final extension step at 72° C. for 10 minutes was included at the end of the 30 cycles. The amplicons were ligated into the pGEM Easy T/A vector (Promega), and 10 randomly selected clones from each amplification were subjected to DNA sequence analysis. Nucleic acid and predicted protein sequences of the various members of the 3D_C12 gene family were analyzed and compared using the BLASTX (Altschul et al. (1997) *Nucleic Acids Res.* 25:3389-3402), ClustalW (Higgins et al. (1994) *Nucleic Acids Res.* 22:4673-4680) and GAP (University of Wisconsin Genetic Computing Group software package) algorithms.

The above described strategy was effective in identifying full-length sequence information for 3D_C12 and 7D_A06. In addition, PCR amplifications using the PCR primer internal to the 3D_C12 coding region gave rise to partial-sequence information for the unique 3D_C12-15 cDNA. In an attempt to obtain full-length sequence information for 3D_C12-15, a gene-specific primer complementary to the 5' terminus of its coding region (5'-ATGGTTTTTCCCATAGAAGCC-3'; SEQ ID NO:21) was used in conjunction with a pBluescript-specific reverse primer (5'-TCGAGGTCGACGGTATC-3'; SEQ ID NO:22). Although a full-length 3D_C12-15 cDNA was not recovered, this amplification resulted in the isolation of 3D_C12-7, which proved to be another unique member of the 3D_C12 gene family.

Transgenic Plant Analysis

The RNAi-based gene silencing constructs were assembled in a version of the pKYL80 cloning vector (Schardl et al. (1987) *Gene* 61:1-11) that was engineered to contain a 151-bp fragment of the soybean FAD3 gene intron between the XhoI and SacI restriction sites of the polylinker (pKYLX80I). To create a construct in which the FAD3 intron was flanked by a sense and antisense fragment of 3D_C12, a 99-bp region located immediately upstream of the stop codon of the 3D_C12 cDNA (FIG. 3A-3G) was cloned between the HindIII-XhoI and SacI-XbaI restriction sites of pKYLX80I in its sense and antisense orientation, respectively. The resulting HindIII-XbaI fragment containing the 3D_C12 sense arm, FAD3 intron, and 3D_C12 antisense arm was subcloned into the pKYLX71 plant binary expression vector (Maiti et al. (1993) *Proc. Natl. Acad. Sci. USA* 90:6110-6114) between the 35S CaMV promoter and a rubisco small subunit terminator.

Overexpression constructs were created by replacing the 3-glucuronidase ORF of the plant binary expression vector pBI121 (Clontech) with the full-length coding regions of the 3D_C12, 7D_A06, and 3D_C12-7 cDNAs. This placed the tobacco P450s under the transcriptional control of the 35S CaMV promoter. The pBI121- and pKYLX71-based constructs were transformed into *Agrobacterium tumefaciens* strain LBA 4404 and introduced into tobacco cultivars Petite Havana and DH98-325-6 (converter), respectively, using established protocols (Horsch et al. (1985) *Science* 227:1229-1231).

Northern Blot Analysis

Total cellular RNAs were isolated from tobacco leaves using the TRIZOL® method as described by the manufacturer (Invitrogen). Five to ten micrograms of RNA were size fractionated on a 1.2% agarose gel prepared in TBE buffer. RNA immobilization, probe labeling, and signal detection were carried out using the DIG nucleic acid labeling and detection kits according to the manufacturer's instructions (Roche). Alternatively, probes were synthesized using $^{32}$P-dCTP according to protocols accompanying the Random Primed DNA Labeling kit (Roche).

Alkaloid Analysis

Tobacco leaves were harvested and air dried in an oven at 65° C. for 2 days. A 100 mg sample of crushed, dried leaf was added to 0.5 ml of 2 N NaOH in a 20 mL scintillation vial. The sample was mixed and allowed to incubate for 15 minutes at room temperature. Alkaloids were extracted by the addition of 5 mL of extraction solution [0.04% quinoline (wt/vol) dissolved in methyl-t-butyl ether] and gently rotated on a linear shaker for 3 hours. Following phase separation, an aliquot of the organic phase was transferred to a sample vial. Samples were analyzed using a PerkinElmer Autosystem XL gas chromatograph equipped with a flame ionization detector, a 4 mm split/splitless glass liner, and a 30 m×0.53 mm ID DB-5 column. Chromatographic conditions were as follows: detector temperature: 250° C.; injector temperature: 250° C.; helium flow rate at 120° C.: 20 mL/min; injection volume: 2 µL; column conditions: 120° C., hold 1 minute, 120-280° C. at 30° C./minute ramping rate, hold at 280° C. for 2 minutes. Alkaloid composition was determined by the TotalChrome Navigator software using a calibration curve.

Example 1

Generation of EST Databases

RNAs isolated from senescing leaves of the converter genotype DH 91-1307-46(Con) and its near-isogenic nonconverter counterpart DH 91-1307-46(NC) were used to generate cDNA libraries. High-throughput automated DNA sequencers were initially used to generate single-run sequence information (ESTs) for 11,136 randomly chosen cDNAs from the converter library. The local alignment search tool BLASTX (Altschul et al. (1990) *J. Mol. Biol.* 215:403-410) was used to compare the predicted protein sequence of each tobacco cDNA with the nonredundant protein database curated by the National Center for Biotechnology Information of the National Library of Medicine and National Institutes of Health. Subsequently, a similar annotated EST database was generated by conducting sequencing runs on 11,904 cDNAs selected from the nonconverter library.

Example 2

Microarray Analyses of Converter CDNA Library

Methods

Upon completion of the EST database generated from the converter cDNA library, the inserts from 4992 clones were amplified by PCR and spotted onto glass slides. Given the possibility that the nicotine demethylase enzyme may be catalyzed by an enzyme of the P450 class of oxidative enzymes, special attention was given to library entries that were predicted by BLASTX analysis to encode P450s.

From visual inspection of the BLASTX results, it was estimated that 31 unique P450 genes were represented in the database. When selecting specific 96-well plates to be included on the microarray, care was taken to ensure that all unique P450 genes would be included among the 4992 cDNAs selected.

RNAs isolated from the near-isogenic Burley genotypes DH 98-326-3 (nonconverter) and DH 98-326-1 (converter), and DH 98-325-5 (nonconverter) and DH 98-325-6 (converter) were used to generate Cy3- and Cy5-labeled cDNAs. To maximize the metabolic conversion of nicotine to nornicotine in converter genotypes, detached leaves were treated with sodium bicarbonate or ethephon prior to curing, treatments that have been shown to accelerate nornicotine production in converter plants while having no effect in nonconverter individuals (Fannin and Bush (1992) *Med. Sci. Res.* 20:867-868; Shi et al. (2003) *J. Agric. Food Chem.* 51:7679-7683).

To minimize the variability inherent with microarray experiments, reciprocal experiments were conducted simultaneously. In this manner, DH 98-325-5 RNA was labeled with Cy5 and DH 98-325-6 RNA was labeled with Cy3, and then in a reciprocal experiment DH 98-325-5 RNA was labeled with Cy3 and DH 98-325-6 RNA was labeled with Cy5 (collectively referred to as Exp. 2.1). Similarly, DH 98-326-3 and DH 98-326-1 RNAs were labeled with Cy3 and Cy5, respectively, in one experiment, and then the same RNAs were labeled with Cy5 and Cy3, respectively, in a reciprocal experiment (collectively referred to as Exp. 2.2).

Even when conducted reciprocally, the results of any given microarray experiment are likely to include "false positives," representing genes that are differentially regulated between a specific genotypic pair and/or uniquely in response to a specific treatment, as opposed to differences directly associated with the conversion phenomenon. To define the set of candidate genes that are most likely to be upregulated due to the conversion process, cDNAs were identified that met the following criteria: for any set of reciprocal experiments (i.e., Exp. 2.1, or Exp. 2.2), the hybridization intensity of a given cDNA had to be at least 2-fold higher with the converter probe than nonconverter probe in at least one of the hybridizations, and not less than 1.5-fold higher in the reciprocal experiment.

Experiment 2.1—Leaves from near-isogenic lines DH 98-325-5 and DH 98-325-6 were treated with ethephon and cured for 3 days at 30° C. Alkaloid analysis revealed that virtually all of the nicotine had been metabolized to nornicotine in the DH 98-325-6 leaf during this period while minimal nornicotine was observed in the DH 98-325-5 leaf. RNAs from the DH 98-325-5 nonconverter plant were labeled with the Cy3 fluorescent dye, and RNAs extracted from a DH 98-325-6 (converter) leaf were labeled with Cy5. The Cy3- and Cy5-labeled cDNAs were incubated together on the same DNA chip and allowed to hybridize overnight.

Experiment 2.2—A microarray analysis similar to Exp. 2.1 was conducted using the DH 98-326-3 (nonconverter) and DH 98-326-1 (converter) near-isogenic lines. In these experiments, leaves from each genotype were treated with 1% sodium bicarbonate and cured for 3 days at 30° C. At the end of the treatment period, nicotine was the predominant alkaloid in the DH 98-326-3 leaf, while nearly all of the alkaloid in the DH 98-326-1 leaf was nornicotine. As described for Exp. 2.1, these experiments were reciprocally conducted.

Results

In both Experiment 2.1 and Experiment 2.2, the great majority of the 4992 cDNAs spotted on the glass slides showed no substantial differences in their hybridization intensities to the competing Cy3- and Cy5-labeled probes.

Of the 4992 cDNAs spotted on the glass slides, only five showed at least 2-fold higher expression in one hybridization and not less than 1.5-fold in the reciprocal hybridization for both Exp. 2.1 and Exp. 2.2. These entries were designated 3D_C12, 7D_A06, 27C_C12, 33A_D06, and 34D_F06. BLASTX analysis of the partial sequence information for 3D_C12 and 7D_A06 found in our EST database predicted that the cDNAs encode two closely related P450 enzymes. 27C_C12 and 33A_D06 were predicted to encode glycine-rich cell wall proteins, displaying over 90% sequence identity to small tobacco glycine-rich proteins found in GenBank (e.g., Accession No. AAK57546). Clone 34D_F06 was found to contain a double cDNA insert, one insert showing homology to serine/threonine protein kinases, and the other showing high sequence identity to the same glycine-rich cell wall proteins as the 27C_C12 and 33A D06 cDNAs.

Example 3

Microarray Analysis of CDNA Non-Converter Library

Upon completion of the EST database from the nonconverter library (generated from senescing leaves of genotype DH 91-1307-46 (NC)), another set of microarray experiments was initiated. For this next generation of microarrays, the goal was to produce glass slides containing the complete nonredundant set of genes represented in both libraries.

To obtain an estimate of the number of unique genes that are represented in the database, clustering analysis was conducted to identify ESTs predicted to be represented multiple times in the database (contigs) versus those predicted to be represented only once (singletons) (Huang and Madan (1999) *Genome Res.* 9:868-877). Due to the nature of the clustering algorithms, sequences showing high, but imperfect, sequence identities are clustered into the same contig. The total set of predicted unique genes, or unigenes, within a database is calculated as the sum of the contigs and singletons. Clustering analysis of the combined converter and nonconverter databases predicted 2246 contigs and 4717 singletons for a total of 6,963 unigenes. Inserts from all singletons and an individual from each contig were amplified by PCR and spotted onto glass slides, resulting in a gene chip containing the complete 6,963 unigene set.

In addition to creating a new DNA chip, the genetic materials used to generate hybridization probes also differed from those used in Example 2. SC58 is a flue-cured tobacco variety, nonconverter individuals of which are designated SC58 ($C_TC_T$). SC58($C_TC_T$) is a near-isogenic stable converter line that originated though the introgression of the single dominant converter locus ($C_T$) found in the tobacco progenitor species *N. tomentosiformis* into SC58 (Mann et al. (1964) *Crop Sci.* 4:349-353). After eight additional backcrosses to SC58, the near-isogenic SC58($C_TC_T$) line was created and subsequently maintained via self-fertilization. The conversion phenotype of SC58($C_TC_T$) plants is unique with respect to standard converter tobacco lines in that the metabolism of nicotine to nornicotine in the leaf does not require senescence or curing. Plants possessing the $C_T$ converter locus from *N. tomentosiformis* contain nornicotine as the predominant alkaloid even in green leaf tissue (Wernsman and Matzinger (1968) *Tob. Sci.* 12:226-228).

RNAs isolated from green leaf tissue of SC58($C_TC_T$) and SC58($C_TC_T$) were labeled with Cy3 and Cy5, respectively, and simultaneously hybridized to a DNA chip containing the entire 6,963 unigene set of cDNAs. The fluorescent dyes were reversed to produce the probes for a reciprocal experiment as described in Exps. 2.1 and 2.2 of Example 2.

Results

Results were evaluated using the same criteria as in Example 2, i.e., individual cDNAs were identified that showed at least 2-fold enhanced hybridization to the labeled SC58($C_TC_T$) versus SC58($C_TC_T$) cDNAs in one experiment and at least 1.5-fold enhancement in the reciprocal assay.

Results were compared to those from Exp. 2.1 and Exp. 2.2 in Example 2 above. Enhanced hybridization of converter RNAs to cDNAs encoding members of the same closely related P450 family was the only result shared by all three microarray experiments using the defined criteria. 131 A_A02 is the name of the cDNA that was spotted onto the 6963-member unigene chip that is representative of the closely-related P450 gene family that includes 3D_C12 and 7D_A06 (3D_C12 and 7D_A06 themselves were not spotted on the unigene slide). No other cDNAs on the array in Example 3, which included representatives of the contigs containing the glycine-rich protein-encoding 27C_C12 and 33A_D06 and 34D_F06 cDNAs, scored positive by the defined criteria and also scored positive in Exp. 2.1 or Exp. 2.2 of Example 2 above, regardless of whether the results were compared individually or collectively.

where herein (and spotted onto the microarrays) were not full-length cDNAs. To obtain a full-length sequence, primers were generated corresponding to regions in the 3' flanking region and in the interior of the coding regions that were sufficiently polymorphic to distinguish between 7D_A06 and 3D_C12. These gene-specific primers were used in combination with primers specific to the cloning site of pBluescript II to amplify cDNAs from the converter cDNA library in an attempt to obtain sequence that would include the complete 5' ends of the 3D_C12 and 7D_A06 reading frames.

This strategy led to the determination of the DNA sequence corresponding to the complete coding regions of 3D_C12 (nt 1-1551 of SEQ ID NO:1; predicted amino acid sequence shown in SEQ ID NO:2) and 7D_A06 (nt 1-1554 of SEQ ID NO:7; predicted amino acid sequence shown in SEQ ID NO:8) (FIGS. 3A-3G and 4). GAP analyses of the 3D_C12 and 7D_A06 DNA and predicted protein sequences showed that they share 93.4% DNA sequence identity and 92.3% identity at the protein level (Tables 2 and 3). Initial BLASTX analysis against the nonredundant GenBank database revealed that 3D_C12 and 7D_A06 share greatest sequence homology to CYP82E1, a tobacco P450 gene of unknown

TABLE 1

Microarray results of members of the 3D_C12 gene family

| cDNA | Cy3 reading | Cy5 reading | Cy5/Cy3 ratio | Cy3 reading | Cy5 reading | Cy5/Cy3 ratio |
|---|---|---|---|---|---|---|
| | Experiment 2.1 | | | Experiment 2.1 (reciprocal) | | |
| 3D_C12 | 15514.14 | 25928.95 | 1.67 | 19355.85 | 9507.87 | 2.04 |
| 7D_A06 | 15238.23 | 37196.19 | 2.44 | 13651.03 | 8121.04 | 1.68 |
| | Experiment 2.2 | | | Experiment 2.2 (reciprocal) | | |
| 3D_C12 | 12756.43 | 28669.28 | 2.25 | 32198.81 | 16166.13 | 1.99 |
| 7D_A06 | 7571.06 | 19180.94 | 2.53 | 42408.85 | 18440.17 | 2.30 |
| | Example 3 | | | Example 3 (reciprocal) | | |
| 131A_A02 | 11138.96 | 19638.82 | 1.76 | 36963.45 | 10085.25 | 3.67 |

Combined Results

Figure 2:
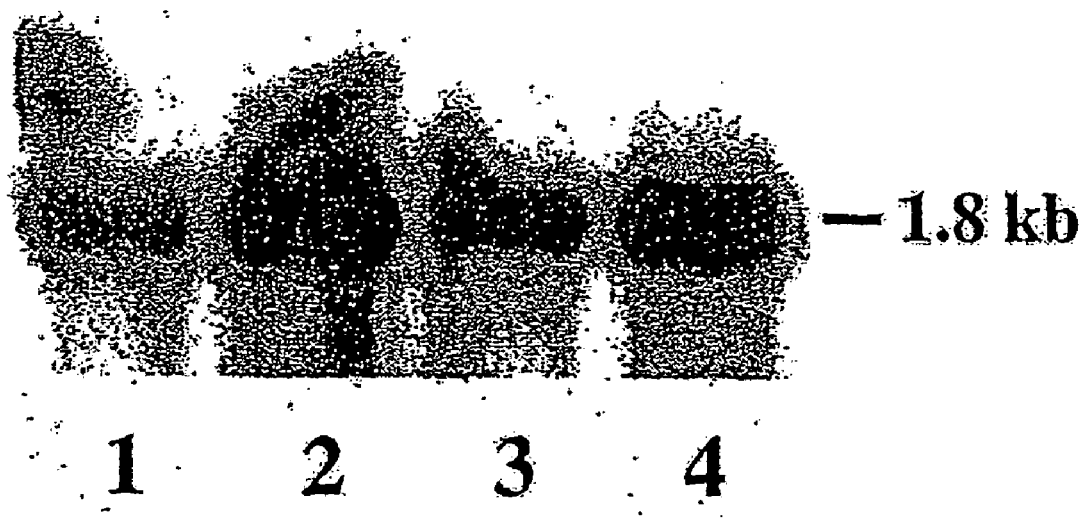
FIG. 2 shows Northern blot analysis of converter and nonconverter RNAs using 7D_A06 as a hybridization probe. Lanes 1 and 2 show RNAs isolated from sodium bicarbonate-treated leaves of genotypes DH 98-325-5 (nonconverter) and DH 98-325-6 (converter), respectively. Lanes 3 and 4 show RNAs isolated from ethephon-treated leaves of genotypes DH 98-326-3 (nonconverter) and DH 98-326-1 (converter), respectively. Estimated size of the hybridizing band is indicated in kilobases (kb).

The combined results of microarray experiments described above defined members of a closely related P450 gene family, hereafter referred to as the 3D_C12 family, to be the best candidates for playing a direct role in the metabolic conversion of nicotine to nornicotine in converter tobacco plants. The hybridization results of the members of this P450 family in each of the three microarray experiments are shown in Table 1. The results of the microarrays were independently confirmed using Northern blotting assays. As shown in FIG. 2, an approximately 2-fold higher signal was observed in senescing, cured converter leaves compared to their nonconverter counterparts when RNA blots were incubated with a radiolabeled 7D_A06 hybridization probe.

Example 4

Sequence Analysis of the 3D_C12 Gene Family

Once microarray experiments defined 3D_C12 and 7D_A06 as potentially being involved in the conversion process, obtaining complete DNA sequence information for these genes became the next step in their characterization. The original 3D_C12 and 7D_A06 clones that were sequenced when generating the EST database described elsefunction that is upregulated in response to fungal elicitors (Takemoto et al. (1999) *Plant Cell Physiol.* 40:1232-1242). The CYP82E1 protein is 66.9% and 67.5% identical to the predicted amino acid sequences of 3D_C12 (SEQ ID NO:2) and 7D_A06 (SEQ ID NO:8), respectively, and the CYP82E1 DNA sequence is 72.1% and 73.5% identical to the respective coding sequences for 3D_C12 (nt 1-1551 of SEQ ID NO:1) and 7D_A06 (nt 1-1554 of SEQ ID NO:7).

TABLE 2

Nucleotide sequence identities between members of the 3D_C12 gene family.

| | 3D_C12 | 7D_A06 | 3D_C12-7 | 3D_C12-10 | 3D_C12-15* |
|---|---|---|---|---|---|
| 7D_A06 | 93.4** | | | | |
| 3D_C12-7 | 93.7 | 94.0 | | | |
| 3D_C12-10 | 93.7 | 94.4 | 99.7 | | |
| 3D_C12-15* | 95.5 | 92.6 | 93.1 | 92.8 | |
| 131A_A02* | 98.0 | 94.0 | 93.4 | 93.1 | 93.1 |

*partial sequences
**numbers indicate percentages

TABLE 3

Predicted amino acid sequence identities between full-length members of the 3D_C12 gene family.

|          | 3D_C12 | 7D_A06 | 3D_C12-7 |
|----------|--------|--------|----------|
| 7D_A06   | 92.3*  |        |          |
| 3D_C12-7 | 92.8   | 94.8   |          |
| 3D_C12-10| 92.5   | 94.4   | 99.6     |

**numbers indicate percentages

In addition to enabling the acquisition of full-length sequence information for the 3D_C12 and 7D_A06 cDNAs, the above described PCR amplifications yielded additional products that were closely related to, yet clearly distinct from, the 3D_C12 and 7D_A06 cDNA sequences. Using a primer directed against a sequence interior to the 3D_C12 cDNA, in combination with a primer specific to pBluescript II, a unique sequence designated 3D_C12-15 (FIG. 3A-3G; SEQ ID NO:9; predicted amino acid sequence shown in SEQ ID NO:10) was amplified in addition to the expected 3D_C12 product. 3D_C12-15 is 95.5% identical to the corresponding DNA sequence of 3D_C12 and 92.6% identical to the same region of 7D_A06 (Table 2).

Because the 3D_C12-15 fragment represented an additional, distinct member of the 3D_C12 gene family, an attempt was made to obtain a full-length cDNA sequence of this gene. A PCR primer specific to the first seven codons of the 3D_C12-15 reading frame was used in combination with a pBluescript II-specific primer in an amplification reaction using our converter cDNA library as template. Sequence analysis of several independent amplification products failed to reveal a full-length 3D_C12-15 gene. Instead, a new member of this family was recovered, designated 3D_C12-7 (FIG. 3A-3G; coding sequence set forth as nt 1-1551 of SEQ ID NO:5). Across the full-length nucleotide sequence shown in SEQ ID NO:5, 3D_C12-7 shares 93.7% nucleotide sequence identity with 3D_C12 (across SEQ ID NO:1), 94.0% nucleotide sequence identity with 7D_A06 (across SEQ ID NO:7), and 93.1% identity over the corresponding region of fragment 3D_C12-15 (SEQ ID NO:9) (Table 2). The predicted amino acid sequence of 3D_C12-7 (SEQ ID NO:6) is 92.8% identical to the 3D_C12 protein (SEQ ID NO:2), and 94.8% identical to the 7D_A06 protein (SEQ ID NO:8) (Table 3).

Two additional members of the 3D_C12 family were also identified. A gene designated 3D_C12-10 (FIG. 3A-3G; coding sequence set forth as nt 1-1551 of SEQ ID NO:3; predicted amino acid sequence set forth in SEQ ID NO:4) was recovered from an amplification reaction using a PCR primer complementary to a sequence in the 3' flanking region of 3D_C12 together with a Bluescript II-specific primer (and the converter library as template). 3D_C12-10 differs at only five nucleotide positions from the 3D_C12-7 nucleotide sequence (SEQ ID NO:5) (FIG. 3A-3G), and at only two amino acids positions from the predicted 3D_C12-7 protein product (SEQ ID NO:6) (FIG. 4).

With the completion of the nonconverter EST database, another member of the 3D_C12 gene family was revealed. The partial DNA sequence of 131 A_A02 (SEQ ID NO: 11; predicted amino acid sequence set forth in SEQ ID NO:12) that is found in this database is 98.0% identical to the corresponding sequence of 3D_C12, and 94.0% identical to the same region of 7D_A06 (FIG. 3A-3G and Table 2). As described in the previous section, 131A_A02 is a member of the 3D_C12 gene family that was represented on the comprehensive unigene chip used in microarray assays as described elsewhere herein.

Example 5

Transgenic Plant Analysis of Members of the 3D_C12 Gene Family

To determine whether members of the 3D_C12 family of cytochrome P450 genes are involved in the metabolic conversion of nicotine to nornicotine, transgenic plants were generated using constructs designed to either enhance or inhibit gene expression. To test the effects of down-regulating gene activity, an RNA interference (RNAi) strategy was employed. A 99-bp region of 3D_C12 located immediately upstream of the stop codon (FIG. 3A-3G), was used to create a construct that would form a dsRNA hairpin within the plant cell. Such dsRNA structures are known to activate an RNAi silencing complex that leads to the degradation of both transgene RNAs and endogenous RNAs that are identical or highly homologous to the sequence found in the dsRNA (Wesley et al. (2001) *Plant J.* 27: 581-590; Waterhouse & Helliwell (2002) *Nat. Gen. Rev.* 4: 29-38).

Given that each member of the 3D_C12 characterized as described herein shares over 90% DNA sequence identity, an RNAi construct synthesized against one member was expected to silence the entire gene family. Specifically, the RNAi construct generated against the 3D_C12 sequence shares sequence identities of 90/99 and 91/99 with the 7D_A06 and 3D_C12-7 cDNAs, respectively, over this region (FIG. 3A-3G). The 3D_C12/RNAi construct (also referred to in Example 7 as the 3D_C12Ri99 construct) was cloned downstream of the constitutive 35S promoter of cauliflower mosiac virus (CaMV) and introduced into the strong converter Burley tobacco line DH 98-325-6 using *Agrobacterium*-mediated transformation.

A hallmark of RNAi-mediated silencing is the marked reduction in steady-state transcript accumulation of the gene whose activity has been down-regulated. To confirm that gene silencing of the 3D_C12 gene family had occurred in the plants showing low nornicotine phenotypes, a Northern blot analysis was conducted using RNAs isolated from three of the transgenic plants possessing 3D_C12/RNAi constructs and displaying low nornicotine phenotypes, two individuals transformed with the 3D_C12/RNAi construct yet still showing high levels of nornicotine, and one of the vector-only control plants.

To assess the affects of overexpression of gene activity, the cDNAs from the three members of the 3D_C12 gene family for which we first obtained full-length sequence information (3D_C12, 7D_A06, and 3D_C12-7) were cloned in their sense orientations downstream of the 35S CaMV promoter. These constructs were subsequently introduced into *N. tabacum* cultivar Petite Havana using *Agrobacterium*-mediated transformation. The Petite Havana line is commonly used by researchers because of its shorter stature and abbreviated generation time in relation to commercial tobacco cultivars. The converter/nonconverter status of the Petite Havana cultivar is unknown, but the alkaloid assays of the present application clearly showed that the plants in our possession were strong converters.

Although the host plants in these experiments were converters, the present strategy was to conduct alkaloid assays on green, non-cured tissue, where minimal nornicotine accumulates in converter and nonconverter plants alike (and the 35S CaMV promoter is very active). In fact, a nonconverter line was purposely chosen because tissue culturing, as required when conducting *Agrobacterium*-mediated transformation, is known to enhance the frequency of genetic conversion and would thus potentially complicate interpretation of results (e.g., assessing whether a novel phenotype was solely attributable to the transgene as opposed to being the result of the plant having undergone genetic conversion).

Results

Given the high degree of variability typically observed among independent transgenic plants transformed with the same transgene construct, 10 independently transformed individuals were selected to assess the effects of the 3D_C12/RNAi construct on the metabolic conversion of nicotine to nornicotine. Leaves from each of the 10 3D_C12/RNAi individuals, in addition to two control plants transformed with the pBI121 vector alone, were treated with ethephon and cured for seven days. Alkaloid analysis of these materials is shown in Table 4.

to be significantly influenced by the presence or absence of the 3D_C12/RNAi transgene (Table 4).

Figure 5:
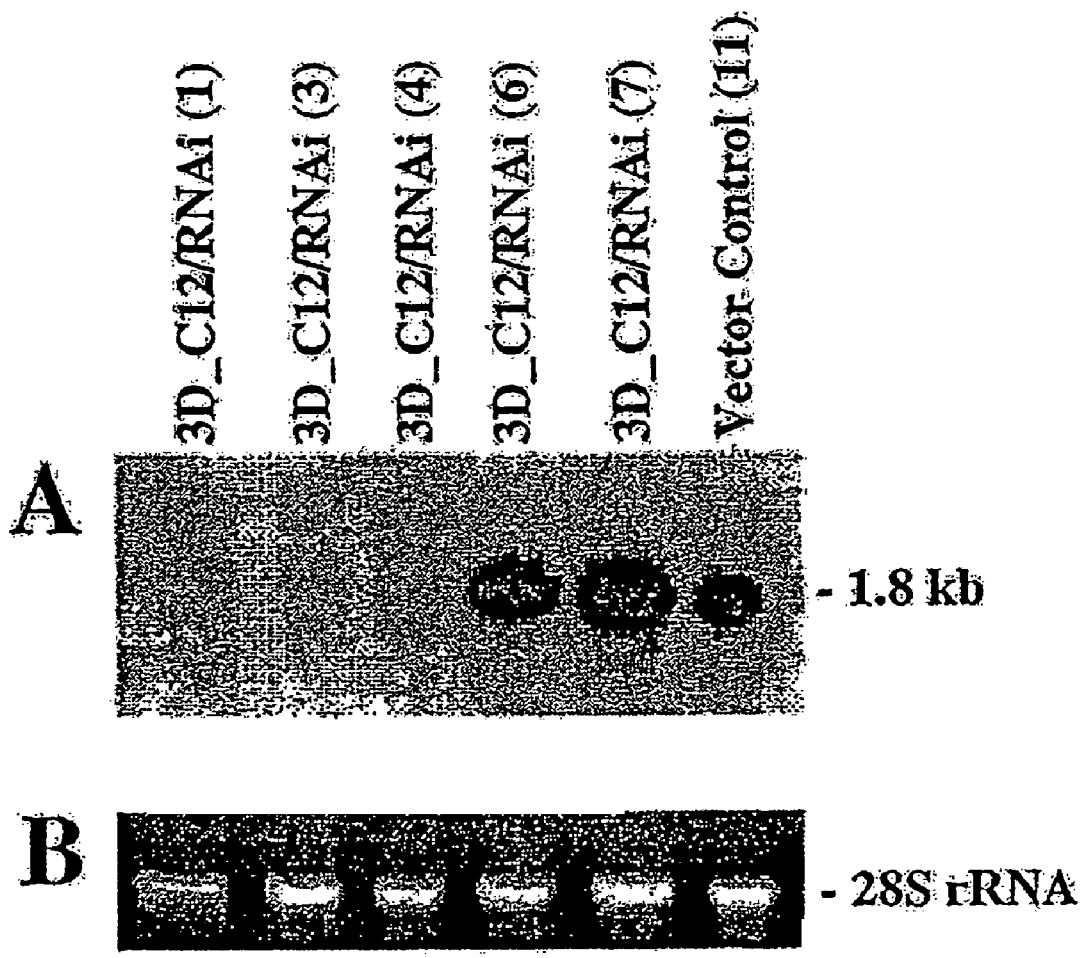
FIG. 5 shows a Northern blot analysis of transgenic plants possessing the 3D_C12/RNAi construct. (A) Hybridization of the 3D_C12-7 probe to RNAs isolated from ethephon-treated, cured leaves of transgenic plants displaying low nornicotine phenotypes (3D_C12/RNAi-1, 3, and 4) and high nornicotine phenotypes (3D_C12/RNAi-6, 7, and vector-only control plant 11). Estimated size of hybridizing band is indicated in kilobases (kb). (B) Ethidium bromide staining of the portion of the gel used in (A) that contains the 28S ribosomal RNA to show the relative equivalence of RNA loading among the lanes.

Although the cDNA insert of the 3D_C12-7 gene was used as the specific hybridization probe, at the hybridization and wash conditions used in this experiment, cross-hybridization to the entire 3D_C12 gene family would be expected. As shown in FIG. 5, a strong hybridization signal was detected in each plant showing a high nornicotine phenotype, and minimal hybridization was detected in the plants transformed with the 3D_C12/RNAi construct that showed a low nornicotine phenotype. We thus conclude that the effective silencing of the 3D_C12 gene family inhibits the metabolic conversion of nicotine to nornicotine in tobacco.

Alkaloid analysis of the Petite Havana transgenic plants is shown in Table 5. Four independently transformed plants containing the 35S:3D_C12 and 35S:3D_C12-7 constructs were tested along with seven independent 35S:7D_A06 individuals and three plants independently transformed with the pBI121 control vector. As expected, the green, non-cured

TABLE 4

Alkaloid analysis of DH 98-325-6 plants independently transformed with the 3D_C12/RNAi construct (and pBI121 vector control). Leaves were treated with ethephon and cured for seven days.

| Sample | % Nicotine* | % Nornicotine* | % Anabasine* | % Anatabine* | % Conversion** |
|---|---|---|---|---|---|
| 3D_C12 RNAi (1) | 3.149 | 0.100 | 0.012 | 0.159 | 2.8 |
| 3D_C12 RNAi (2) | 2.569 | 0.193 | 0.009 | 0.110 | 7.0 |
| 3D_C12 RNAi (3) | 2.175 | 0.064 | 0.007 | 0.080 | 2.9 |
| 3D_C12 RNAi (4) | 3.517 | 0.125 | 0.012 | 0.139 | 3.4 |
| 3D_C12 RNAi (5) | 1.085 | 0.868 | 0.009 | 0.119 | 44.4 |
| 3D_C12 RNAi (6) | 0.025 | 2.260 | 0.011 | 0.122 | 98.9 |
| 3D_C12 RNAi (7) | 0.027 | 1.867 | 0.011 | 0.122 | 98.6 |
| 3D_C12 RNAi (8) | 2.268 | 0.128 | 0.009 | 0.102 | 5.3 |
| 3D_C12 RNAi (9) | 2.197 | 0.133 | 0.008 | 0.099 | 5.7 |
| 3D_C12 RNAi (10) | 2.434 | 0.112 | 0.009 | 0.110 | 4.4 |
| vector control (3) | 1.811 | 1.1735 | 0.018 | 0.170 | 48.9 |
| vector control (11) | 0.290 | 2.090 | 0.013 | 0.143 | 87.8 |

*percentage of leaf dry weight
**[% nornicotine/(% nicotine + nornicotine)] × 100

Typical of line DH 98-325-6, ethephon treatment and curing resulted in substantial nornicotine production in the two control plants (48.9% and 87.8% conversion of nicotine to nornicotine). In dramatic contrast, seven of the ten independent transgenic plants possessing the 3D_C12/RNAi construct displayed minimal nicotine to nornicotine conversion, with conversion percentages ranging from 2.8 to 7.0 percent. The other three 3D_C12/RNAi lines displayed alkaloid contents similar to the vector-only control plants. Concentrations of the minor alkaloids anabasine and anatabine did not appear leaves of the three vector-only control plants contained minimal amounts of nornicotine. Likewise, all plants transformed with the 35S:3D_C12 and 35S:7D_A06 constructs showed minimal metabolic conversion of nicotine to nornicotine. A very different phenotype, however, was observed with plants transformed with 35S:3D_C12-7. All four plants independently transformed with this construct contained nornicotine as the predominant alkaloid in the green, nontreated leaf; nicotine to nornicotine conversion percentages ranged from 94.6 to 98.6.

TABLE 5

Alkaloid analysis of individual Petite Havana plants transformed with 3D_C12, 3D_C12-7, 7D_A06 constructs or the pBI121 vector control. Green leaves were harvested and analyzed without treatment or curing.

| Sample | % Nicotine* | % Nornicotine* | % Anabasine* | % Anatabine* | % Conversion** |
|---|---|---|---|---|---|
| vector control (2) | 0.673 | 0.018 | 0.006 | 0.018 | 2.6 |
| vector control (8) | 0.605 | 0.014 | 0.005 | 0.016 | 2.3 |
| vector control (10) | 0.694 | 0.017 | 0.004 | 0.018 | 2.4 |
| 35S:3D_C12 (1) | 0.706 | 0.005 | 0.006 | 0.020 | 0.7 |
| 35S:3D_C12 (2) | 0.814 | 0.022 | 0.007 | 0.017 | 2.6 |
| 35S:3D_C12 (3) | 0.630 | 0.010 | 0.003 | 0.012 | 1.6 |
| 35S:3D_C12 (4) | 0.647 | 0.010 | 0.004 | 0.011 | 1.5 |

TABLE 5-continued

Alkaloid analysis of individual Petite Havana plants transformed with 3D_C12,
3D_C12-7, 7D_A06 constructs or the pBI121 vector control.
Green leaves were harvested and analyzed without treatment or curing.

| Sample | % Nicotine* | % Nornicotine* | % Anabasine* | % Anatabine* | % Conversion** |
|---|---|---|---|---|---|
| 35S:3D_C12-7 (1) | 0.005 | 0.347 | 0.002 | 0.012 | 98.6 |
| 35S:3D_C12-7 (2) | 0.006 | 0.255 | 0.002 | 0.009 | 97.4 |
| 35S:3D_C12-7 (3) | 0.017 | 0.300 | 0.002 | 0.010 | 94.6 |
| 35S:3D_C12-7 (4) | 0.010 | 0.384 | 0.002 | 0.015 | 97.5 |
| 35S:7D_A06 (1) | 0.761 | 0.011 | 0.005 | 0.018 | 1.4 |
| 35S:7D_A06 (2) | 0.507 | 0.009 | 0.003 | 0.007 | 1.7 |
| 35S:7D_A06 (4) | 0.653 | 0.015 | 0.006 | 0.015 | 2.2 |
| 35S:7D_A06 (5) | 0.643 | 0.013 | 0.004 | 0.018 | 2.0 |
| 35S:7D_A06 (6) | 0.521 | 0.007 | 0.004 | 0.014 | 1.3 |
| 35S:7D_A06 (7) | 0.716 | 0.015 | 0.005 | 0.020 | 2.1 |
| 35S:7D_A06 (8) | 0.701 | 0.027 | 0.004 | 0.018 | 3.7 |

*percentage of leaf dry weight
**[% nornicotine/(% nicotine + nornicotine)] × 100

Example 6

Cosuppression of the 3D_C12 Gene Family

In addition to the major conclusion that the 3D_C12-7 gene was capable of mediating nicotine to nornicotine conversion, one additional observation stood out in the alkaloid analyses of the Petite Havana transgenic plants. The alkaloid results reported in Table 5 together with additional alkaloid assays conducted independently (data not shown) consistently showed one of the plants transformed with the 35S:3D_C12 construct (35S:3D_C12(1)) as having less nornicotine in the green, nontreated leaf than any other plant in this study. This may be the result of cosuppression of the 3D_C12 gene family in this specific plant, a phenomenon frequently observed in transgenic plants even when a transgene is expressed in its sense orientation (Fagard and Vaucheret (2000) *Annu. Rev. Plant Physiol. Plant Mol. Biol.* 51: 167-194).

If plant 35S:3D_C12 (1) was truly displaying a cosuppression phenotype, this phenotype would be expected to be maintained even upon ethephon treatment and curing of the leaves, similar to the low nornicotine phenotypes conferred by the 3D_C12/RNAi construct in the converter genotype DH 98-325-6 as described above. To test this prediction, alkaloid profiles were determined on ethephon treated, cured leaves of 35S:3D_C12 (1) and two vector-only control plants. As shown in Table 6, ethephon treatment and curing resulted in over 97% nicotine to nornicotine conversion in the two control plants whereas similarly treated 35S:3D_C12 (1) leaves displayed negligible conversion (0.6%). Leaves from five other plants expressing either 35S:3D_C12 and 35S:7D_A06 transgenes were also subjected to ethephon treatment and curing. In each case a high nornicotine phenotype was observed, similar to the vector-only control plants (data not shown).

TABLE 6

Alkaloid analysis of 35S:3D_C12 (1) and pBI121 vector controls plants.
Leaves were treated with ethephon cured for seven days.

| Sample | % Nicotine* | % Nornicotine* | % Anabasine* | % Anatabine* | % Conversion** |
|---|---|---|---|---|---|
| vector control (8) | 0.009 | 0.425 | n.d. | 0.011 | 97.9 |
| vector control (10) | 0.008 | 0.560 | n.d. | 0.025 | 98.6 |
| 35S:3D_C12 (1) | 1.185 | 0.007 | n.d. | 0.020 | 0.6 |

Figure 6:
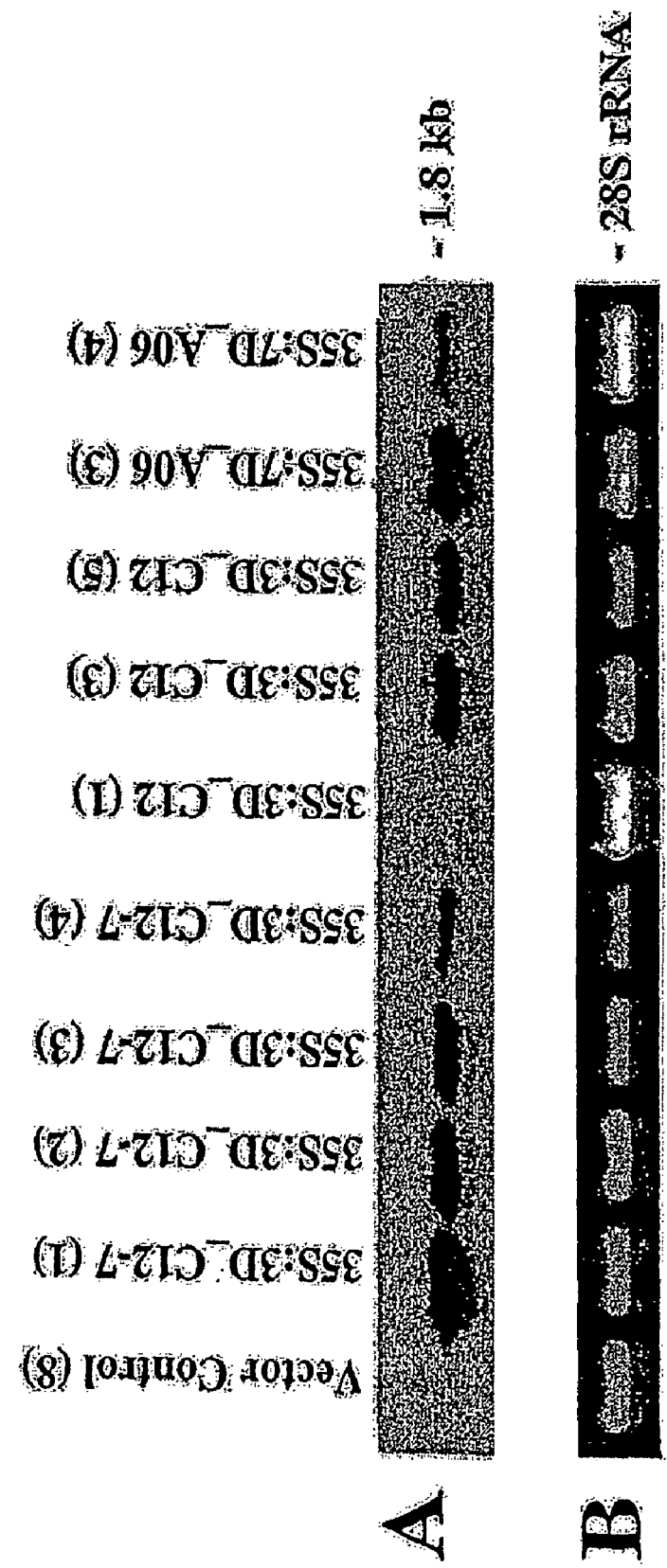
FIG. 6 shows a Northern blot analysis of transgenic plants possessing sense-orientation constructs of members of the 3D_C12 gene family. (A) Hybridization of the 3D_C12-7 probe to RNAs isolated from nontreated leaves of independent transgenic lines expressing 3D_C12-7, 3D_C12, and 7D_A06 constructs and a vector-only control (control 8). Estimated size of hybridizing band is indicated in kilobases (kb). (B) Ethidium bromide staining of the portion of the gel used in (A) that contains the 28S ribosomal RNA to show the relative equivalence of RNA loading among the lanes.

*percentage of leaf dry weight
**[% nornicotine/(% nicotine + nornicotine)] × 100
n.d., not detected Finally, Northern blot assays were conducted on select plants representing each of the Petite Havana transgenic genotypes (FIG. 6). Using a 3D_C12-7 cDNA as a hybridization probe, minimal signal was detected with RNAs isolated from green, nontreated leaves of the vector-only control plant. In contrast, hybridization was easily detected in RNA samples from all four independent transgenic plants possessing the 35S:3D_C12-7 construct. A strong hybridization signal was similarly observed using RNAs from all other transgenic plants tested that were transformed with the 35S:3D_C12 and 35S:7D_A06 constructs, with the exception of the low nornicotine containing plant 35S:3D_C12 (1).

Overall results of the Northern blotting assays show that the 35S CaMV promoter was generally effective in mediating a high level of gene expression for each of the three members of the 3D_C12 gene family tested in this study. Failure to detect a hybridization signal in plant 35S:3D_C12 (1) is con- Example 7

Additional Characterization and Suppression of Additional 3D_C12 Genes

Figure 8:
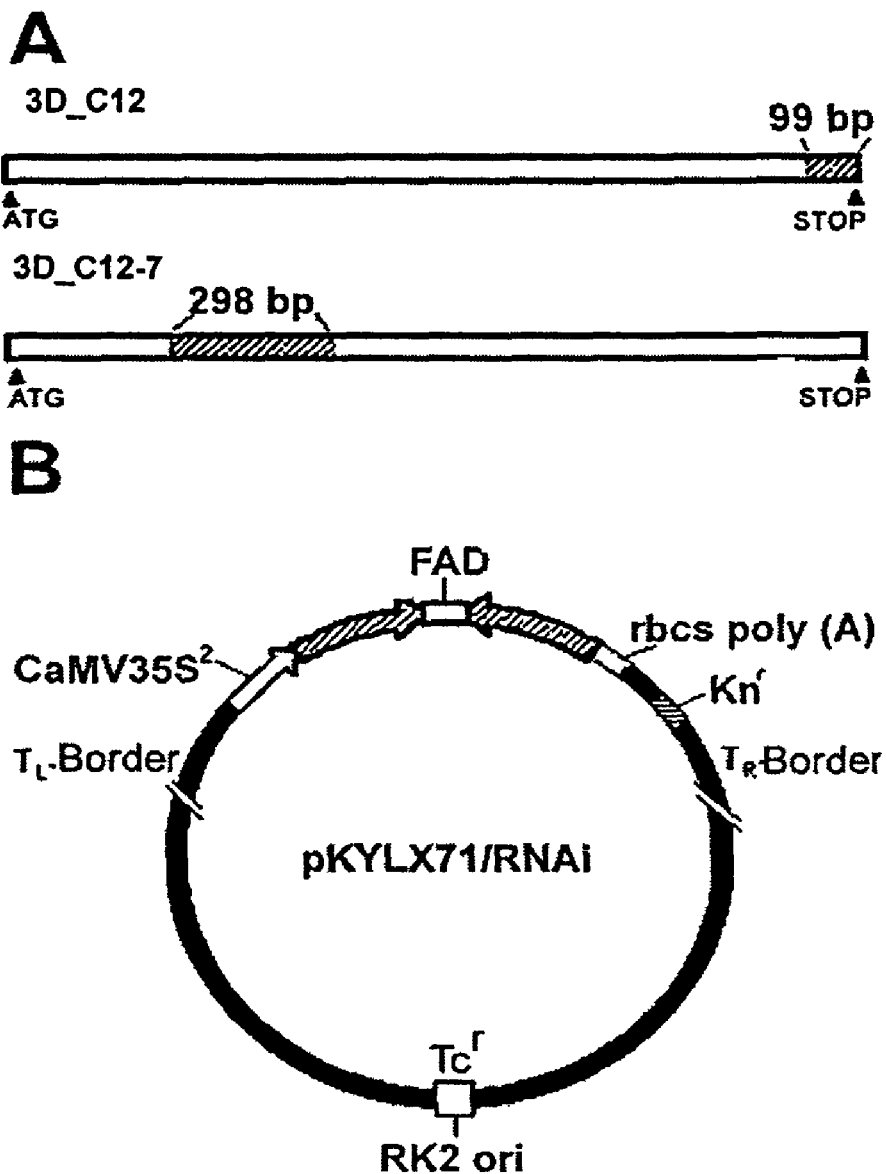
FIG. 8A shows a diagram of the RNAi constructs used to silence expression of members of the 3D_CD12 gene family.
FIG. 8B shows a diagram of the RNAi binary expression vector, pKYLX71/RNAi.

A second RNAi construct was prepared using polynucleotide sequences from the 3D_C12-7 sequence. The assembly of the 3D_C12-7/RNAi expression cassette followed the same basic steps as those outlined for 3D_C12/RNAi above. Briefly, a 298-bp sense and antisense strand of the 3D_C12-7 cDNA (SEQ ID NO:5) corresponding to the region between nucleotide positions 297 and 594 of the coding sequence (positions 1-1551 of SEQ ID NO:5) were ligated into the pKYLX801 vector downstream and upstream of the 151-bp soybean omega-6 fatty acid desaturase intron (see GenBank Accession No. DQ672337), respectively. The primers (E4SFwd and E4SRev) used for the isolation of the 298-bp region by sense and antisense arms were 5'-AAGCTTTGACGCCATTTTTTCCAATCG-3' (SEQ ID NO:27), and 5'-CTCGAGTTTTCCAGCGATCATCT-TCAC-3'(SEQ ID NO:28), respectively. The RNAi cassette was excised from pKYL801 and placed between a strong CaMV35S$^2$ promoter and a rubisco small subunit terminator of the binary plant expression vector, pKYLX71 (see FIG. 8). In the discussions below, this RNAi construct is referred to as the 3D_C12-7-Ri298 construct.

Transgenic tobacco plants were generated via *Agrobacterium*-mediated transformation following the procedures provided above. Briefly, transformed burley tobacco plants were regenerated from calli on Murashige-Skoog (MS) medium supplemented with 100 mg/L kanamycin and plant hormones in a growth room maintained at 25° C. under a 16 hr/8 hr light/dark cycle. Calli were transferred to fresh selection media every 2-3 weeks until shoots appeared. Small shoots were transferred to rooting media to allow root development for 2 weeks. Fully regenerated plants were transferred to a greenhouse and grown under standard conditions.

SYBR® Green I Chemistry

Total RNA was isolated from cured leaves of converter and nonconverter burley tobacco plants using the TRIzol® reagent (Invitrogen, Life Technologies, Carlsbad, Calif.). Purified RNA was treated with RNase-free DNase (TURBO DNA-free™, Ambion, Austin, Tex.). First strand cDNA was synthesized using 5 µg of total RNA and the StrataScript® First-Strand Synthesis System (Stratagene, Cedar Creek, Tex.). Relative quantitative RT-PCR was employed for determining the abundance of the 3D_C12-7 cDNA using SYBR® Green I fluorescence chemistry Morrison et al. (1998) *Biotechniques* 24:954-962.

A calibration curve was generated with a serial dilution of the 3D_C12-7 cDNA cloned into the pGEM®-T Easy vector (Promega Corporation, Madison, Wis.). The RT-PCR mixture contained 2.5 mM MgCl$_2$, 125 µM each dNTP, 0.5 µM each primer, 0.5×SYBR® Green I, 0.5 µg cDNA (or 1 µl reference plasmid), and 1.25 U Platinum Taq polymerase (Invitrogen Life Technologies). The sequences of the allele-specific 3D_C12-7 primers (E4SyFwd and E4SyRev) were 5'-ACGT-GATCCTAAACTCTGGTCTG-3' (E4SyFwd (SEQ ID NO:29)) and 5'-GCCTGCACCTTCCTTCATG-3' (E4SyRev (SEQ ID NO:30)). RT-PCR was performed in a BioRad iCycler thermocycler (BioRad Laboratories, Hercules, Calif.) set to the following protocol: 95° C. for 2 min; 35 cycles of 95° C. for 30 sec, 55° C. for 30 sec 72° C. for 50 sec, followed by final extension at 72° C. for 5 min. A 165-bp fragment of the α-tubulin gene was used as an internal standard. 3D_C12-7 cDNA concentration was determined from the transcript-specific calibration curve and normalized to the internal standard. Fold-induction was calculated by dividing the normalized fluorescence values of the converter by the nonconverter samples. Melting-curve analysis was used to confirm the purity of PCR products as described in Ririe et al. (1997) *Anal. Biochem.* 245:154-160. Two plants were sampled per treatment and amplifications were repeated three times.

Taqman® Chemistry

Total RNA was isolated from tobacco lines using TRIzol reagent. Purified RNA was treated with RNase-free DNase (TURBO DNA-free™). First strand cDNA was synthesized using 10 µg of total RNA and the High Capacity cDNA Archive Kit (Applied Biosystems, Foster City, Calif.). The RT-PCR mixture contained 1× TaqMan® Universal PCR Master Mix (Applied Biosystems, Foster City, Calif.), 400 nM of each primer (E4TmFwd and E4TmRev), 250 nM TaqMan® minor groove binder (MGB) probe (E4MGB), 2 ng of cDNA, and nuclease-free water (Afonina et al. (2002) *Biotechniques* 32:940-949). The primer and probe sequences were 5'-CGGTAATCGGCCATCTTTTC-3' (E4TmFwd (SEQ ID NO:31)), 5'-CCGAGTTTTCGAGCTAATGGA-3' (E4TmRev (SEQ ID NO:32)), and 5'-CAATGACGAACG-GCGACAG-3' (MGB probe (SEQ ID NO:33)). RT-PCR was performed in an ABI 7500 Real-Time System (Applied Biosystems, Foster City, Calif.) set to the following protocol: 50° C. for 2 min; 95° C. for 10 min; 40 cycles of 95° C. for 15 sec, 60° C. for 1 min. Glyceraldehyde-3-phosphate dehydrogenase (G3PDH) was used as the endogenous control to normalize the amount of cDNA template in the reactions. Fold-change was determined by dividing the normalized fluorescence values of each sample by those obtained from a nonconverter or uncured control sample. For each treatment, RNA was isolated from three independent plants and amplifications were repeated 3 times per RNA sample.

Northern and Southern Blot Analyses

Total RNA was isolated from cured tobacco leaves using the TRIzol reagent according to the manufacturer's instructions (Invitrogen, Life Technologies). Total RNA samples were separated on 1.2% TBE agarose gel, and transferred to positively charged nylon membranes by electroblotting with 2×TBE buffer. Membranes were UV crosslinked and washed in 2×SSC for 5 min. Northern blot hybridization, washing, and detection were carried out using the digoxigenin (DIG) System as described by the manufacturer (Roche Diagnostics Corp., Indianapolis, Ind.). The 1.8 kb full-length ORF of the 3D_C12-7 cDNA was labeled with DIG and used as a probe.

Genomic DNA was extracted with DNAzol® (Invitrogen, Life Technologies) from green tobacco leaves according to manufacturer's protocol. After incubation with FcoRI or NcoI restriction enzymes overnight, 15 µg of the digested DNA was separated on 0.7% TBE agarose gel, depurinated with 0.25 M HCl for 10 min, and denatured with 0.5 N NaOH for 30 minutes. DNA was blotted overnight by capillary transfer onto positively charged nylon membranes (Roche Diagnostics Corp.) and hybridized at 65° C. overnight with a 515-bp DIG-labeled fragment of the neomycin phosphotransferase II (NPT II) gene. Hybridization, washing, and detection were performed according to the protocols supplied with the DIG System. The primers used for the amplifications of the Northern and Southern hybridization probes were E4FIFwsd (5'-ATGGTTTTTCCCATAGAAGCC-3' (SEQ ID NO:34)), E4FIRev (5'-TTTTTGGGACAATCAGTCAAT-3' (SEQ ID NO:35)), KanFwd (5'-TGAATGAACTGCAG- GACGAG-3' (SEQ ID NO:36)), and KanRev (5'-AATAT-CACGGGTAGCCAACG-3' (SEQ ID NO:37)).

Alkaloid Analysis

Tobacco leaves were harvested and air dried in an oven at 50° C. for 2 days. A 100 mg sample of crushed, dried leaf is added to 0.5 ml of 2 N NaOH in a 20 ml scintillation vial. The sample was mixed and allowed to incubate for 15 minutes at room temperature. Alkaloids were extracted by the addition of 5 ml of extraction solution [0.04% quinoline (wt/vol) dissolved in methyl-t-butyl ether] and gently rotated on a linear shaker for 3 hours. Following phase separation, an aliquot of the organic phase was transferred to a sample vial. Samples were analyzed using a PerkinElmer Autosystem XL (PerkinElmer, Boston, Mass.) gas chromatograph equipped with a flame ionization detector, a 4 mm split/splitless glass liner and a 30 m×0.53 mm ID DB-5 column. Chromatographic conditions were as follows: detector temperature: 250° C.; injector temperature: 250° C.; helium flow at 120° C.: 20 ml/min; injection volume: 2 µl; column conditions: 120°, hold 1 min, 20-280° C. at 30° C./min ramping rate, hold at 280° C. for 2 min. Alkaloid composition was determined by the TotalChrome Navigator software using a calibration curve. Means of the alkaloid measurements were separated according to Fisher's Protected LSD (PROC MIXED).

Plants

Double haploid burley tobacco lines DH 98-325-5 (325-5; nonconverter) and DH98-325-6 (325-6; converter) described above were used in all experiments, except for the fluorogenic 5' nuclease (TaqMan®) chemistry-based RT-PCR assays where the isogenic DH 91-1307-46 (nonconverter) and DH 91-1307-46 (converter) lines were used. All plants were grown in a controlled environment greenhouse equipped with supplemental lighting providing, a 14 hr/10 hr light/dark cycle.

For curing, tobacco leaves were collected from converter and nonconverter plants about 1 month before flowering and treated by dipping each leaf twice for 10 sec, into 2% ethephon and dried for 2 hours. Leaves were cured for up to two weeks in plastic bags, under dark conditions, until they turned yellow. Cured leaves were used for the Northern and alkaloid analyses. Samples of cured leaves subjected to GC analysis were dried at 50° C. for 2 days. For Southern analysis, green tobacco leaves of adult plants were used. To produce $T_1$ generation transgenic plants, primary transformants ($T_0$) were self-pollinated, and the harvested $T_1$ seed was screened by germinating seedlings on MS-agar plates containing 100 mg/L kanamycin for 6 weeks. Survivors were transplanted to soil and grown in a greenhouse as described above. Plants were fertilized with Peter's Professional All Purpose Plant Food (20-20-20; Spectrum Brands Inc., Madison, Wis.) once a week.

RT-PCR Analysis of 3D_C12-7 Expression in Converter and Nonconverter Tobacco

To further characterize the role of 3D_C12-7 in nicotine N-demethylation, experiments were performed to demonstrate that the regulation of 3D_C12-7 expression is consistent with the levels of nicotine N-demethylation activity observed in converter versus nonconverter tobacco.

To determine the rate of 3D_C12-7 mRNA accumulation in converter and nonconverter tobacco, an allele-specific real-time RT-PCR strategy was employed. Because RT-PCR involves the detection and measurement of the amplification products of a PCR template, the use of allele-specific primers allows the quantification of a single isoform among a group of highly homologous sequences. For accurate quantification of the 3D_C12-7 transcript, two different segments of the 3D_C12-7 coding region were amplified and both SYBR® Green and TaqMan® chemistries were used to generate fluorescence signals. RT-PCR analysis using the SYBR® Green I chemistry revealed an 80-fold increase in the levels of the 3D_C12-7 transcript in the cured leaves of converter versus nonconverter tobacco. A single peak melting curve and gel electrophoretic analyses of the amplicons confirmed the homogeneity of the PCR products.

In the TaqMan® chemistry-based RT-PCR experiment, 3D_C12-7 transcript levels were quantified in untreated and ethephon-treated converter and nonconverter tobacco leaves that were cured for 0, 1 or 5 days. Low levels of 3D_C12-7 transcripts were detected in the uncured leaves or following a 1-day curing period regardless of conversion type or ethephon treatment. Similarly, base line levels of 3D_C12-7 transcription were observed in converter or nonconverter leaves that were cured for 5 days without ethephon treatment. In contrast, a 7.5-fold increase in 3D_C12-7 transcript accumulation was detected in the cured leaves of converter versus nonconverter tobacco, and a 70-fold increase was observed in the uncured versus cured leaves of a converter tobacco variety when ethephon treatment preceded the 5-day curing period. While not intending to be limited by any particular theory, these results suggest that 3D_C12-7 is a major contributor to nicotine N-demethylation and is strongly inducible by ethylene in senescing tobacco leaves.

Suppression of Nicotine to Nornicotine Conversion by the 3D_C12-Ri99 and 3D_C12-7-Ri298 Constructs To compare the extent to which 3D_C12 and 3D_C12-7 mediate the suppression of nornicotine production, converter and nonconverter burley tobacco plants were transformed with the two gene silencing vectors. Ten (10) transgenic plants were regenerated per RNAi construct. About 80% of tobacco plants overexpressing either the 99-bp or 298-bp inverted repeat showed reduced nornicotine levels compared to the empty vector controls (Tables 7 and 8). In the nonconverter genotype, 3D_C12-Ri99 and 3D_C12-7-Ri298 expression reduced nicotine to nornicotine conversion by about 1.8-fold (2.0%) and 3.0-fold (1.2%), respectively, in comparison to the rate of conversion detected in the vector controls (3.6%) (Table 7). Among the silenced nonconverter plants, the lowest conversion level of 0.9% was achieved using the 3D_C12-7-Ri298 construct (Table 7).

TABLE 7

Alkaloid analysis of nonconvertor burley tobacco plants transformed with the 3D_C12-Ri99 or 3D_C12-7-Ri298 construct.

| Line$^c$ | % Nicotine$^d$ | % Nornicotine$^d$ | % Conversion$^e$ |
| --- | --- | --- | --- |
| 3D-C12-Ri99 | | | |
| 1 | 1.693 | 0.034 | 2.0 |
| 2 | 1.435 | 0.031 | 2.1 |
| 3 | 2.095 | 0.043 | 2.0 |
| 4 | 2.868 | 0.053 | 1.8 |
| 5 | 0.947 | 0.025 | 2.6 |
| 6 | 2.357 | 0.043 | 1.8 |
| 7 | 2.599 | 0.043 | 1.6 |
| 8 | 0.796 | 0.020 | 2.4 |
| 9 | 2.178 | 0.039 | 1.8 |
| 10 | 3.162 | 0.061 | 1.9 |
| MEAN | 2.013 | 0.039 | 2.0a |
| STE | 0.748 | 0.012 | 0.3 |
| 3D_C12-7-Ri298 | | | |
| 3 | 1.806 | 0.020 | 1.1 |
| 4 | 1.948 | 0.207 | 1.4 |

TABLE 7-continued

Alkaloid analysis of nonconvertor burley tobacco plants transformed with the 3D_C12-Ri99 or 3D_C12-7-Ri298 construct.

| Line[c] | % Nicotine[d] | % Nornicotine[d] | % Conversion[e] |
|---|---|---|---|
| 5 | 2.061 | 0.020 | 1.0 |
| 6 | 2.704 | 0.040 | 1.5 |
| 8 | 2.652 | 0.023 | 0.9 |
| 9 | 1.074 | 0.015 | 1.3 |
| MEAN | 2.041 | 0.024 | 1.2b |
| STE | 0.550 | 0.008 | 0.2 |
| Vector Control[g] | | | |
| 1 | 1.206 | 0.052 | 4.2 |
| 2 | 1.265 | 0.038 | 2.9 |
| 3 | 1.752 | 0.058 | 3.2 |
| 4 | 1.230 | 0.072 | 5.6 |
| 5 | 1.777 | 0.060 | 3.3 |
| 6 | 1.536 | 0.044 | 2.8 |
| MEAN | 1.461 | 0.054 | 3.6c |
| STE | 0.240 | 0.011 | 1.0 |

[a]Tobacco leaves were treated with ethephon and cured for 2 weeks at 25° C.
[b]Of the plants transformed with an RNAi construct, only silenced individuals are shown. Alkaloid data represent the means of 2 measurements.
[c]Numbers represent independently transformed individuals.
[d]Percentage of leaf dry weight.
[e][% nornicotine/(% nicotine + % nornicotine)] × 100; values followed by different letters are significantly different according to Fisher's Protected LSD (0.05).
[f]STE, standard error
[g]Tobacco plants transformed with only pKYLX71 vector were used as controls.

Relative to nonconverter tobacco, nornicotine accumulation was suppressed even more dramatically in the silenced individuals of the strong converter plants (Table 8). Using 3D_C12-Ri99 constructs, nicotine conversion was reduced to levels as low as 4.5% in 3D_C12-Ri 99-transformed 325-6 tobacco plants in sharp contrast to the 325-6 control plants exhibiting about 98% conversion rates; Table 8). However, using the 3D_C12-7-Ri298 construct even greater reductions in nicotine conversion were obtained (Table 8). Four 3D_C12-7-Ri298-transformed individuals converted as low as 0.8% of their nicotine to nornicotine, and the arithmetic mean across the 9 silenced transformants was 0.9% conversion. All silenced plants were morphologically indistinguishable from both the empty vector and wild-type controls (data not shown).

TABLE 8

Alkaloid analysis of convertor burley tobacco plants transformed with the 3D_C12-Ri99 or 3D_C12-7-Ri298 construct.

| Line[c] | % Nicotine[d] | % Nornicotine[d] | % Conversion[e] |
|---|---|---|---|
| 3D_C12-Ri99 | | | |
| 1 | 3.419 | 0.100 | 2.8 |
| 2 | 2.569 | 0.193 | 7.0 |
| 3 | 2.175 | 0.064 | 2.9 |
| 4 | 3.517 | 0.125 | 3.4 |
| 8 | 2.268 | 0.128 | 5.3 |
| 9 | 2.197 | 0.133 | 5.7 |
| 10 | 2.434 | 0.112 | 4.4 |
| MEAN | 2.654 | 0.122 | 4.5a |
| STE[g] | 0.573 | 0.039 | 1.6 |
| 3D_C12-7-Ri298[b] | | | |
| 1 | 2.043 | 0.020 | 1.0 |
| 2 | 3.427 | 0.026 | 0.8 |
| 3 | 2.603 | 0.020 | 0.8 |
| 5 | 2.427 | 0.030 | 1.2 |
| 6 | 2.106 | 0.021 | 1.0 |
| 7 | 1.412 | 0.015 | 1.1 |
| 8 | 3.328 | 0.028 | 0.8 |
| 9 | 1.493 | 0.015 | 1.0 |
| 10 | 2.065 | 0.018 | 0.8 |
| MEAN | 2.323 | 0.021 | 0.9b |
| STE | 0.669 | 0.005 | 0.1 |
| Vector Control[h,i] | | | |
| 1 | 0.126 | 1.550 | 92.5 |
| 2 | 0.330 | 2.604 | 88.8 |
| 3 | 0.060 | 1.419 | 95.9 |
| 4 | 0.114 | 1.267 | 91.7 |
| 5 | 0.119 | 1.303 | 91.6 |
| MEAN | 0.150 | 1.628 | 92.1c |
| STE | 0.093 | 0.498 | 2.3 |

[a]Tobacco leaves were treated with ethephon and cured for 2 weeks at 25° C.
[b]Of the plants transformed with an RNAi construct, only silenced individuals are shown.
[c]Numbers represent independently transformed individuals.
[d]Percentage of leaf dry weight.
[e][% nornicotine/(% nicotine + % nornicotine)] × 100; values followed by different letters are significantly different according to Fisher's Protected LSD (0.05).
[f]STE, standard error
[g]Tobacco plants transformed with only pKYLX71 vector were used as controls.

To test the heritability of nornicotine suppression in the 3D_C12-7-Ri298-transformed plants, a set of 3D_C12-7-Ri298-transformed converter and nonconverter lines that displayed the lowest levels of nicotine conversion were advanced to the $T_1$ generation (Table 9). Because segregation of the transgene(s) occurs in the $T_1$ progeny, transgenic individuals were identified by selecting seedlings capable of growing on kanamycin-containing media. Nine kanamycin-resistant progenies of each selected $T_0$-generation 3D_C12-7-Ri298 transformant and four kanamycin-resistant individuals from each selected vector control line were analyzed for alkaloid content. The rate of nicotine conversion did not differ significantly between the primary 3D_C12-7-Ri298 transformants and their $T_1$ progeny, indicating high heritability of the nornicotine suppression trait (see Tables 7, 8, and 9). However, advancing the "nonconverter" vector control line by a single generation increased the nicotine to nornicotine conversion rate from 4.2% to an average value of 11.6%, illustrating the high degree of instability of the conversion locus in transgenic plants lacking the 3D_C12-7-Ri298-specific RNAi construct (Tables 7 and 9). Overall, these results show that RNAi-mediated silencing of the 3D_C12 gene subfamily is a highly effective means of lowering nornicotine production in both nonconverter and strong converter tobacco plants.

TABLE 9

Alkaloid analysis of $T_1$-generation 3D_C12-7-Ri298 transformants.

| Line | % Nicotine[c] | % Nornicotine[c] | % Conversion[d] |
|---|---|---|---|
| DH98-325-5 (nonconverter) | | | |
| 3D_C12-7-Ri298#3 | | | |
| Mean | 1.764 | 0.024 | 1.4a |
| STE | 0.456 | 0.004 | 0.3 |
| 3D_C12-7-Ri298#5 | | | |
| Mean | 1.500 | 0.020 | 1.3a |
| STE | 0.306 | 0.006 | 0.3 |

TABLE 9-continued

Alkaloid analysis of $T_1$-generation 3D_C12-7-Ri298 transformants.

| Line | % Nicotine[c] | % Nornicotine[c] | % Conversion[d] |
|---|---|---|---|
| 3D_C12-7-Ri298#8 | | | |
| Mean | 1.772 | 0.020 | 1.2a |
| STE | 0.409 | 0.003 | 0.3 |
| Vector Control#1[e] | | | |
| Mean | 1.466 | 0.203 | 11.6b |
| STE | 0.713 | 0.161 | 9.7 |
| DH98-325-6 (converter) | | | |
| 3D_C12-7-Ri298#2 | | | |
| Mean | 1.970 | 0.019 | 1.0a |
| STE | 0.536 | 0.004 | 0.3 |
| 3D_C12-7-Ri298#8 | | | |
| Mean | 1.623 | 0.022 | 1.3a |
| STE | 0.300 | 0.002 | 0.2 |
| 3D_C12-7-Ri298#10 | | | |
| Mean | 1.419 | 0.017 | 1.3a |
| STE | 0.515 | 0.004 | 0.3 |
| Vector Control#2[e] | | | |
| Mean | 0.028 | 1.170 | 97.6c |
| STE | 0.006 | 0.234 | 0.5 |

[a]Tobacco leaves were treated with ethephon and cured for 2 weeks at 25° C.
[b]Means and standard errors (STE) represent 9 and 4 $T_1$ progenies of the 3D_C12-7-Ri298 construct and empty vector-transformed (vector control) lines, respectively.
[c]Percentage of leaf dry weight.
[d][% nornicotine/(% nicotine + % nornicotine)] × 100; values followed by different letters are significantly different according to Fisher's Protected LSD (0.015).
[e]Tobacco plants transformed with only pKYLX71 vector were used as controls.

Furthermore, transforming tobacco with the 3D_C12-7-298 construct conferred a 3.6-fold reduction in nicotine conversion relative to typical nonconverter control plants without affecting plant growth and development.

To demonstrate that the down-regulation of nornicotine production in 3D_C12-7-298-transformed tobacco was concomitant with a reduction of the 3D_C12 gene subfamily transcripts, a 3D_C12-7 cDNA probe was hybridized to the total RNA isolated from cured leaves of nonconverter and converter plants. A weak hybridization signal was generated by the RNA isolated from 3D_C12-7-Ri298 transformants displaying low nornicotine content in contrast to the strong signal produced by the RNA extracted from plasmid control or wild-type plants. These results indicate that the down-regulation of nicotine conversion was a result of RNAi-mediated gene silencing of the nicotine N-demethylase gene(s).

Determination of Transgene Copy Number

To determine whether the integration of multiple 3D_C12-7-Ri298 copies were required for producing transplants displaying very low nicotine N-demethylase activity, Southern analysis was performed on selected individuals exhibiting <1.5% nornicotine accumulation. The number of transgenes varied widely among these plants including individuals containing 1 copy (325-5, lines 5 & 8; 325-6, lines 2 & 8), 5 copies (325-6, line 10), and 6 copies (325-5, line 6) of the 3D_C12-7-Ri298 construct using Southern blot analysis of genomic DNA digested with the EcoRI restriction enzyme. Transgene copy number was confirmed using NcoI digested DNA (data not shown). These results indicate that the integration of a single 3D_C12-7-Ri298 construct into the genome of a strong converter tobacco is sufficient for suppressing nornicotine production to very low levels.

GENERAL CONCLUSIONS

The analyses outlined in Examples 1-6 above resulted in the discovery of a closely related P450 gene family, designated the 3D_C12 family, whose collective steady-state transcript levels were significantly elevated in converter tobacco plants that were actively metabolizing nicotine to nornicotine in comparison to their nonconverter counterparts. Transgenic plant analysis demonstrated that the suppression of gene expression of this P450 family in converter tobacco lines inhibited the metabolism of nicotine to nornicotine to levels similar to that observed in nonconverter plants. Furthermore, sense expression of several individuals of this closely related gene family identified one member, designated 3D_C12-7, as playing a direct role in the metabolic conversion of nicotine to nornicotine. Overexpression of 3D_C12-7 using a strong constitutive promoter caused a dramatic increase in nornicotine production and accumulation in non-cured green leaves of transgenic tobacco plants, a tissue where nicotine is normally the predominant alkaloid in converter and nonconverter plants alike. Given that the cytochrome P450 family member designated 3D_C12-10 differs from 3D_C12-7 at only two amino acid residues immediately following the start methionine and within the N-terminal signal sequence, it is predicted that these encoded products function identically.

The contrast in alkaloid phenotypes between the 35S:3D_C12 (1) plant and vector-only control plants was most dramatic in leaves that had been ethephon treated and cured (0.6% conversion versus >97% conversion; Table 6). However, it is noteworthy that the nornicotine content of the co-suppressed 35S:3D_C12 (1) plant was reduced even in green, nontreated leaves where the high nornicotine phenotype is typically not manifest in converter or nonconverter tobacco lines. The green, nontreated leaves of line 35S:3D_C12 (1) showed only 0.7% nicotine to nornicotine conversion, whereas every other plant in this experiment showed conversion percentages ranging from 1.3 to 3.7 (Table 5). This result suggests that the inhibition of gene expression of the 3D_C12 family may prove to be effective in the further lowering of nornicotine levels even in tobacco lines where genetic conversion isn't typically a major problem (such as flue-cured tobaccos) or in the nonconverter individuals in lines that are prone to genetic conversion (such as Burley tobaccos).

Southern blotting assays using members of the 3D_C12 gene family as hybridization probes gives very complex banding patterns, suggesting that more members of this gene family may exist even beyond those that have been identified and characterized herein (data not shown). The hypothesis that the 3D_C12 gene family is comprised of additional members is further supported by the recent publication of 75 full-length tobacco P450 cDNAs of unknown function (U.S. Patent Application Publication 20040162420). Within this list of P450s are additional cDNAs that would, based on the work described herein, be placed within the 3D_C12 family in view of their display of over 90% amino acid sequence identity to the protein sequences shown in FIG. 4.

With respect to the specific molecular function of the 3D_C12-7 gene or the nearly identical family member 3D_C12-10, it is possible that it encodes the actual nicotine demethylase enzyme which catalyzes the oxidative N-demethylation of nicotine to nornicotine (FIG. 1). Alternatively, the 3D_C12-7 encoded enzyme or nearly identical 3D_C12-10 encoded enzyme may produce a product that leads to the up-regulation of the nicotine demethylase activity of the leaf, as opposed to directly catalyzing the N-demethylation reaction.

In addition, an allele-specific RT-PCR was employed to compare 3D_C12-7 expression between converter and nonconverter plants (Example 7). An approximately 80-fold increase in 3D_C12-7 expression in converter versus nonconverter plants was identified using the SYBR® Green-chemistry RT-PCR assay. A 7.5-fold up-regulation was identified by the TaqMan® chemistry-based RT-PCR experiment. While the DH 91-1307-46 tobacco variety used in the TaqMan® chemistry-based RT-PCR experiment exhibits low to moderate levels of nicotine conversion, the DH98-325-5 nonconverter plants used in the SYBR® Green-based RT-PCR assay consistently convert a very low percentage of their nicotine to nornicotine. Expression of the 3D_C12-7 gene was induced at least 7-fold by ethylene in senescing leaves of converter tobacco plants.

An additional RNAi construct, 3D_C12-7-Ri298, was prepared based on a region of the 3D_C12-7 polynucleotide that corresponds to nucleotide positions 297 through 594 of SEQ ID NO:5. Expression of this RNAi construct allows for the suppression of nornicotine production in a strong converter tobacco line below the levels normally found in nonconverter plants. The expression cassette of the 3D_C12-7-Ri298 construct encoded an intron-spliced hairpin RNA in which the stem region was engineered from this 298-bp fragment of the 3D_C12-7 cDNA inserted as an inverted repeat. The loop of the hairpin was created by placing a 151-bp intron of the FAD gene between the two sides of the palindromic sequences. An arm length of 298-bp was used for the inverted repeats.

3D_C12-7-Ri298-transformed plants accumulated less nornicotine than those harboring the 3D_C12-Ri99 construct (Tables 7 and 8). No correlation was found between the number of copies of the 3D_C12-7-Ri298 construct and nornicotine production (Tables 7 and 8). The 3D_C12-7-Ri298 expression cassette enabled the production of tobacco with a conversion rate as low as 0.8%, which is below the 3-5% rate detected in burley lines used by seed producers. Such dramatic reduction in nornicotine production by targeting this particular region of the 3D_C12-7 polynucleotide is an unexpected result. Also, suppression of nornicotine production showed a high degree of heritability in the $T_1$ progeny of the primary transformants (Table 9). Suppression of nornicotine production in these transgenic plants yielded no obvious differences in growth and development when compared to wild-type plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for reducing the level of nornicotine or N'-nitrosonornicotine in a plant of the genus *Nicotiana* or a plant part thereof, said method comprising growing a plant of the genus *Nicotiana*, wherein said plant, or a plant part thereof, comprises an introduced expression cassette that comprises an inhibitory sequence that is operably linked to a promoter that is functional in a plant cell, wherein said inhibitory sequence comprises a first nucleotide sequence, wherein said first nucleotide sequence is a fragment of a polynucleotide having at least 90% sequence identity to the sequence set forth in SEQ ID NO:3, wherein said fragment is from a region of said polynucleotide selected from the group consisting of:
   a) a region that corresponds to nucleotide position 265 to nucleotide position 625 of SEQ ID NO:3, or a complement thereof; and
   b) a region that corresponds to nucleotide position 1420 to nucleotide position 1580 of SEQ ID NO:3, or a complement thereof;
the size of said fragment being from about 100 nucleotides to the full length of said region.

2. The method of claim 1, wherein said inhibitory sequence is capable of being transcribed as an inhibitory polynucleotide selected from the group consisting of a single-stranded RNA polynucleotide, a double-stranded RNA polynucleotide, and a combination thereof.

3. The method of claim 1, wherein said promoter is selected from the group consisting of a constitutive promoter, an inducible promoter, and a tissue-preferred promoter.

4. The method of claim 3, wherein said tissue-preferred promoter is a leaf-preferred promoter.

5. The method of claim 1, wherein said expression cassette is incorporated into a vector.

6. The method of claim 1, wherein said plant is selected from the group consisting of *Nicotiana acuminata multiflora*, *Nicotiana alata grandiflora*, *Nicotiana bigelovii quadrivalvis*, *Nicotiana bigelovii wallacei*, *Nicotiana obtusifolia obtusifolia*, *Nicotiana obtusifolia plameri*, *Nicotiana quadrivalvis bigelovii*, *Nicotiana quadrivalvis quadrivalvis*, *Nicotiana quadrivalvis wallacei*, and *Nicotiana trigonophylla palmeri*.

7. A method for reducing the level of nornicotine or N'-nitrosonornicotine in a tobacco product, said method comprising preparing said tobacco product from a tobacco plant, or a plant part thereof, that has been genetically modified to inhibit the expression of a cytochrome P450 that is involved in the metabolic conversion of nicotine to nornicotine in said tobacco plant, or said plant part thereof, wherein expression of said cytochrome P450 in said tobacco plant, or said plant part thereof, is inhibited by introduction of an expression cassette into said tobacco plant, or a plant part thereof, wherein said expression cassette comprises an inhibitory sequence that is operably linked to a promoter that is functional in a plant cell, wherein said inhibitory sequence comprises a first nucleotide sequence, wherein said first nucleotide sequence is a fragment of a polynucleotide having at least 90% sequence identity to the sequence set forth in SEQ ID NO:3, wherein said fragment is from a region of said polynucleotide selected from the group consisting of:
   a) a region that corresponds to nucleotide position 265 to nucleotide position 625 of SEQ ID NO:3, or a complement thereof; and
   b) a region that corresponds to nucleotide position 1420 to nucleotide position 1580 of SEQ ID NO:3, or a complement thereof;
the size of said fragment being from about 100 nucleotides to the full length of said region.

8. The method of claim 7, wherein said inhibitory sequence is capable of being transcribed as an inhibitory polynucleotide selected from the group consisting of a single-stranded RNA polynucleotide, a double-stranded RNA polynucleotide, and a combination thereof.

9. The method of claim 7, wherein said promoter is selected from the group consisting of a constitutive promoter, an inducible promoter, or a tissue-preferred promoter.

10. The method of claim 9, wherein said tissue-preferred promoter is a leaf-preferred promoter.

11. The method of claim 7, wherein said expression cassette is incorporated into a vector.

12. The method of claim 7, wherein said tobacco product is selected from the group consisting of chewing tobacco, snuff, cigarettes, pipe tobacco, and cigars.

13. The method of claim 7, wherein said tobacco plant is a Burley tobacco variety.

14. The method of claim 7, wherein said tobacco product has a reduced carcinogenic potential.

15. The method of claim 1, wherein said inhibitory sequence comprises a second nucleotide sequence that is fully or partially complementary to said first nucleotide sequence.

16. The method of claim 15, wherein said polynucleotide comprises the sequence set forth in SEQ ID NO:3, and wherein said fragment consists of nucleotides 265 to 625 of SEQ ID NO:3.

17. The method of claim 15, wherein said fragment of said polynucleotide consists of nucleotides from a region of said polynucleotide that corresponds to nucleotide position 297 to nucleotide position 594 of SEQ ID NO:3.

18. The method of claim 17, wherein said polynucleotide comprises the sequence set forth in SEQ ID NO:3, and wherein said fragment consists of nucleotides 297 to 594 of SEQ ID NO:3.

19. The method of claim 18, wherein said second nucleotide sequence comprises the complement of nucleotides 297 to 594 of SEQ ID NO:3.

20. The method of claim 15, wherein said first and said second nucleotide sequences are linked by an intron sequence.

21. The method of claim 20, wherein said intron sequence is a spliceable intron sequence.

22. The method of claim 20, wherein said polynucleotide comprises the sequence set forth in SEQ ID NO:3, and wherein said fragment consists of nucleotides 265 to 625 of SEQ ID NO:3.

23. The method of claim 20, wherein said fragment of said polynucleotide consists of nucleotides from a region of said polynucleotide that corresponds to nucleotide position 297 to nucleotide position 594 of SEQ ID NO:3.

24. The method of claim 23, wherein said polynucleotide comprises the sequence set forth in SEQ ID NO:3, and wherein said fragment consists of nucleotides 297 to 594 of SEQ ID NO:3.

25. The method of claim 24, wherein said second nucleotide sequence comprises the complement of nucleotides 297 to 594 of SEQ ID NO:3.

* * * * *

SEQUENCE LISTING

```
<160> NUMBER OF SEQ ID NOS: 37

<210> SEQ ID NO 1
<211> LENGTH: 1733
<212> TYPE: DNA
<213> ORGANISM: Nicotiana sp.
<220> FEATURE:
<221> NAME/KEY: CDS
<222> LOCATION: (1)...(1551)

<400> SEQUENCE: 1 atg gtt ttt ccc ata gaa gcc ttt gta gga cta gta acc ttc aca ttt      48
Met Val Phe Pro Ile Glu Ala Phe Val Gly Leu Val Thr Phe Thr Phe
 1               5                  10                  15 ctc tta tac ttc cta tgg aca aaa aaa tct caa aaa ctt cca aaa ccc      96
Leu Leu Tyr Phe Leu Trp Thr Lys Lys Ser Gln Lys Leu Pro Lys Pro
             20                  25                  30 tta cca ccg aaa atc ccc gga gga tgg ccg gta atc ggc cat ctt ttt     144
Leu Pro Pro Lys Ile Pro Gly Gly Trp Pro Val Ile Gly His Leu Phe
         35                  40                  45 cac ttc aat aac gac ggc gac gac cgt cca tta gct cga aaa ctc gga     192
His Phe Asn Asn Asp Gly Asp Asp Arg Pro Leu Ala Arg Lys Leu Gly
     50                  55                  60 gac tta gct gat aaa tac ggc ccc gtt ttc act ttt cgg cta ggt ctt     240
Asp Leu Ala Asp Lys Tyr Gly Pro Val Phe Thr Phe Arg Leu Gly Leu
 65                  70                  75                  80 ccc ctt gtg cta gtt gta agc agt tac gaa gct ata aaa gat tgc ttc     288
Pro Leu Val Leu Val Val Ser Ser Tyr Glu Ala Ile Lys Asp Cys Phe
                 85                  90                  95 tct aca aat gac gcc att ttc tcc aat cgt cca gct ttt ctt tac ggc     336
Ser Thr Asn Asp Ala Ile Phe Ser Asn Arg Pro Ala Phe Leu Tyr Gly
            100                 105                 110
```

```
gaa tac ctt ggc tac aat aat aca atg ctt ttt cta gca aat tac gga      384
Glu Tyr Leu Gly Tyr Asn Asn Thr Met Leu Phe Leu Ala Asn Tyr Gly
        115                 120                 125 cct tac tgg cga aaa aat cgt aaa tta gtc att cag gaa gtt ctc tct      432
Pro Tyr Trp Arg Lys Asn Arg Lys Leu Val Ile Gln Glu Val Leu Ser
130                 135                 140 gct agt cgt ctc gaa aaa ttc aaa caa gtg aga ttc acc aga att caa      480
Ala Ser Arg Leu Glu Lys Phe Lys Gln Val Arg Phe Thr Arg Ile Gln
145                 150                 155                 160 acg agc att aag aat tta tac act cga att aat gga aat tcg agt acg      528
Thr Ser Ile Lys Asn Leu Tyr Thr Arg Ile Asn Gly Asn Ser Ser Thr
                165                 170                 175 ata aat cta act gat tgg tta gaa gaa ttg aat ttt ggt ctg atc gtg      576
Ile Asn Leu Thr Asp Trp Leu Glu Glu Leu Asn Phe Gly Leu Ile Val
            180                 185                 190 aaa atg atc gct ggg aaa aat tat gaa tcc ggt aaa gga gat gaa caa      624
Lys Met Ile Ala Gly Lys Asn Tyr Glu Ser Gly Lys Gly Asp Glu Gln
        195                 200                 205 gtg gaa aga ttt aag aat gcg ttt aag gat ttt atg gtt tta tca atg      672
Val Glu Arg Phe Lys Asn Ala Phe Lys Asp Phe Met Val Leu Ser Met
210                 215                 220 gaa ttt gta tta tgg gat gca ttt cca att cca tta ttt aaa tgg gtg      720
Glu Phe Val Leu Trp Asp Ala Phe Pro Ile Pro Leu Phe Lys Trp Val
225                 230                 235                 240 gat ttt caa ggt cat att aag gca atg aaa agg aca ttt aag gat ata      768
Asp Phe Gln Gly His Ile Lys Ala Met Lys Arg Thr Phe Lys Asp Ile
                245                 250                 255 gat tct gtt ttt cag aac tgg tta gag gaa cat att aat aaa aga gaa      816
Asp Ser Val Phe Gln Asn Trp Leu Glu Glu His Ile Asn Lys Arg Glu
            260                 265                 270 aaa atg gag gtt ggt gca gaa ggg aat gaa caa gat ttc att gat gtg      864
Lys Met Glu Val Gly Ala Glu Gly Asn Glu Gln Asp Phe Ile Asp Val
        275                 280                 285 gtg ctt tca aaa ttg agt aaa gaa tat ctt gat gaa ggt tac tct cgt      912
Val Leu Ser Lys Leu Ser Lys Glu Tyr Leu Asp Glu Gly Tyr Ser Arg
290                 295                 300 gat act gtc att aaa gca aca gtt ttt agt ttg gtc ttg gat gca gca      960
Asp Thr Val Ile Lys Ala Thr Val Phe Ser Leu Val Leu Asp Ala Ala
305                 310                 315                 320 gac aca gtt gct ctt cac ata aat tgg gga atg aca tta ttg ata aac     1008
Asp Thr Val Ala Leu His Ile Asn Trp Gly Met Thr Leu Leu Ile Asn
                325                 330                 335 aat caa aat gcc ttg atg aaa gca caa gaa gag ata gac aca aaa gtt     1056
Asn Gln Asn Ala Leu Met Lys Ala Gln Glu Glu Ile Asp Thr Lys Val
            340                 345                 350 ggt aag gat aga tgg gta gaa gag agt gat att aag gat tta gta tac     1104
Gly Lys Asp Arg Trp Val Glu Glu Ser Asp Ile Lys Asp Leu Val Tyr
        355                 360                 365 ctc caa gct att gtt aaa aag gtg tta cga tta tat cca cca gga cct     1152
Leu Gln Ala Ile Val Lys Lys Val Leu Arg Leu Tyr Pro Pro Gly Pro
370                 375                 380 ttg tta gta cca cat gaa aat gta aag gat tgt gtt gtt agt gga tat     1200
Leu Leu Val Pro His Glu Asn Val Lys Asp Cys Val Val Ser Gly Tyr
385                 390                 395                 400 cac att cct aaa gag act aga tta ttc gca aac gtc atg aaa ctg cag     1248
His Ile Pro Lys Glu Thr Arg Leu Phe Ala Asn Val Met Lys Leu Gln
                405                 410                 415 cgc gat cct aaa ctc ttg tca aat cct gat aag ttc gat cca gag aga     1296
Arg Asp Pro Lys Leu Leu Ser Asn Pro Asp Lys Phe Asp Pro Glu Arg
            420                 425                 430
```

```
ttc atc gct ggt gat att gac ttc cgt ggt cac cac tat gag ttt atc      1344
Phe Ile Ala Gly Asp Ile Asp Phe Arg Gly His His Tyr Glu Phe Ile
            435                 440                 445 cca ttt ggt tct gga aga cga tct tgt ccg ggg atg act tat gca ttg      1392
Pro Phe Gly Ser Gly Arg Arg Ser Cys Pro Gly Met Thr Tyr Ala Leu
450                 455                 460 caa gtg gaa cac cta aca atg gca cat tta atc cag ggt ttc aat tac      1440
Gln Val Glu His Leu Thr Met Ala His Leu Ile Gln Gly Phe Asn Tyr
465                 470                 475                 480 aaa act cca aat gac gag gcc ttg gat atg aag gaa ggt gca ggc ata      1488
Lys Thr Pro Asn Asp Glu Ala Leu Asp Met Lys Glu Gly Ala Gly Ile
            485                 490                 495 acc ata cgt aag gta aat cca gtg gaa ttg ata ata acg cct cgc ttg      1536
Thr Ile Arg Lys Val Asn Pro Val Glu Leu Ile Ile Thr Pro Arg Leu
        500                 505                 510 gca cct gag ctt tac taaaacctaa gatctttcat cttggttgat cattgtttaa      1591
Ala Pro Glu Leu Tyr
        515 tactcctaga tgggtattca tttaccttt ttcaattaat tgcatgtacg agctttttta    1651 atttggtata tttgtaacaa taagtaaaga atgattgtgc taatatataa agatttgcag    1711 aagataattg actgattgtc cc                                             1733

<210> SEQ ID NO 2
<211> LENGTH: 517
<212> TYPE: PRT
<213> ORGANISM: Nicotiana sp.

<400> SEQUENCE: 2

Met Val Phe Pro Ile Glu Ala Phe Val Gly Leu Val Thr Phe Thr Phe
1               5                   10                  15

Leu Leu Tyr Phe Leu Trp Thr Lys Lys Ser Gln Lys Leu Pro Lys Pro
            20                  25                  30

Leu Pro Pro Lys Ile Pro Gly Gly Trp Pro Val Ile Gly His Leu Phe
        35                  40                  45

His Phe Asn Asn Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Thr Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys Gln Val Arg Phe Thr Arg Ile Gln
145                 150                 155                 160

Thr Ser Ile Lys Asn Leu Tyr Thr Arg Ile Asn Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Asn Ala Phe Lys Asp Phe Met Val Leu Ser Met
```

-continued

```
                210                 215                 220
Glu Phe Val Leu Trp Asp Ala Phe Pro Ile Pro Leu Phe Lys Trp Val
225                 230                 235                 240

Asp Phe Gln Gly His Ile Lys Ala Met Lys Arg Thr Phe Lys Asp Ile
            245                 250                 255

Asp Ser Val Phe Gln Asn Trp Leu Glu Glu His Ile Asn Lys Arg Glu
            260                 265                 270

Lys Met Glu Val Gly Ala Glu Gly Asn Glu Gln Asp Phe Ile Asp Val
        275                 280                 285

Val Leu Ser Lys Leu Ser Lys Glu Tyr Leu Asp Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Thr Leu Leu Ile Asn
            325                 330                 335

Asn Gln Asn Ala Leu Met Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Lys Val Leu Arg Leu Tyr Pro Pro Gly Pro
370                 375                 380

Leu Leu Val Pro His Glu Asn Val Lys Asp Cys Val Val Ser Gly Tyr
385                 390                 395                 400

His Ile Pro Lys Glu Thr Arg Leu Phe Ala Asn Val Met Lys Leu Gln
            405                 410                 415

Arg Asp Pro Lys Leu Leu Ser Asn Pro Asp Lys Phe Asp Pro Glu Arg
            420                 425                 430

Phe Ile Ala Gly Asp Ile Asp Phe Arg Gly His His Tyr Glu Phe Ile
        435                 440                 445

Pro Phe Gly Ser Gly Arg Arg Ser Cys Pro Gly Met Thr Tyr Ala Leu
            450                 455                 460

Gln Val Glu His Leu Thr Met Ala His Leu Ile Gln Gly Phe Asn Tyr
465                 470                 475                 480

Lys Thr Pro Asn Asp Glu Ala Leu Asp Met Lys Glu Gly Ala Gly Ile
            485                 490                 495

Thr Ile Arg Lys Val Asn Pro Val Glu Leu Ile Ile Thr Pro Arg Leu
        500                 505                 510

Ala Pro Glu Leu Tyr
        515

<210> SEQ ID NO 3
<211> LENGTH: 1733
<212> TYPE: DNA
<213> ORGANISM: Nicotiana sp.
<220> FEATURE:
<221> NAME/KEY: CDS
<222> LOCATION: (1)...(1551)

<400> SEQUENCE: 3 atg ctt tct ccc ata gaa gcc att gta gga cta gta acc ttc aca ttt    48
Met Leu Ser Pro Ile Glu Ala Ile Val Gly Leu Val Thr Phe Thr Phe
1               5                   10                  15 ctc ttc ttc ttc cta tgg aca aaa aaa tct caa aaa cct tca aaa ccc    96
Leu Phe Phe Phe Leu Trp Thr Lys Lys Ser Gln Lys Pro Ser Lys Pro
            20                  25                  30 tta cca ccg aaa atc ccc gga gga tgg ccg gta atc ggc cat ctt ttc   144
```

```
                                                                    -continued Leu Pro Pro Lys Ile Pro Gly Gly Trp Pro Val Ile Gly His Leu Phe
        35              40                  45 cac ttc aat gac gac ggc gac gac cgt cca tta gct cga aaa ctc gga        192
His Phe Asn Asp Asp Gly Asp Asp Arg Pro Leu Ala Arg Lys Leu Gly
 50              55                  60 gac tta gct gac aaa tac ggc ccc gtt ttc act ttt cgg cta ggc ctt        240
Asp Leu Ala Asp Lys Tyr Gly Pro Val Phe Thr Phe Arg Leu Gly Leu
 65              70                  75                  80 ccc ctt gtc tta gtt gta agc agt tac gaa gct gta aaa gac tgt ttc        288
Pro Leu Val Leu Val Val Ser Ser Tyr Glu Ala Val Lys Asp Cys Phe
                 85                  90                  95 tct aca aat gac gcc att ttt tcc aat cgt cca gct ttt ctt tac ggc        336
Ser Thr Asn Asp Ala Ile Phe Ser Asn Arg Pro Ala Phe Leu Tyr Gly
            100                 105                 110 gat tac ctt ggc tac aat aat gcc atg cta ttt ttg gcc aat tac gga        384
Asp Tyr Leu Gly Tyr Asn Asn Ala Met Leu Phe Leu Ala Asn Tyr Gly
            115                 120                 125 cct tac tgg cga aaa aat cga aaa tta gtt att cag gaa gtt ctc tcc        432
Pro Tyr Trp Arg Lys Asn Arg Lys Leu Val Ile Gln Glu Val Leu Ser
        130                 135                 140 gct agt cgt ctc gaa aaa ttc aaa cac gtg aga ttt gca aga att caa        480
Ala Ser Arg Leu Glu Lys Phe Lys His Val Arg Phe Ala Arg Ile Gln
145                 150                 155                 160 gcg agc att aag aat tta tat act cga att gat gga aat tcg agt acg        528
Ala Ser Ile Lys Asn Leu Tyr Thr Arg Ile Asp Gly Asn Ser Ser Thr
                165                 170                 175 ata aat tta act gat tgg tta gaa gaa ttg aat ttt ggt ctg atc gtg        576
Ile Asn Leu Thr Asp Trp Leu Glu Glu Leu Asn Phe Gly Leu Ile Val
            180                 185                 190 aag atg atc gct gga aaa aat tat gaa tcc ggt aaa gga gat gaa caa        624
Lys Met Ile Ala Gly Lys Asn Tyr Glu Ser Gly Lys Gly Asp Glu Gln
            195                 200                 205 gtg gag aga ttt aag aaa gcg ttt aag gat ttt atg att tta tca atg        672
Val Glu Arg Phe Lys Lys Ala Phe Lys Asp Phe Met Ile Leu Ser Met
        210                 215                 220 gag ttt gtg tta tgg gat gca ttt cca att cca tta ttt aaa tgg gtg        720
Glu Phe Val Leu Trp Asp Ala Phe Pro Ile Pro Leu Phe Lys Trp Val
225                 230                 235                 240 gat ttt caa ggg cat gtt aag gct atg aaa agg act ttt aaa gat ata        768
Asp Phe Gln Gly His Val Lys Ala Met Lys Arg Thr Phe Lys Asp Ile
                245                 250                 255 gat tct gtt ttt cag aat tgg tta gag gaa cat att aat aaa aga gaa        816
Asp Ser Val Phe Gln Asn Trp Leu Glu Glu His Ile Asn Lys Arg Glu
            260                 265                 270 aaa atg gag gtt aat gca gaa ggg aat gaa caa gat ttc att gat gtg        864
Lys Met Glu Val Asn Ala Glu Gly Asn Glu Gln Asp Phe Ile Asp Val
        275                 280                 285 gtg ctt tca aaa atg agt aat gaa tat ctt ggt gaa ggt tac tct cgt        912
Val Leu Ser Lys Met Ser Asn Glu Tyr Leu Gly Glu Gly Tyr Ser Arg
        290                 295                 300 gat act gtc att aaa gca acg gtg ttt agt ttg gtc ttg gat gca gca        960
Asp Thr Val Ile Lys Ala Thr Val Phe Ser Leu Val Leu Asp Ala Ala
305                 310                 315                 320 gac aca gtt gct ctt cac ata aat tgg gga atg gca tta ttg ata aac       1008
Asp Thr Val Ala Leu His Ile Asn Trp Gly Met Ala Leu Leu Ile Asn
                325                 330                 335 aat caa aag gcc ttg acg aaa gca caa gaa gag ata gac aca aaa gtt       1056
Asn Gln Lys Ala Leu Thr Lys Ala Gln Glu Glu Ile Asp Thr Lys Val
            340                 345                 350
```

-continued

```
ggt aag gac aga tgg gta gaa gag agt gat att aag gat ttg gta tac       1104
Gly Lys Asp Arg Trp Val Glu Glu Ser Asp Ile Lys Asp Leu Val Tyr
        355                 360                 365 ctc caa gct att gtt aaa gaa gtg tta cga tta tat cca cca gga cct       1152
Leu Gln Ala Ile Val Lys Glu Val Leu Arg Leu Tyr Pro Pro Gly Pro
    370                 375                 380 ttg tta gta cca cac gaa aat gta gaa gat tgt gtt gtt agt gga tat       1200
Leu Leu Val Pro His Glu Asn Val Glu Asp Cys Val Val Ser Gly Tyr
385                 390                 395                 400 cac att cct aaa ggg aca aga tta ttc gca aac gtc atg aaa ctg caa       1248
His Ile Pro Lys Gly Thr Arg Leu Phe Ala Asn Val Met Lys Leu Gln
                405                 410                 415 cgt gat cct aaa ctc tgg tct gat cct gat act ttc gat cca gag aga       1296
Arg Asp Pro Lys Leu Trp Ser Asp Pro Asp Thr Phe Asp Pro Glu Arg
            420                 425                 430 ttc att gct act gat att gac ttt cgt ggt cag tac tat aag tat atc       1344
Phe Ile Ala Thr Asp Ile Asp Phe Arg Gly Gln Tyr Tyr Lys Tyr Ile
        435                 440                 445 ccg ttt ggt tct gga aga cga tct tgt cca ggg atg act tat gca ttg       1392
Pro Phe Gly Ser Gly Arg Arg Ser Cys Pro Gly Met Thr Tyr Ala Leu
    450                 455                 460 caa gtg gaa cac tta aca atg gca cat ttg atc caa ggt ttc aat tac       1440
Gln Val Glu His Leu Thr Met Ala His Leu Ile Gln Gly Phe Asn Tyr
465                 470                 475                 480 aga act cca aat gac gag ccc ttg gat atg aag gaa ggt gca ggc ata       1488
Arg Thr Pro Asn Asp Glu Pro Leu Asp Met Lys Glu Gly Ala Gly Ile
                485                 490                 495 act ata cgt aag gta aat cct gtg gaa ctg ata ata gcg cct cgc ctg       1536
Thr Ile Arg Lys Val Asn Pro Val Glu Leu Ile Ile Ala Pro Arg Leu
            500                 505                 510 gca cct gag ctt tat taaaacctaa gatctttcat cttggttgat cattgtataa       1591
Ala Pro Glu Leu Tyr
        515 tactcctaaa tggatattca tttacctttt atcaattaat tgtcagtacg agttttcta    1651 atttggtaca tttgtaataa taagtaaaga ataattgtgc taatatataa aggtttgtag   1711 aagataattg actgattgtc cc                                             1733

<210> SEQ ID NO 4
<211> LENGTH: 517
<212> TYPE: PRT
<213> ORGANISM: Nicotiana sp.

<400> SEQUENCE: 4

Met Leu Ser Pro Ile Glu Ala Ile Val Gly Leu Val Thr Phe Thr Phe
 1               5                  10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110
```

-continued

```
Asp Tyr Leu Gly Tyr Asn Asn Ala Met Leu Phe Leu Ala Asn Tyr Gly
        115                 120                 125
Pro Tyr Trp Arg Lys Asn Arg Lys Leu Val Ile Gln Glu Val Leu Ser
    130                 135                 140
Ala Ser Arg Leu Glu Lys Phe Lys His Val Arg Phe Ala Arg Ile Gln
145                 150                 155                 160
Ala Ser Ile Lys Asn Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
            180                 185                 190
Lys Met Ile Ala Gly Lys Asn Tyr Glu Ser Gly Lys Gly Asp Glu Gln
        195                 200                 205
Val Glu Arg Phe Lys Lys Ala Phe Lys Asp Phe Met Ile Leu Ser Met
    210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Ile Asn Lys Arg Glu
            260                 265                 270
Lys Met Glu Val Asn Ala Glu Gly Asn Glu Gln Asp Phe Ile Asp Val
        275                 280                 285
Val Leu Ser Lys Met Ser Asn Glu Tyr Leu Gly Glu Gly Tyr Ser Arg
    290                 295                 300
Asp Thr Val Ile Lys Ala Thr Val Phe Ser Leu Val Leu Asp Ala Ala
305                 310                 315                 320
Asp Thr Val Ala Leu His Ile Asn Trp Gly Met Ala Leu Leu Ile Asn
                325                 330                 335
Asn Gln Lys Ala Leu Thr Lys Ala Gln Glu Glu Ile Asp Thr Lys Val
            340                 345                 350
Gly Lys Asp Arg Trp Val Glu Glu Ser Asp Ile Lys Asp Leu Val Tyr
        355                 360                 365
Leu Gln Ala Ile Val Lys Glu Val Leu Arg Leu Tyr Pro Pro Gly Pro
    370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
Arg Asp Pro Lys Leu Trp Ser Asp Pro Asp Thr Phe Asp Pro Glu Arg
            420                 425                 430
Phe Ile Ala Thr Asp Ile Asp Phe Arg Gly Gln Tyr Tyr Lys Tyr Ile
        435                 440                 445
Pro Phe Gly Ser Gly Arg Arg Ser Cys Pro Gly Met Thr Tyr Ala Leu
    450                 455                 460
Gln Val Glu His Leu Thr Met Ala His Leu Ile Gln Gly Phe Asn Tyr
465                 470                 475                 480
Arg Thr Pro Asn Asp Glu Pro Leu Asp Met Lys Glu Gly Ala Gly Ile
                485                 490                 495
Thr Ile Arg Lys Val Asn Pro Val Glu Leu Ile Ile Ala Pro Arg Leu
            500                 505                 510
Ala Pro Glu Leu Tyr
        515
```

<210> SEQ ID NO 5
<211> LENGTH: 1733
<212> TYPE: DNA
<213> ORGANISM: Nicotiana sp.
<220> FEATURE:
<221> NAME/KEY: CDS
<222> LOCATION: (1)...(1551)

<400> SEQUENCE: 5

```
atg gtt ttt ccc ata gaa gcc att gta gga cta gta acc ttc aca ttt      48
Met Val Phe Pro Ile Glu Ala Ile Val Gly Leu Val Thr Phe Thr Phe
 1               5                  10                  15 ctc ttc ttc ttc cta tgg aca aaa aaa tct caa aaa cct tca aaa ccc      96
Leu Phe Phe Phe Leu Trp Thr Lys Lys Ser Gln Lys Pro Ser Lys Pro
             20                  25                  30 tta cca ccg aaa atc ccc gga gga tgg ccg gta atc ggc cat ctt ttc     144
Leu Pro Pro Lys Ile Pro Gly Gly Trp Pro Val Ile Gly His Leu Phe
         35                  40                  45 cac ttc aat gac gac ggc gac gac cgt cca tta gct cga aaa ctc gga     192
His Phe Asn Asp Asp Gly Asp Asp Arg Pro Leu Ala Arg Lys Leu Gly
     50                  55                  60 gac tta gct gac aaa tac ggc ccc gtt ttc act ttt cgg cta ggc ctt     240
Asp Leu Ala Asp Lys Tyr Gly Pro Val Phe Thr Phe Arg Leu Gly Leu
 65                  70                  75                  80 ccc ctt gtc tta gtt gta agc agt tac gaa gct gta aaa gac tgt ttc     288
Pro Leu Val Leu Val Val Ser Ser Tyr Glu Ala Val Lys Asp Cys Phe
                 85                  90                  95 tct aca aat gac gcc att ttt tcc aat cgt cca gct ttt ctt tac ggc     336
Ser Thr Asn Asp Ala Ile Phe Ser Asn Arg Pro Ala Phe Leu Tyr Gly
            100                 105                 110 gat tac ctt ggc tac aat aat gcc atg cta ttt ttg gcc aat tac gga     384
Asp Tyr Leu Gly Tyr Asn Asn Ala Met Leu Phe Leu Ala Asn Tyr Gly
        115                 120                 125 cct tac tgg cga aaa aat cga aaa tta gtt att cag gaa gtt ctc tcc     432
Pro Tyr Trp Arg Lys Asn Arg Lys Leu Val Ile Gln Glu Val Leu Ser
    130                 135                 140 gct agt cgt ctc gaa aaa ttc aaa cac gtg aga ttt gca aga att caa     480
Ala Ser Arg Leu Glu Lys Phe Lys His Val Arg Phe Ala Arg Ile Gln
145                 150                 155                 160 gcg agc att aag aat tta tat act cga att gat gga aat tcg agt acg     528
Ala Ser Ile Lys Asn Leu Tyr Thr Arg Ile Asp Gly Asn Ser Ser Thr
                165                 170                 175 ata aat tta act gat tgg tta gaa gaa ttg aat ttt ggt ctg atc gtg     576
Ile Asn Leu Thr Asp Trp Leu Glu Glu Leu Asn Phe Gly Leu Ile Val
            180                 185                 190 aag atg atc gct gga aaa aat tat gaa tcc ggt aaa gga gat gaa caa     624
Lys Met Ile Ala Gly Lys Asn Tyr Glu Ser Gly Lys Gly Asp Glu Gln
        195                 200                 205 gtg gag aga ttt aag aaa gcg ttt aag gat ttt atg att tta tca atg     672
Val Glu Arg Phe Lys Lys Ala Phe Lys Asp Phe Met Ile Leu Ser Met
    210                 215                 220 gag ttt gtg tta tgg gat gca ttt cca att cca tta ttt aaa tgg gtg     720
Glu Phe Val Leu Trp Asp Ala Phe Pro Ile Pro Leu Phe Lys Trp Val
225                 230                 235                 240 gat ttt caa ggg cat gtt aag gct atg aaa agg act ttt aaa gat ata     768
Asp Phe Gln Gly His Val Lys Ala Met Lys Arg Thr Phe Lys Asp Ile
                245                 250                 255 gat tct gtt ttt cag aat tgg tta gag gaa cat att aat aaa aga gaa     816
Asp Ser Val Phe Gln Asn Trp Leu Glu Glu His Ile Asn Lys Arg Glu
            260                 265                 270 aaa atg gag gtt aat gca gaa ggg aat gaa caa gat ttc att gat gtg     864
```

```
Lys Met Glu Val Asn Ala Glu Gly Asn Glu Gln Asp Phe Ile Asp Val
        275                 280                 285 gtg ctt tca aaa atg agt aat gaa tat ctt ggt gaa ggt tac tct cgt        912
Val Leu Ser Lys Met Ser Asn Glu Tyr Leu Gly Glu Gly Tyr Ser Arg
        290                 295                 300 gat act gtc att aag gca acg gtt ttt agt ttg gtc ttg gat gca gca        960
Asp Thr Val Ile Lys Ala Thr Val Phe Ser Leu Val Leu Asp Ala Ala
305                 310                 315                 320 gac aca gtt gct ctt cac ata aat tgg gga atg gca tta ttg ata aac       1008
Asp Thr Val Ala Leu His Ile Asn Trp Gly Met Ala Leu Leu Ile Asn
                    325                 330                 335 aat caa aag gcc ttg acg aaa gca caa gaa gag ata gac aca aaa gtt       1056
Asn Gln Lys Ala Leu Thr Lys Ala Gln Glu Glu Ile Asp Thr Lys Val
        340                 345                 350 ggt aag gac aga tgg gta gaa gag agt gat att aag gat ttg gta tac       1104
Gly Lys Asp Arg Trp Val Glu Glu Ser Asp Ile Lys Asp Leu Val Tyr
        355                 360                 365 ctc caa gct att gtt aaa gaa gtg tta cga tta tat cca cca gga cct       1152
Leu Gln Ala Ile Val Lys Glu Val Leu Arg Leu Tyr Pro Pro Gly Pro
    370                 375                 380 ttg tta gta cca cac gaa aat gta gaa gat tgt gtt gtt agt gga tat       1200
Leu Leu Val Pro His Glu Asn Val Glu Asp Cys Val Val Ser Gly Tyr
385                 390                 395                 400 cac att cct aaa ggg aca aga tta ttc gca aac gtc atg aaa ctg caa       1248
His Ile Pro Lys Gly Thr Arg Leu Phe Ala Asn Val Met Lys Leu Gln
                405                 410                 415 cgt gat cct aaa ctc tgg tct gat cct gat act ttc gat cca gag aga       1296
Arg Asp Pro Lys Leu Trp Ser Asp Pro Asp Thr Phe Asp Pro Glu Arg
            420                 425                 430 ttc att gct act gat att gac ttt cgt ggt cag tac tat aag tat atc       1344
Phe Ile Ala Thr Asp Ile Asp Phe Arg Gly Gln Tyr Tyr Lys Tyr Ile
        435                 440                 445 ccg ttt ggt tct gga aga cga tct tgt cca ggg atg act tat gca ttg       1392
Pro Phe Gly Ser Gly Arg Arg Ser Cys Pro Gly Met Thr Tyr Ala Leu
    450                 455                 460 caa gtg gaa cac tta aca atg gca cat ttg atc caa ggt ttc aat tac       1440
Gln Val Glu His Leu Thr Met Ala His Leu Ile Gln Gly Phe Asn Tyr
465                 470                 475                 480 aga act cca aat gac gag ccc ttg gac atg aag gaa ggt gca ggc ata       1488
Arg Thr Pro Asn Asp Glu Pro Leu Asp Met Lys Glu Gly Ala Gly Ile
                485                 490                 495 act ata cgt aag gta aat cct gtg gaa ctg ata ata gcg cct cgc ctg       1536
Thr Ile Arg Lys Val Asn Pro Val Glu Leu Ile Ile Ala Pro Arg Leu
            500                 505                 510 gca cct gag ctt tat taaaacctaa gatctttcat cttggttgat cattgtataa       1591
Ala Pro Glu Leu Tyr
        515 tactcctaaa tggatattca tttaccttt atcaattaat tgtcagtacg agttttcta      1651 atttggtaca tttgtaataa taagtaaaga ataattgtgc taatatataa aggtttgtag      1711 aagatgattg actgattgtc cc                                              1733

<210> SEQ ID NO 6
<211> LENGTH: 517
<212> TYPE: PRT
<213> ORGANISM: Nicotiana sp.

<400> SEQUENCE: 6

Met Val Phe Pro Ile Glu Ala Ile Val Gly Leu Val Thr Phe Thr Phe
1               5                   10                  15
```

```
Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Ile Asp Thr Lys Val
            340                 345                 350

Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430
```

```
Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
            485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 7
<211> LENGTH: 1727
<212> TYPE: DNA
<213> ORGANISM: Nicotiana sp.
<220> FEATURE:
<221> NAME/KEY: CDS
<222> LOCATION: (1)...(1554)

<400> SEQUENCE: 7
```

| | | | | | | | | | | | | | | | | |
|---|---|---|---|---|---|---|---|---|---|---|---|---|---|---|---|---|
| atg | gtt | ttt | ccg | gta | gaa | gcc | att | gta | ggg | cta | gtg | acc | ttc | aca | ttt | 48 |
| Met | Val | Phe | Pro | Val | Glu | Ala | Ile | Val | Gly | Leu | Val | Thr | Phe | Thr | Phe | |
| 1 | | | | 5 | | | | | 10 | | | | | 15 | | |
| ctc | ttc | tac | ttc | cta | tgg | aca | aaa | aaa | tct | caa | aaa | cct | tca | aaa | ccc | 96 |
| Leu | Phe | Tyr | Phe | Leu | Trp | Thr | Lys | Lys | Ser | Gln | Lys | Pro | Ser | Lys | Pro | |
| | | | 20 | | | | | 25 | | | | | 30 | | | |
| tta | cca | ccg | aaa | atc | ccg | gga | gga | tgg | ccg | gta | atc | ggc | cat | ctt | ttc | 144 |
| Leu | Pro | Pro | Lys | Ile | Pro | Gly | Gly | Trp | Pro | Val | Ile | Gly | His | Leu | Phe | |
| | | 35 | | | | | 40 | | | | | 45 | | | | |
| tac | ttc | gat | gac | gac | ggc | gac | gac | cgt | cca | tta | gct | cga | aaa | ctc | gga | 192 |
| Tyr | Phe | Asp | Asp | Asp | Gly | Asp | Asp | Arg | Pro | Leu | Ala | Arg | Lys | Leu | Gly | |
| | 50 | | | | | 55 | | | | | 60 | | | | | |
| gac | tta | gct | gac | aaa | tac | gga | ccc | gtt | ttc | act | ttt | cgg | cta | ggc | ctt | 240 |
| Asp | Leu | Ala | Asp | Lys | Tyr | Gly | Pro | Val | Phe | Thr | Phe | Arg | Leu | Gly | Leu | |
| 65 | | | | 70 | | | | | 75 | | | | | 80 | | |
| ccc | ctt | gtg | tta | gtt | gta | agc | agt | tac | gaa | gct | ata | aaa | gat | tgt | ttc | 288 |
| Pro | Leu | Val | Leu | Val | Val | Ser | Ser | Tyr | Glu | Ala | Ile | Lys | Asp | Cys | Phe | |
| | | | | 85 | | | | | 90 | | | | | 95 | | |
| tct | aca | aat | gac | gcc | att | ttc | tcc | aat | cgt | cca | gct | ttt | ctt | tac | ggc | 336 |
| Ser | Thr | Asn | Asp | Ala | Ile | Phe | Ser | Asn | Arg | Pro | Ala | Phe | Leu | Tyr | Gly | |
| | | | 100 | | | | | 105 | | | | | 110 | | | |
| gaa | tac | ctt | ggc | tac | aaa | aat | gcc | atg | cta | ttt | ttg | gca | aat | tac | gga | 384 |
| Glu | Tyr | Leu | Gly | Tyr | Lys | Asn | Ala | Met | Leu | Phe | Leu | Ala | Asn | Tyr | Gly | |
| | | 115 | | | | | 120 | | | | | 125 | | | | |
| tct | tac | tgg | cga | aaa | aat | cgt | aaa | tta | att | att | cag | gaa | gtt | ctc | tct | 432 |
| Ser | Tyr | Trp | Arg | Lys | Asn | Arg | Lys | Leu | Ile | Ile | Gln | Glu | Val | Leu | Ser | |
| | 130 | | | | | 135 | | | | | 140 | | | | | |
| gct | agt | cgt | ctc | gaa | aaa | ttc | aaa | cac | gtg | aga | ttc | gcc | aga | att | caa | 480 |
| Ala | Ser | Arg | Leu | Glu | Lys | Phe | Lys | His | Val | Arg | Phe | Ala | Arg | Ile | Gln | |
| 145 | | | | 150 | | | | | 155 | | | | | 160 | | |
| acg | agc | att | aag | aat | tta | tac | act | cga | att | gat | gga | aat | tcg | agt | acg | 528 |
| Thr | Ser | Ile | Lys | Asn | Leu | Tyr | Thr | Arg | Ile | Asp | Gly | Asn | Ser | Ser | Thr | |
| | | | 165 | | | | | 170 | | | | | 175 | | | |
| ata | aat | tta | act | gat | tgg | tta | gaa | gaa | ttg | aat | ttt | ggt | ctg | atc | gtg | 576 |
| Ile | Asn | Leu | Thr | Asp | Trp | Leu | Glu | Glu | Leu | Asn | Phe | Gly | Leu | Ile | Val | |
| | | | 180 | | | | | 185 | | | | | 190 | | | |
| aaa | atg | atc | gct | ggg | aaa | aat | tat | gaa | tcc | ggt | aaa | gga | gat | gaa | caa | 624 |
| Lys | Met | Ile | Ala | Gly | Lys | Asn | Tyr | Glu | Ser | Gly | Lys | Gly | Asp | Glu | Gln | |

-continued

```
              195                 200                 205
gtg gag aga ttt aag aaa gcg ttt aag gat ttt atg att tta tca atg     672
Val Glu Arg Phe Lys Lys Ala Phe Lys Asp Phe Met Ile Leu Ser Met
    210                 215                 220 gag ttt gtg tta tgg gat gca ttt cca att cca tta ttt aaa tgg gtg     720
Glu Phe Val Leu Trp Asp Ala Phe Pro Ile Pro Leu Phe Lys Trp Val
225                 230                 235                 240 gat ttt caa ggg cat gtt aag gct atg aaa agg act ttt aaa gat ata     768
Asp Phe Gln Gly His Val Lys Ala Met Lys Arg Thr Phe Lys Asp Ile
                245                 250                 255 gat tct gtt ttt cag aat tgg tta gag gaa cat att aag aaa aga gaa     816
Asp Ser Val Phe Gln Asn Trp Leu Glu Glu His Ile Lys Lys Arg Glu
            260                 265                 270 aaa ata atg gag gtt ggt aca gaa ggg aat gaa caa gat ttt ata gat     864
Lys Ile Met Glu Val Gly Thr Glu Gly Asn Glu Gln Asp Phe Ile Asp
        275                 280                 285 gtg gtg ctt tca aaa atg agt aat gaa tat ctt ggc gaa ggt tac tct     912
Val Val Leu Ser Lys Met Ser Asn Glu Tyr Leu Gly Glu Gly Tyr Ser
    290                 295                 300 cgc gat act gtc ata aaa gca aca gta ttt agt ttg gtc ttg gat gca     960
Arg Asp Thr Val Ile Lys Ala Thr Val Phe Ser Leu Val Leu Asp Ala
305                 310                 315                 320 gca gac aca gtt gct ctt cac ata aat tgc gga atg gca tta ttg ata    1008
Ala Asp Thr Val Ala Leu His Ile Asn Cys Gly Met Ala Leu Leu Ile
                325                 330                 335 aac aat caa aat gcc ttg aag aaa gca caa gaa gag ata gac aca aaa    1056
Asn Asn Gln Asn Ala Leu Lys Lys Ala Gln Glu Glu Ile Asp Thr Lys
            340                 345                 350 gtt ggt aag gat aga tgg gta gaa gag agt gat att aag gat ttg gta    1104
Val Gly Lys Asp Arg Trp Val Glu Glu Ser Asp Ile Lys Asp Leu Val
        355                 360                 365 tac ctc caa gct att gtt aaa gaa gtg tta cga tta tat cca ccg gga    1152
Tyr Leu Gln Ala Ile Val Lys Glu Val Leu Arg Leu Tyr Pro Pro Gly
    370                 375                 380 cct ttg tta gta cca cac gaa aat gta gaa gat tgt gtt gtt agt gga    1200
Pro Leu Leu Val Pro His Glu Asn Val Glu Asp Cys Val Val Ser Gly
385                 390                 395                 400 tat cac att cct aaa gga act aga cta ttc gca aat gta atg aaa cta    1248
Tyr His Ile Pro Lys Gly Thr Arg Leu Phe Ala Asn Val Met Lys Leu
                405                 410                 415 caa cgt gat cct aaa ctc tgg tca aat cct gat aag ttc aat cca gag    1296
Gln Arg Asp Pro Lys Leu Trp Ser Asn Pro Asp Lys Phe Asn Pro Glu
            420                 425                 430 aga ttc atc gct cgt gat att gac ttt cat ggt cag cac tat gag tat    1344
Arg Phe Ile Ala Arg Asp Ile Asp Phe His Gly Gln His Tyr Glu Tyr
        435                 440                 445 atc ccg ttt ggt tct gga aga cgc tct tgt ccg ggg atg act tat gca    1392
Ile Pro Phe Gly Ser Gly Arg Arg Ser Cys Pro Gly Met Thr Tyr Ala
    450                 455                 460 ttg caa gtg gaa cac cta aca atg gca cat ttg atc cag ggt ttc aat    1440
Leu Gln Val Glu His Leu Thr Met Ala His Leu Ile Gln Gly Phe Asn
465                 470                 475                 480 tac aga act cca act gat gag ccc ttg gat atg aaa gaa ggt gca ggc    1488
Tyr Arg Thr Pro Thr Asp Glu Pro Leu Asp Met Lys Glu Gly Ala Gly
                485                 490                 495 ata act ata cgt aag gta aat cct gtg aaa gtg ata att acg cct cgc    1536
Ile Thr Ile Arg Lys Val Asn Pro Val Lys Val Ile Ile Thr Pro Arg
            500                 505                 510 ttg gca cct gag ctt tat taaaatctaa gatgtttcat cttggttgat           1584
Leu Ala Pro Glu Leu Tyr
```

Leu Ala Pro Glu Leu Tyr
        515 cattgtttaa tactcctaga tgggtattca tctacctttt ttcaattagt tgtcggtacg    1644 tattttttta atttggtaag tttgtaataa taagtaaaga aggattgtgc taatatataa    1704 tggtgcataa aataattgaa atg    1727

<210> SEQ ID NO 8
<211> LENGTH: 518
<212> TYPE: PRT
<213> ORGANISM: Nicotiana sp.

<400> SEQUENCE: 8

Met Val Phe Pro Val Glu Ala Ile Val Gly Leu Val Thr Phe Thr Phe
1               5                   10                  15

Leu Phe Tyr Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Lys Asn Ala Met Leu Phe Leu Ala Asn Tyr Gly
        115                 120                 125

Ser Tyr Trp Arg Lys Asn Arg Lys Leu Ile Ile Gln Glu Val Leu Ser
    130                 135                 140

Ala Ser Arg Leu Glu Lys Phe Lys His Val Arg Phe Ala Arg Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Lys Lys Arg Glu
            260                 265                 270

Lys Ile Met Glu Val Gly Thr Glu Gly Asn Glu Gln Asp Phe Ile Asp
        275                 280                 285

Val Val Leu Ser Lys Met Ser Asn Glu Tyr Leu Gly Glu Gly Tyr Ser
    290                 295                 300

Arg Asp Thr Val Ile Lys Ala Thr Val Phe Ser Leu Val Leu Asp Ala
305                 310                 315                 320

Ala Asp Thr Val Ala Leu His Ile Asn Cys Gly Met Ala Leu Leu Ile
                325                 330                 335

```
Asn Asn Gln Asn Ala Leu Lys Lys Ala Gln Glu Glu Ile Asp Thr Lys
            340                 345                 350

Val Gly Lys Asp Arg Trp Val Glu Glu Ser Asp Ile Lys Asp Leu Val
            355                 360                 365

Tyr Leu Gln Ala Ile Val Lys Glu Val Leu Arg Leu Tyr Pro Pro Gly
            370                 375                 380

Pro Leu Leu Val Pro His Glu Asn Val Glu Asp Cys Val Val Ser Gly
385                 390                 395                 400

Tyr His Ile Pro Lys Gly Thr Arg Leu Phe Ala Asn Val Met Lys Leu
                405                 410                 415

Gln Arg Asp Pro Lys Leu Trp Ser Asn Pro Asp Lys Phe Asn Pro Glu
                420                 425                 430

Arg Phe Ile Ala Arg Asp Ile Asp Phe His Gly Gln His Tyr Glu Tyr
                435                 440                 445

Ile Pro Phe Gly Ser Gly Arg Arg Ser Cys Pro Gly Met Thr Tyr Ala
            450                 455                 460

Leu Gln Val Glu His Leu Thr Met Ala His Leu Ile Gln Gly Phe Asn
465                 470                 475                 480

Tyr Arg Thr Pro Thr Asp Glu Pro Leu Asp Met Lys Glu Gly Ala Gly
                485                 490                 495

Ile Thr Ile Arg Lys Val Asn Pro Val Lys Val Ile Ile Thr Pro Arg
            500                 505                 510

Leu Ala Pro Glu Leu Tyr
            515

<210> SEQ ID NO 9
<211> LENGTH: 539
<212> TYPE: DNA
<213> ORGANISM: Nicotiana sp.
<220> FEATURE:
<221> NAME/KEY: CDS
<222> LOCATION: (1)...(539)

<400> SEQUENCE: 9 atg gtt ttt ccc ata gaa gcc ttt gta gga cta gta acc ttc aca ttt      48
Met Val Phe Pro Ile Glu Ala Phe Val Gly Leu Val Thr Phe Thr Phe
1               5                   10                  15 ctc tta tac ttc cta tgg aca aaa aaa tct caa aaa ctt cca aaa ccc      96
Leu Leu Tyr Phe Leu Trp Thr Lys Lys Ser Gln Lys Leu Pro Lys Pro
                20                  25                  30 tta cca ccg aaa atc ccc gga gga tgg ccg gta atc ggc cat ctt ttt     144
Leu Pro Pro Lys Ile Pro Gly Gly Trp Pro Val Ile Gly His Leu Phe
            35                  40                  45 cac ttc aat aac gac ggc gac gac cgt cca tta gct cga aaa ctc gga     192
His Phe Asn Asn Asp Gly Asp Asp Arg Pro Leu Ala Arg Lys Leu Gly
        50                  55                  60 gac tta gct gat aaa tac ggc ccc gtt ttc act ttt cgg cta ggt ctt     240
Asp Leu Ala Asp Lys Tyr Gly Pro Val Phe Thr Phe Arg Leu Gly Leu
65                  70                  75                  80 ccc ctt gtg cta gtt gta agc agt tac gaa gct ata aaa gat tgc ttc     288
Pro Leu Val Leu Val Val Ser Ser Tyr Glu Ala Ile Lys Asp Cys Phe
                85                  90                  95 tct aca aat gat gcc att ttc tcc aat cgt cca gct ttt ctt tat ggc     336
Ser Thr Asn Asp Ala Ile Phe Ser Asn Arg Pro Ala Phe Leu Tyr Gly
                100                 105                 110 gaa tac ctt ggc tac agt aat gcc atg cta ttt tga caa aat acg gac     384
Glu Tyr Leu Gly Tyr Ser Asn Ala Met Leu Phe  *  Gln Asn Thr Asp
            115                 120                 125
```

```
ctt act ggc gaa aaa ata gaa aat tag tca ttc agg aag ttc tct gtg     432
Leu Thr Gly Glu Lys Ile Glu Asn  *  Ser Phe Arg Lys Phe Ser Val
        130                 135                 140 cta gtc gtc tcg aaa aat tga agc acg tga gat ttg gtg aaa ttc aga     480
Leu Val Val Ser Lys Asn  *  Ser Thr  *  Asp Leu Val Lys Phe Arg
            145                 150                 155 cga gca tta aga att tat aca ctc gaa ttg atg gaa att cga gta cga     528
Arg Ala Leu Arg Ile Tyr Thr Leu Glu Leu Met Glu Ile Arg Val Arg
                160                 165                 170 taa atc taa ca                                                      539
 *  Ile  *
```

<210> SEQ ID NO 10
<211> LENGTH: 173
<212> TYPE: PRT
<213> ORGANISM: Nicotiana sp.

<400> SEQUENCE: 10

```
Met Val Phe Pro Ile Glu Ala Phe Val Gly Leu Val Thr Phe Thr Phe
 1               5                  10                  15

Leu Leu Tyr Phe Leu Trp Thr Lys Lys Ser Gln Lys Leu Pro Lys Pro
            20                  25                  30

Leu Pro Pro Lys Ile Pro Gly Gly Trp Pro Val Ile Gly His Leu Phe
        35                  40                  45

His Phe Asn Asn Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Gln Asn Thr Asp Leu
        115                 120                 125

Thr Gly Glu Lys Ile Glu Asn Ser Phe Arg Lys Phe Ser Val Leu Val
    130                 135                 140

Val Ser Lys Asn Ser Thr Asp Leu Val Lys Phe Arg Arg Ala Leu Arg
145                 150                 155                 160

Ile Tyr Thr Leu Glu Leu Met Glu Ile Arg Val Arg Ile
                165                 170
```

<210> SEQ ID NO 11
<211> LENGTH: 666
<212> TYPE: DNA
<213> ORGANISM: Nicotiana sp.
<220> FEATURE:
<221> NAME/KEY: CDS
<222> LOCATION: (1)...(666)

<400> SEQUENCE: 11

```
atg gtt ttt ccc ata gaa gcc att gta gga gca gta acc cta att aca      48
Met Val Phe Pro Ile Glu Ala Ile Val Gly Ala Val Thr Leu Ile Thr
 1               5                  10                  15 ttt ctc tta tac ttc cta tgt aca aaa aaa tct caa aaa cat tca aag      96
Phe Leu Leu Tyr Phe Leu Cys Thr Lys Lys Ser Gln Lys His Ser Lys
            20                  25                  30 ccc tta cca acg aaa atc ccc gga gga tgg ccg gta atc ggc cat ctt     144
Pro Leu Pro Thr Lys Ile Pro Gly Gly Trp Pro Val Ile Gly His Leu
        35                  40                  45
```

```
ttc cac ttc aat aac gac ggc gac gac cgt cca ttt gct cga aaa ctc      192
Phe His Phe Asn Asn Asp Gly Asp Asp Arg Pro Phe Ala Arg Lys Leu
         50                  55                  60 gga gac tta gct gat aaa tac ggc ccc gtt ttc act ttt cgg cta ggt      240
Gly Asp Leu Ala Asp Lys Tyr Gly Pro Val Phe Thr Phe Arg Leu Gly
 65                  70                  75                  80 ctt ccc ctt gtg cta gtt gta agc agt tac gaa gct ata aaa gat tgc      288
Leu Pro Leu Val Leu Val Val Ser Ser Tyr Glu Ala Ile Lys Asp Cys
                 85                  90                  95 ttc tct aca aat gac gcc att ttc tcc aat cgt cca gct ttt ctt tac      336
Phe Ser Thr Asn Asp Ala Ile Phe Ser Asn Arg Pro Ala Phe Leu Tyr
             100                 105                 110 ggc gaa tac ctt ggc tac aat aat aca atg ctt ttt cta gca aat tac      384
Gly Glu Tyr Leu Gly Tyr Asn Asn Thr Met Leu Phe Leu Ala Asn Tyr
             115                 120                 125 gga cct tac tgg cga aaa aat cgt aaa tta gtc att cag gaa gtt ctc      432
Gly Pro Tyr Trp Arg Lys Asn Arg Lys Leu Val Ile Gln Glu Val Leu
130                 135                 140 tct gct agt cgt ctc gaa aaa ttc aaa caa gtg aga ttc acc aga att      480
Ser Ala Ser Arg Leu Glu Lys Phe Lys Gln Val Arg Phe Thr Arg Ile
145                 150                 155                 160 caa acg agc att aag aat tta tac act cga att aat gga aat tcg agt      528
Gln Thr Ser Ile Lys Asn Leu Tyr Thr Arg Ile Asn Gly Asn Ser Ser
                165                 170                 175 acg ata aat cta agt gat tgg tta gaa gaa ttg aat ttt ggt ctg atc      576
Thr Ile Asn Leu Ser Asp Trp Leu Glu Glu Leu Asn Phe Gly Leu Ile
             180                 185                 190 gtg aaa atg atc gct ggg aaa aat tat gaa tcc ggt aaa gga gat gaa      624
Val Lys Met Ile Ala Gly Lys Asn Tyr Glu Ser Gly Lys Gly Asp Glu
             195                 200                 205 caa gtg gaa aga ttt aag aat gcg ttt aag gat ttt atg gtt              666
Gln Val Glu Arg Phe Lys Asn Ala Phe Lys Asp Phe Met Val
210                 215                 220

<210> SEQ ID NO 12
<211> LENGTH: 222
<212> TYPE: PRT
<213> ORGANISM: Nicotiana sp.

<400> SEQUENCE: 12

Met Val Phe Pro Ile Glu Ala Ile Val Gly Ala Val Thr Leu Ile Thr
 1               5                  10                  15

Phe Leu Leu Tyr Phe Leu Cys Thr Lys Lys Ser Gln Lys His Ser Lys
             20                  25                  30

Pro Leu Pro Thr Lys Ile Pro Gly Gly Trp Pro Val Ile Gly His Leu
         35                  40                  45

Phe His Phe Asn Asn Asp Gly Asp Asp Arg Pro Phe Ala Arg Lys Leu
     50                  55                  60

Gly Asp Leu Ala Asp Lys Tyr Gly Pro Val Phe Thr Phe Arg Leu Gly
 65                  70                  75                  80

Leu Pro Leu Val Leu Val Val Ser Ser Tyr Glu Ala Ile Lys Asp Cys
                 85                  90                  95

Phe Ser Thr Asn Asp Ala Ile Phe Ser Asn Arg Pro Ala Phe Leu Tyr
             100                 105                 110

Gly Glu Tyr Leu Gly Tyr Asn Asn Thr Met Leu Phe Leu Ala Asn Tyr
             115                 120                 125

Gly Pro Tyr Trp Arg Lys Asn Arg Lys Leu Val Ile Gln Glu Val Leu
130                 135                 140
```

```
Ser Ala Ser Arg Leu Glu Lys Phe Lys Gln Val Arg Phe Thr Arg Ile
145                 150                 155                 160

Gln Thr Ser Ile Lys Asn Leu Tyr Thr Arg Ile Asn Gly Asn Ser Ser
                165                 170                 175

Thr Ile Asn Leu Ser Asp Trp Leu Glu Glu Leu Asn Phe Gly Leu Ile
            180                 185                 190

Val Lys Met Ile Ala Gly Lys Asn Tyr Glu Ser Gly Lys Gly Asp Glu
        195                 200                 205

Gln Val Glu Arg Phe Lys Asn Ala Phe Lys Asp Phe Met Val
    210                 215                 220

<210> SEQ ID NO 13
<211> LENGTH: 99
<212> TYPE: DNA
<213> ORGANISM: Artificial Sequence
<220> FEATURE:
<223> OTHER INFORMATION: Partial coding sequence selected from SEQ ID
      NO:1

<400> SEQUENCE: 13
gacgaggcct tggatatgaa ggaaggtgca ggcataacca tacgtaaggt aaatccagtg    60
gaattgataa taacgcctcg cttggcacct gagctttac                          99

<210> SEQ ID NO 14
<211> LENGTH: 99
<212> TYPE: DNA
<213> ORGANISM: Artificial Sequence
<220> FEATURE:
<223> OTHER INFORMATION: Partial coding sequence selected from SEQ ID
      NO:3

<400> SEQUENCE: 14
gacgagccct tggatatgaa ggaaggtgca ggcataacta tacgtaaggt aaatcctgtg    60
gaactgataa tagcgcctcg cctggcacct gagctttat                          99

<210> SEQ ID NO 15
<211> LENGTH: 99
<212> TYPE: DNA
<213> ORGANISM: Artificial Sequence
<220> FEATURE:
<223> OTHER INFORMATION: Partial coding sequence selected from SEQ ID
      NO:5

<400> SEQUENCE: 15
gacgagccct tggacatgaa ggaaggtgca ggcataacta tacgtaaggt aaatcctgtg    60
gaactgataa tagcgcctcg cctggcacct gagctttat                          99

<210> SEQ ID NO 16
<211> LENGTH: 99
<212> TYPE: DNA
<213> ORGANISM: Artificial Sequence
<220> FEATURE:
<223> OTHER INFORMATION: Partial coding sequence selected from SEQ ID
      NO:7

<400> SEQUENCE: 16
gatgagccct tggatatgaa agaaggtgca ggcataacta tacgtaaggt aaatcctgtg    60
aaagtgataa ttacgcctcg cttggcacct gagctttat                          99

<210> SEQ ID NO 17
<211> LENGTH: 19
```

```
<212> TYPE: DNA
<213> ORGANISM: Artificial Sequence
<220> FEATURE:
<223> OTHER INFORMATION: Primer

<400> SEQUENCE: 17
cgctctagaa ctagtgatc                                                      19

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tttttgggac aatcagtcaa                                                     20

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
gttagattta tcgtactcga att                                                 23

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
ttcatttcaa attattttat gcacca                                              26

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
atggtttttc ccatagaagc c                                                   21

<210> SEQ ID NO 22
<211> LENGTH: 17
<212> TYPE: DNA
<213> ORGANISM: Artificial Sequence
<220> FEATURE:
<223> OTHER INFORMATION: Primer

<400> SEQUENCE: 22
tcgaggtcga cggtatc                                                        17

<210> SEQ ID NO 23
<211> LENGTH: 1118
<212> TYPE: DNA
<213> ORGANISM: Nicotiana sp.

<400> SEQUENCE: 23
ctgtcattaa agcaacggtg tttgtaagtt catctgtcat ttttcattta ttcactttta         60
```

-continued

| | |
|---|---|
| ttttgaggag cagacatgtt aataataatt tggagcaact gtaaagttat ctatgtgtac | 120 |
| aggttcgagc tcaggtgca accactaatg cttgtattag attatgttgt ctgcatcata | 180 |
| cccctaattg gagtgtggct cttcccgaac cctgcaatgc tggatgctgg atgctttatg | 240 |
| tatcagactg accttttgt taaactatct aaatactaag gatgatttaa taaaaatata | 300 |
| gaatggtaaa cagaaaaaga tgagattatt tttggggcta tatggattcg cccgggcttt | 360 |
| gggaggtaaa acggtatcta ccagttgaga ctttactcca gaactttatc tcgagagctc | 420 |
| tgaataaaaa tgaaatagta tttaccactc caaaatcttt gatggtaaaa agatgagata | 480 |
| taacctctta taattgattg aaccacgttg atagaataaa acttctttac tcccattcag | 540 |
| cataagaaaa atgaaaccaa acggaattct tctcttttt aggggaaat tccttaattg | 600 |
| cttgttgaat atagattcat gtcgttattc tattttaat aatgatgaaa atcaatatag | 660 |
| tcaaagttaa tacttatgtc atttggtttg cggacaagtt atattggaac tatataatac | 720 |
| gtctattata gaatagtgat tatttagagg atatacattt ttttggata aatatttgat | 780 |
| ttattggatt aaaaatagaa tatacaggta aggtctaaaa cgtgtgtttg cttttacact | 840 |
| aaataaactt gacctcgtac aattctaaga aaatatttga aataaatgaa ttatttatt | 900 |
| gttaatcaat taaaaaaatc atagtataga tgagatgtgt gcatacttgg caataactat | 960 |
| actaactaaa acaaggtatg tgaataattg atattccttt tttaattatt ctttttcca | 1020 |
| gagtttggtc ttggatgcag cagacacagt tgctcttcac ataaattggg gaatggcatt | 1080 |
| attgataaac aatcaaaagg ccttgacgaa agcacaag | 1118 |

<210> SEQ ID NO 24
<211> LENGTH: 998
<212> TYPE: DNA
<213> ORGANISM: Nicotiana sp.

<400> SEQUENCE: 24

| | |
|---|---|
| gtaagttcat ctgtcatttt tcatttattc acttttattt tgaggagcag acatgttaat | 60 |
| aataatttgg agcaactgta aagttatcta tgtgtacagg ttcgagcctc aggtgcaacc | 120 |
| actaatgctt gtattagatt atgttgtctg catcataccc ctaattggag tgtggctctt | 180 |
| cccgaaccct gcaatgctgg atgctggatg ctttatgtat cagactgacc ttttgttaa | 240 |
| actatctaaa tactaaggat gatttaataa aaatatagaa tggtaaacag aaaaagatga | 300 |
| gattatttt ggggctatat ggattcgccc gggctttggg aggtaaaacg gtatctacca | 360 |
| gttgagactt tactccagaa ctttatctcg agagctctga ataaaaatga atagtattt | 420 |
| accactccaa atctttgat ggtaaaaaga tgagatataa cctcttataa ttgattgaac | 480 |
| cacgttgata gaataaaact tctttactcc cattcagcat aagaaaaatg aaaccaaacg | 540 |
| gaattcttct ctttttagg gggaaattcc ttaattgctt gttgaatata gattcatgtc | 600 |
| gttattctat ttttaataat gatgaaaatc aatatagtca agttaatac ttatgtcatt | 660 |
| tggtttgcgg acaagttata ttggaactat ataatacgtc tattatagaa tagtgattat | 720 |
| ttagaggata tacatttttt ttggataaat atttgattta ttggattaaa aatagaatat | 780 |
| acaggtaagg tctaaaacgt gtgtttgctt ttacactaaa taaacttgac ctcgtacaat | 840 |
| tctaagaaaa tatttgaaat aaatgaatta ttttattgtt aatcaattaa aaaaatcata | 900 |
| gtatagatga gatgtgtgca tacttggcaa taactatact aactaaaaca aggtatgtga | 960 |
| ataattgata ttcctttttt aattattctt ttttccag | 998 |

<210> SEQ ID NO 25
<211> LENGTH: 20
<212> TYPE: DNA
<213> ORGANISM: Artificial Sequence
<220> FEATURE:
<223> OTHER INFORMATION: PCR Primer

<400> SEQUENCE: 25
ctgtcattaa agcaacggtg					20

<210> SEQ ID NO 26
<211> LENGTH: 20
<212> TYPE: DNA
<213> ORGANISM: Artificial Sequence
<220> FEATURE:
<223> OTHER INFORMATION: PCR Primer

<400> SEQUENCE: 26
ggccttgacg aaagcacaag					20

<210> SEQ ID NO 27
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 27
aagctttgac gccatttttt ccaatcg				27

<210> SEQ ID NO 28
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 28
ctcgagtttt ccagcgatca tcttcac				27

<210> SEQ ID NO 29
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 29
acgtgatcct aaactctggt ctg				23

<210> SEQ ID NO 30
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 30
gcctgcacct tccttcatg					19

<210> SEQ ID NO 31
<211> LENGTH: 20
<212> TYPE: DNA
<213> ORGANISM: Artificial Sequence
<220> FEATURE:
<223> OTHER INFORMATION: oligonucleotide primer

```
<400> SEQUENCE: 31
cggtaatcgg ccatcttttc                                              20

<210> SEQ ID NO 32
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 32
ccgagttttc gagctaatgg a                                            21

<210> SEQ ID NO 33
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 33
caatgacgaa cggcgacag                                               19

<210> SEQ ID NO 34
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 34 atggttttc ccatagaagc c                                             21

<210> SEQ ID NO 35
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 35
tttttgggac aatcagtcaa t                                            21

<210> SEQ ID NO 36
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 36
tgaatgaact gcaggacgag                                              20

<210> SEQ ID NO 37
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 37
aatatcacgg gtagccaacg                                              20
```